United States Patent
Wang et al.

(10) Patent No.: US 12,215,092 B2
(45) Date of Patent: Feb. 4, 2025

(54) PLEIOTROPIC PATHWAY MODIFIER COMPOUNDS AND METHOD OF TREATING DISEASES

(71) Applicant: PPM BIOPHARMA LLC, Berkeley Heights, NJ (US)

(72) Inventors: Mingwen Wang, Berkeley Heights, NJ (US); Linghua Zhang, Berkeley Heights, NJ (US)

(73) Assignee: PPM BIOPHARMA LLC, Berkeley Heights, NJ (US)

( * ) Notice: Subject to any disclaimer, the term of this patent is extended or adjusted under 35 U.S.C. 154(b) by 0 days.

(21) Appl. No.: 18/586,920

(22) Filed: Feb. 26, 2024

(65) Prior Publication Data

US 2024/0300918 A1    Sep. 12, 2024

Related U.S. Application Data

(60) Provisional application No. 63/486,836, filed on Feb. 24, 2023.

(51) Int. Cl.
*C07D 401/04* (2006.01)
*A61P 35/00* (2006.01)

(52) U.S. Cl.
CPC ............ *C07D 401/04* (2013.01); *A61P 35/00* (2018.01)

(58) Field of Classification Search
CPC ............................. C07D 401/04; A61P 35/00
See application file for complete search history.

(56) References Cited

U.S. PATENT DOCUMENTS

| | | |
|---|---|---|
| 8,012,997 B2 | 9/2011 | Robarge et al. |
| 2018/0134684 A1 * | 5/2018 | Bradner ................. A61P 37/00 |

FOREIGN PATENT DOCUMENTS

| | | | |
|---|---|---|---|
| CN | 116023368 A | 4/2023 | |
| WO | 2015/160845 A2 | 10/2015 | |
| WO | 2016/007848 A1 | 1/2016 | |
| WO | 2021/126974 A1 | 6/2021 | |
| WO | WO-2022256623 A1 * | 12/2022 | ............. C12N 9/104 |
| WO | WO-2023078410 A1 * | 5/2023 | .............. A61P 35/00 |

OTHER PUBLICATIONS

WO-2023078410-A1 English machine translation—Google Patents (Year: 2024).*

(Continued)

*Primary Examiner* — Clinton A Brooks
*Assistant Examiner* — Izabela Schmidt
(74) *Attorney, Agent, or Firm* — FOX ROTHSCHILD LLP

(57) ABSTRACT

This patent document reveals a class of pleiotropic pathway modifier (known as PPM) compounds that facilitate the degradation of multiple targeted proteins and regulate various signaling events involved in cancer cell survival and proliferation, as well as immune response. These compounds effectively recruit disease-causing proteins for swift destruction through the ubiquitin-proteasome pathway, exhibiting potent anti-cancer, immunomodulatory, and anti-inflammatory properties. Additionally, disclosed herein are methods for treating diseases encompassing cancers, autoimmune disorders, infections, inflammations, and other ailments.

26 Claims, 10 Drawing Sheets

(56) References Cited

OTHER PUBLICATIONS

Sasso et al., Molecular Glues: The Adhesive Connecting Targeted Protein Degradation to the Clinic, Biochemistry 2023, 62, 601-623, Published: Jul. 20, 2022 (Year: 2022).*
Koduri et al., Targeting oncoproteins with a positive selection assay for protein degraders. Sci Adv. Feb. 5, 2021;7(6): (Year: 2021).*
Bircelj et al., ACS Med. Chem. Lett. 2021, 12, 11, 1733-1738 (Year: 2021).*
Pubchem CID 156524414", National Library of Medicine, [2-(2,6-dioxopiperidin-3-yl)-1-oxo-3H-isoindol-4-yl]urea", Create date: Aug. 21, 2021 (Aug. 21, 2021).

* cited by examiner

PLEIOTROPIC PATHWAY MODIFIER COMPOUNDS AND METHOD OF TREATING DISEASES

CROSS-REFERENCE TO RELATED APPLICATIONS

This application claims priority to Provisional Application No. 63/486,836, filed Feb. 24, 2023, the disclosures of which is hereby incorporated by reference in the entirety.

TECHNICAL FIELD

The present invention pertains to novel pleiotropic pathway modifier (PPM) compounds that possess the ability to induce degradation of multiple proteins involved in various signaling pathways associated with carcinogenesis and immunity. Additionally, disclosed herein are methods for treating diseases encompassing cancer, autoimmune disorders, infections, inflammation, and other unmet medical conditions.

BACKGROUND

Targeted protein degradation (TPD) is a rapidly exploding drug discovery strategy which uses small molecules to recruit disease-causing proteins for rapid destruction via the ubiquitin-proteasome pathway. It shows great potential for treating diseases such as cancer, autoimmune, infection, inflammation, and many other diseases with unmet needs.

One of the major pathways to regulate proteins post-translationally is ubiquitin-dependent proteolysis. The first step in selective degradation is the ligation of one or more ubiquitin molecules to a protein substrate. Ubiquitination occurs through the activity of ubiquitin-activating enzymes (E1), ubiquitin-conjugating enzymes (E2), and ubiquitin-protein ligases (E3), which act sequentially to catalyze the attachment of ubiquitin to lysine residues of substrate proteins. The E3s confer specificity to ubiquitination reactions by binding directly to substrate.

Most small molecule drugs bind enzymes or receptors in tight and well-defined pockets. On the other hand, protein-protein interactions are notoriously challenging to target using small molecules due to their large contact surfaces and shallow grooves or flat interfaces involved. E3 ligase confer substrates specificity for ubiquitination, and therefore, are more attractive as therapeutic targets. One E3 ligase as an exciting therapeutic target is cereblon (CRBN). CRBN is identified as the primary target for the clinically approved immunomodulatory drugs including thalidomide, lenalidomide and analogs. The field of target protein degradation promoted by small molecules has been intensively explored over the recent few years. Many heterobifunctional compounds have been invented as target protein degraders, such as PROteolysis TArgeting Chimeras (PROTACs).

Compared to traditional pharmacological target protein inhibition, degraders offer two crucial advantages. Firstly, targeted degradation is a catalytic process as degraders act through transient binding rather than competitive occupancy and dissociate after promoting polyubiquitination of the disease-causing protein. A single degrader can efficiently eliminate multiple copies of a pathogenic protein at very low doses. Secondly, while protein inhibitors merely block the active site of a pathogenic protein, degraders completely abolish all its functions, thereby providing enhanced sensitivity towards drug-resistant targets and an improved likelihood of affecting nonenzymatic protein functions.

The establishment of the PROTAC strategy was further augmented by the finding of degrader compounds that became known as molecular glues. Molecular glues are monovalent small molecules (<500 Da) that reshape the surface of an E3 ligase receptor, promoting novel protein-protein interactions (PPIs). Molecular glues are expected to have better pharmacological properties than PROTACs. PROTACs compose of two active domains and a long linker, having large molecular weights and complexity of structures, therefore, there are potential huge hurdles to overcome the bioavailability or pharmacokinetic-pharmacodynamic (PK/PD) issues.

In contrast, molecular glues are much smaller thus more easily abide by Lipinski's rule of five for drug conformity, which suggests upper limit of molecular properties expected to enhance the probability for good oral bioavailability.

There is an ongoing need in the art to provide methods and compositions useful for regulating protein expression in tumor cells, immune cells, neuron cells, as well as other types of cells involved in various diseases. It is especially promising to induce degradation of disease-causing proteins in cancer and other diseases.

SUMMARY

The compounds described in this patent document address this specific need. The pleiotropic pathway modifiers (PPM) disclosed herein are a class of multifunctional molecular glue compounds that bind both cereblon (CBRN) and the transcriptional co-factor histone deacetylases (HDACs). Unlike reported targeted protein degraders such as PROTACs or molecular glues, PPM compounds are unique molecular glues with smaller MWs, potentially having improved bioavailability. PPM compounds not only induce degradation of proteins implicated in carcinogenesis and immunity, such as c-MYC, HDAC, IRF4, and Ikaros Zinc Finger Transcription Factors (IKZFs), but also directly inhibit the enzymatic activities of HDACs, thereby regulating expression of oncogenes in cells.

An aspect of this patent document provides a compound or a pharmaceutically acceptable salt thereof, wherein the compound is represented by Formula I,

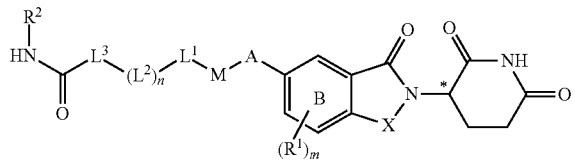

Formula I wherein:
X is $CH_2$ or C=O,
$R^1$ in each instance is independently selected from the group consisting of $C_{1-4}$alkyl, $OC1_{-4}$alkyl, $NR^aR^b$, halo $C_{1-4}$alkyl, halogen, OH, CN, phenyl and 5- or 6-membered heteroaryl, wherein the phenyl and 5- or 6-membered heteroaryl are optionally substituted with one or more substituents selected from the group consisting of $C_{1-4}$alkyl, $OC_{1-4}$alkyl, $NR^aR^b$, halo $C_{1-4}$alkyl, halogen, OH, and CN;
$R^a$ and $R^b$ in each instance is independently H or $C_{1-4}$alkyl;
$R^2$ is H, OH or $C_{1-4}$alkyl;
A is $C_{1-3}$alkylene or void, M is O, OC$_{1-3}$alkylene, NR$^a$ (R$^a$ is H or C$_{1-4}$alkyl), NHC(O)NH, O(CO)NH, NHC(O)O, or NHC(O), wherein O of OC$_{1-3}$alkylene is bonded to A or the B ring (when A is void);

L$^1$ is NH, 3-6 membered heterocyclic, 6-membered aryl or 6-membered heteroaryl, haloC$_{1-2}$alkylene, C$_{1-3}$alkylene or void, wherein the aryl or heteroaryl is optionally substituted with one or more substituents such as C$_{1-4}$alkyl, OR$^a$, SR$^a$, NR$^a$R$^b$, COOR$^a$, CN, F, Cl, Br, CF$_3$, 3-6 membered cycloalkyl (e.g. cyclopropyl), OC$_{1-4}$alkyl, NR$^a$R$^b$, and haloC$_{1-4}$alkyl, wherein R$^a$ and R$^b$ in each instance is independently H or C$_{1-4}$alkyl;

L$^2$ in each instance is independently selected from the group consisting of 3-6 membered heterocylic, 6-membered aryl, 6-membered heteroaryl, —(CH$_2$)$_a$C(O)NR$^a$—, —C(O)NR$^a$—, —(CH$_2$)$_a$C(O)NR$^a$(CH$_2$)$_b$—, —(CH$_2$)$_a$—, —(CH$_2$)$_a$O(CH$_2$CH$_2$O)$_c$—, —(CH$_2$)$_a$S, —(CH$_2$)heterocyclic-, —(CH$_2$)$_a$C(O)—, —(CH$_2$)$_a$NR$^a$—, —CR$^a$=N—NR$^a$—, —CR$^a$=N—O—, —CR$^a$=N—NR$^b$—CO—, —N=N—CO—, —S—S—, and any combination thereof, wherein a, b, and c are each an integer selected from 0 to 25, all subunits (e.g. 0, 1, 2, 3, 4, 5, 6, 7, 8, 9, 10, . . . 23, 24 and 25) included;

L$^3$ is C$_{1-20}$alkylene, C$_{2-20}$alkenlene, C$_{2-20}$alkynlene or void;

m is 0, 1, 2 or 3;

n is an integer selected from 0 to 25, all subunits included;

or a pharmaceutically acceptable salt thereof, provided that when A, L$^1$ and (L$^2$)$_n$ are void and M is NHC(O)NH or NHC(O), M is not in an ortho position to X. The carbon with an asterisk may be R or S in configuration.

Another aspect of this patent document discloses a pharmaceutical composition comprising the compound described herein or the pharmaceutically acceptable salt, isomer, or prodrug thereof.

Another aspect of this disclosure provides a method of treating a disease in a subject comprising administering to the subject in need a therapeutically effective amount of a compound of Formula I, a pharmaceutically acceptable salt or isomer thereof, or a pharmaceutical composition thereof.

Another aspect provides a method of degrading a target protein, comprising contacting the target protein with a therapeutically effective amount of the compound disclosed herein or pharmaceutically acceptable salt thereof.

DESCRIPTIONS OF THE DRAWINGS

FIG. 3 shows that Compound 4 reduced c-MYC and HDAC expression in H929 human myeloma cells (DMSO, vehicle control; Pom, pomalidomide. GAPDH as the sample loading control).

Figure 3A:
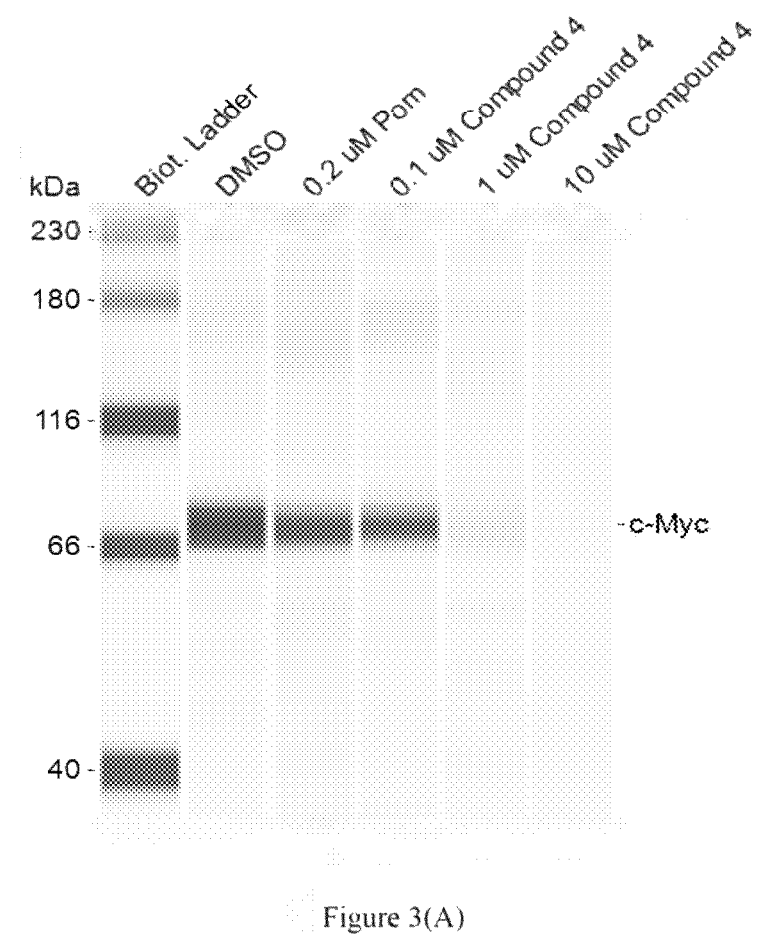

FIG. 3(A) shows that Compound 4 reduced c-MYC expression in H929 cells in a concentration-dependent manner.

Figure 3B:
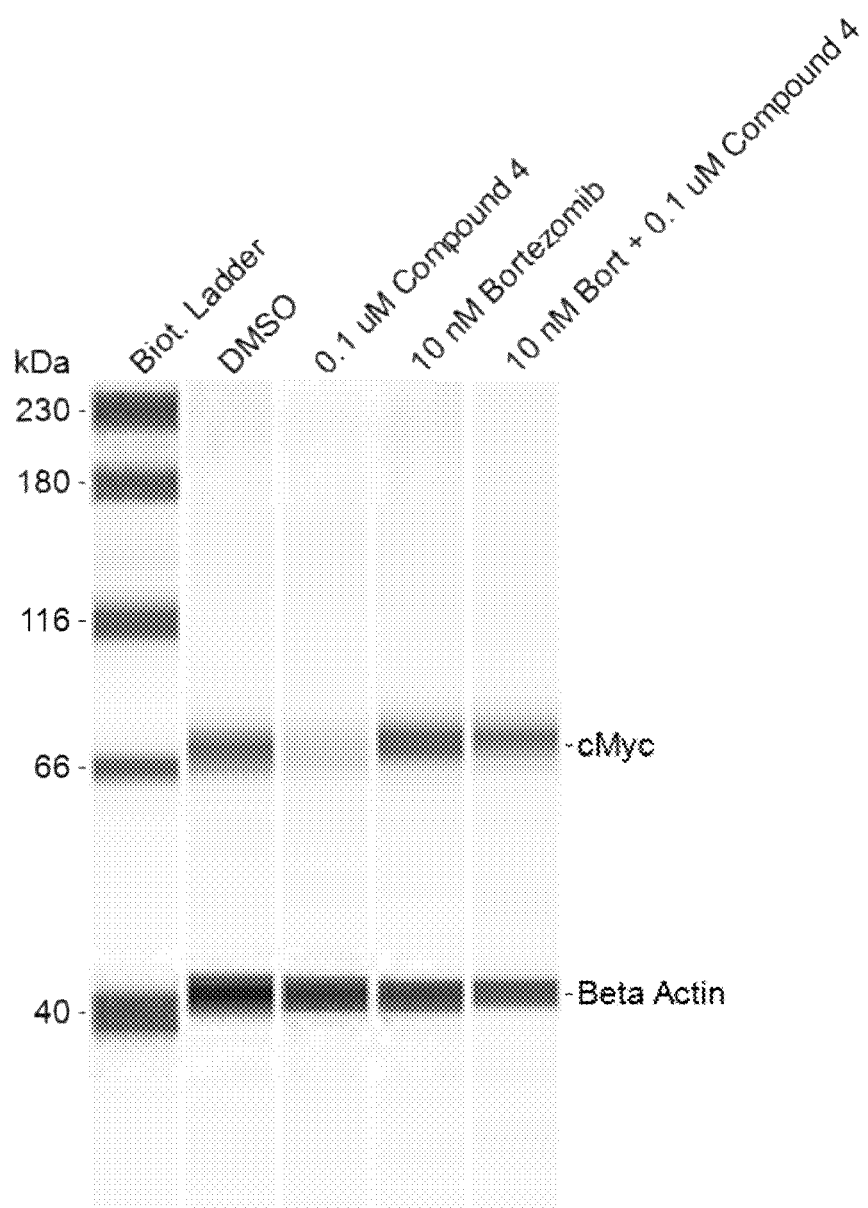

FIG. 3(B) shows that pretreatment of cells with the proteasome inhibitor bortezomib prevented Compound 4 induced c-MYC degradation in H929 cells, indicating that Compound 4 induced protein degradation should be via ubiquitin-proteasome pathway.

Figure 3C:
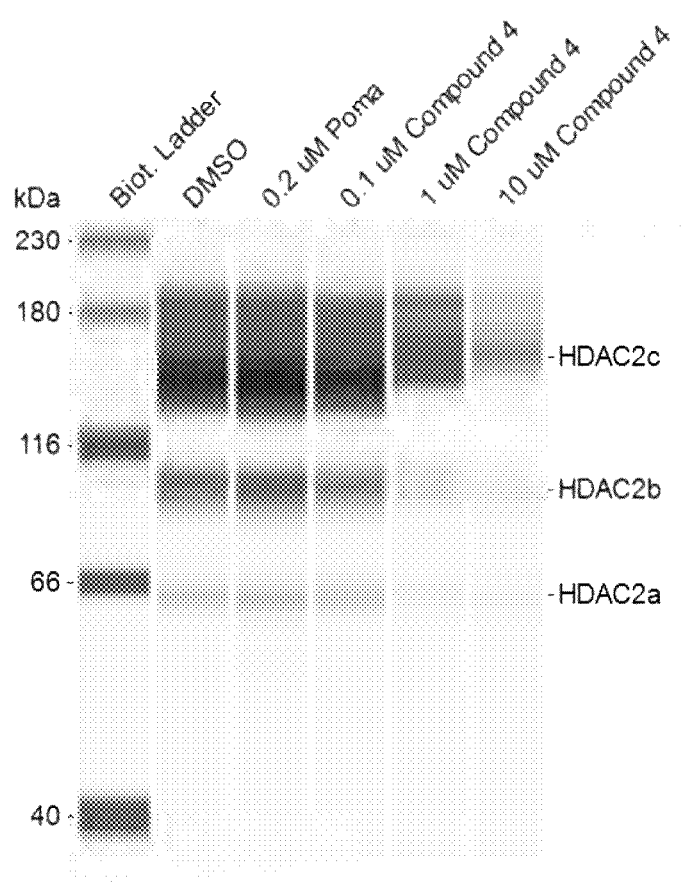

FIG. 3(C) shows that Compound 4 reduced HDAC2 expression in H929 cells in a concentration-dependent manner.

Figure 3D:
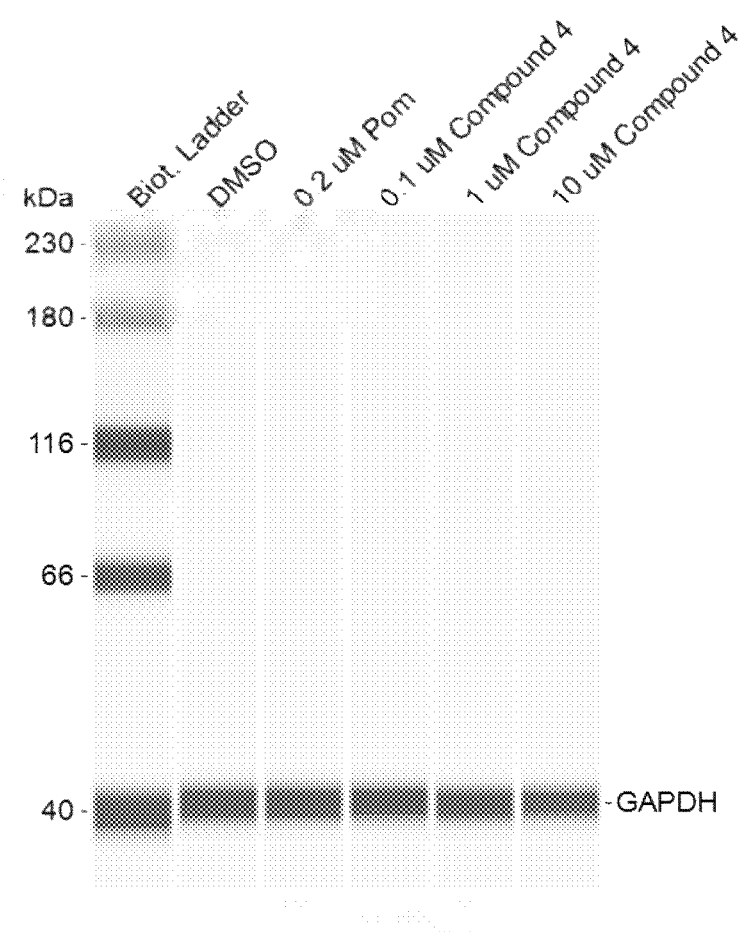

FIG. 3(D) shows that Compound 4 had no effect on GAPDH expression in H929 cells (use as the sample loading control)

Figure 4:
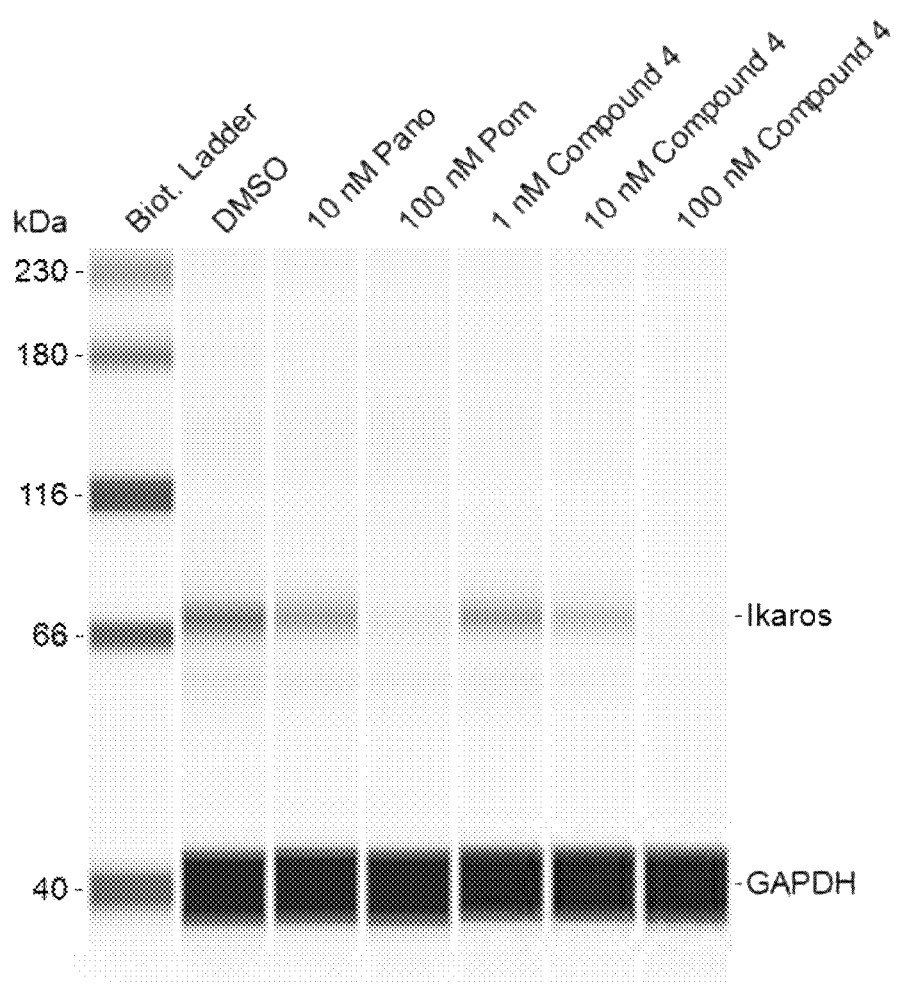

FIG. 4 shows that Compound 4 reduced Ikaros expression in Jurkat cells (DMSO, vehicle control; Pano, Panobinostat; Pom, pomalidomide. GAPDH as the sample loading control).

Figure 5:
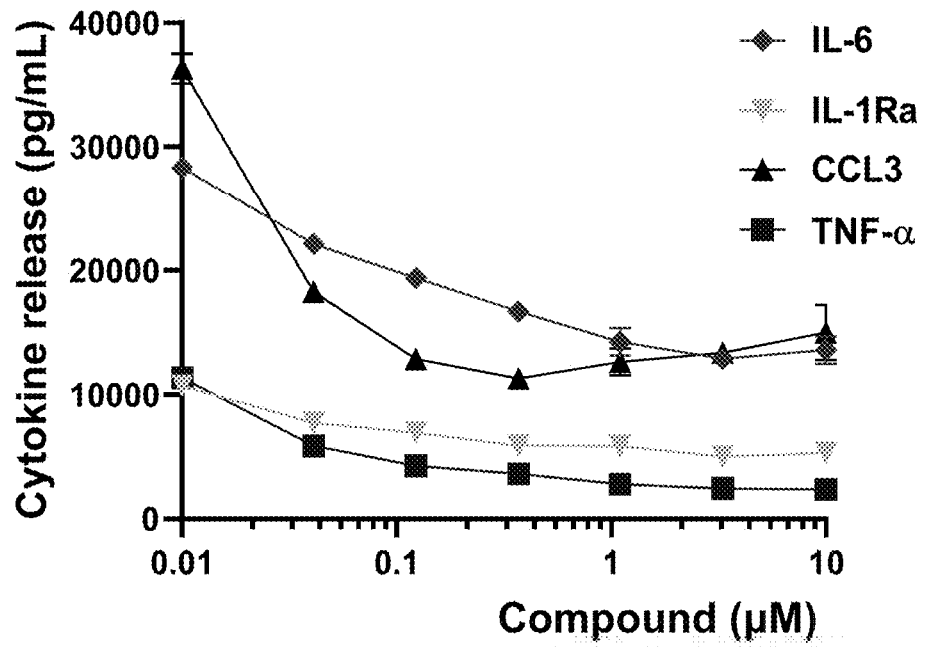

FIG. 5 shows that Compound 4 suppressed cytokine production from polyinosinic-polycytidylic acid (Poly (I:C)) induced PBMC in a concentration-dependent manner.

Figure 6:
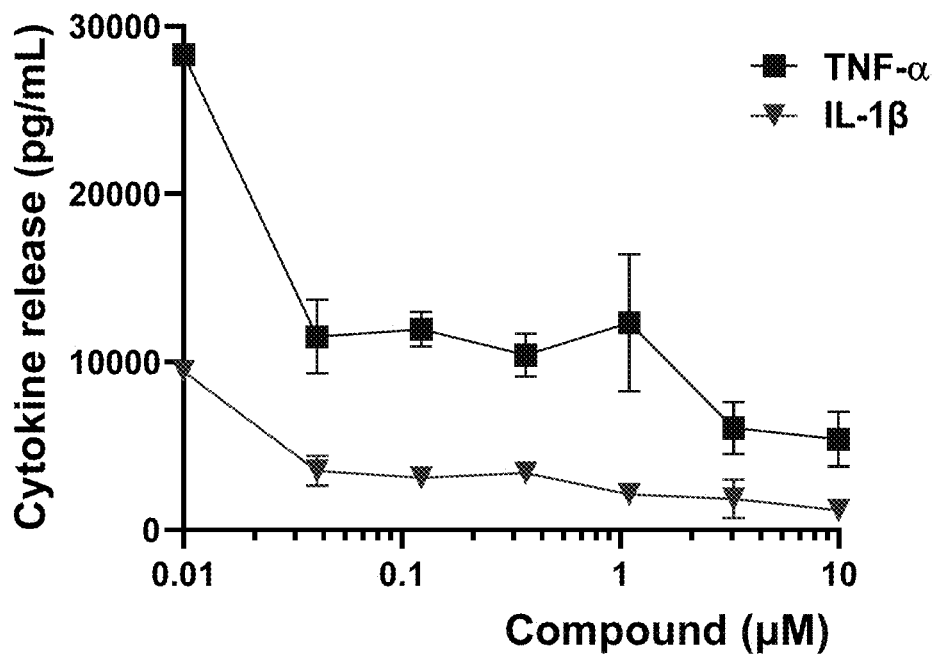

FIG. 6 shows that compound 4 suppressed cytokine production from lipopolysaccharides (LPS) induced PBMC in a concentration-dependent manner.

Figure 7:
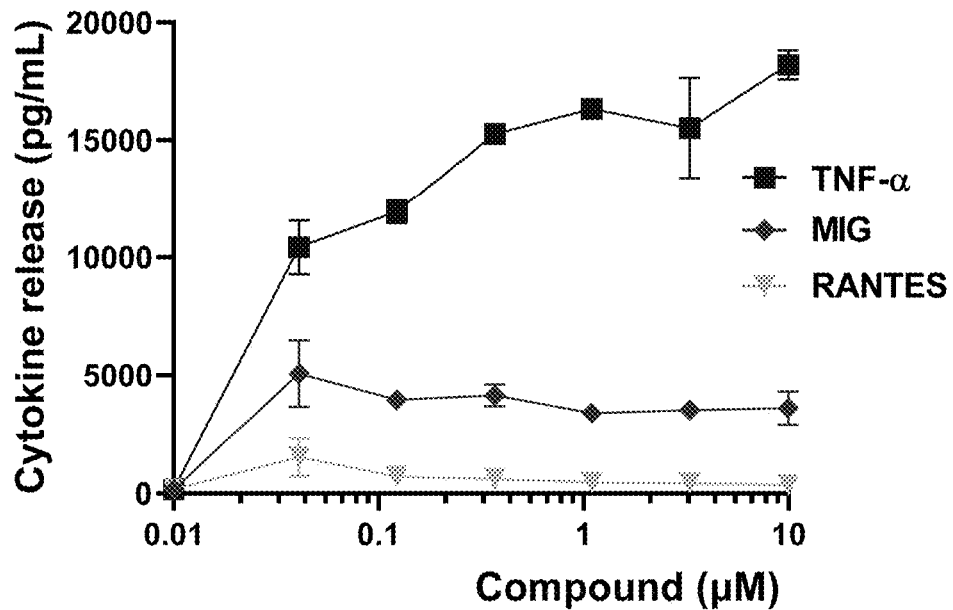

FIG. 7 shows that Compound 4 compounds enhanced cytokine production from Staphylococcal enterotoxin B (SEB) induced PBMC in a concentration-dependent manner.

Figure 8:
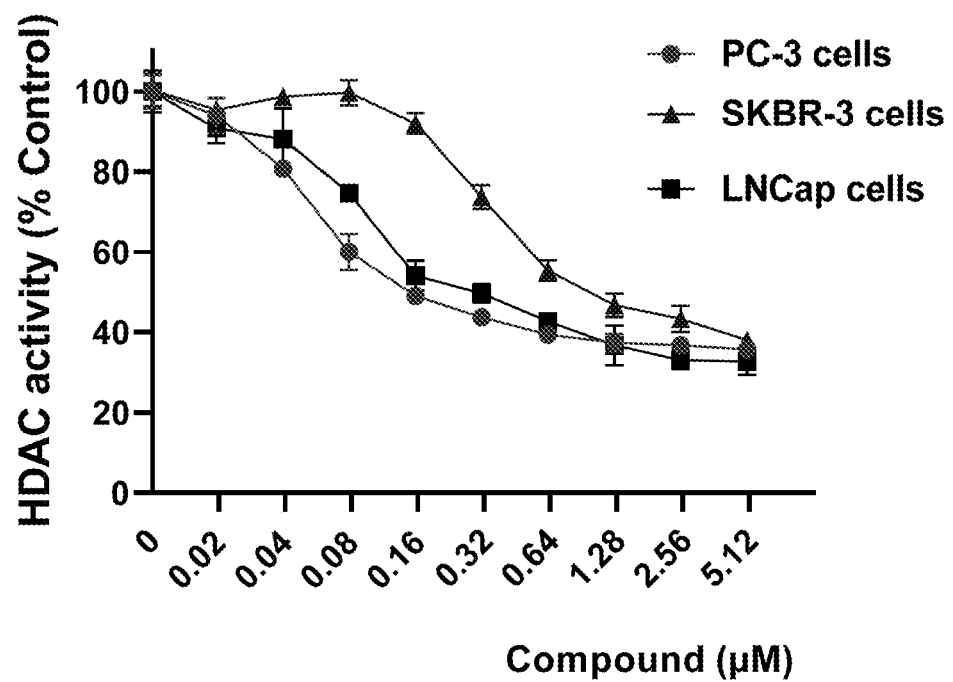

FIG. 8 shows that Compound 4 suppressed intracellular HDAC activity in human cancer cells in a concentration-dependent manner.

Figure 9:
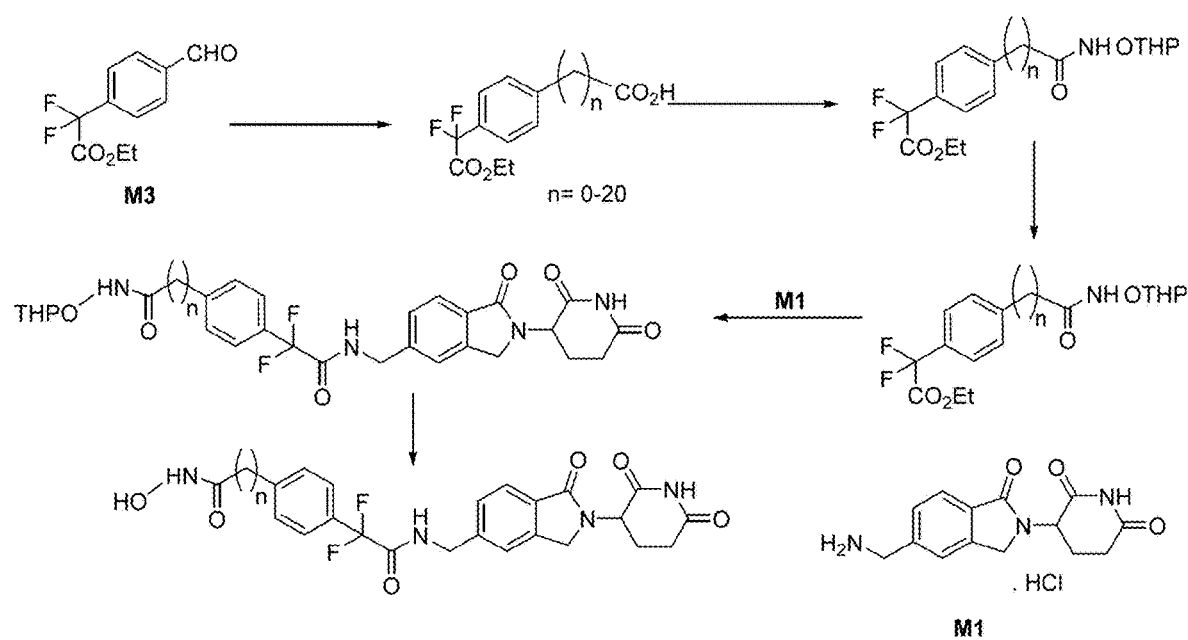

FIG. 9 illustrates the synthesis of a compound under Formula I-j.

Figure 10:
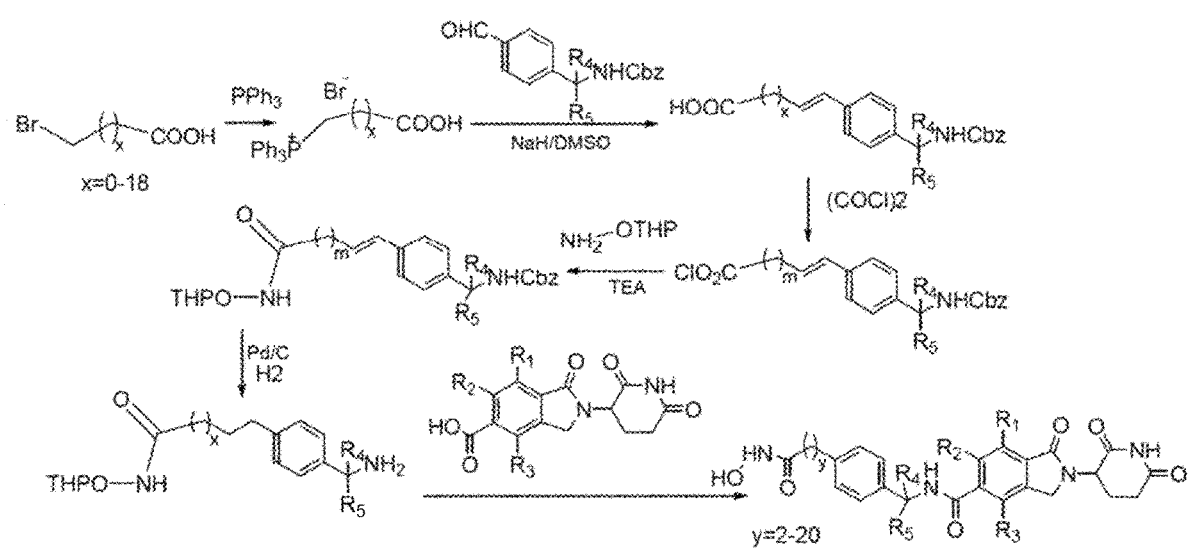

FIG. 10 illustrates the synthesis of a compound under Formula I-k.

DETAILED DESCRIPTION

Various embodiments of this patent document disclose compounds for targeted protein degradation (TPD). The TPD approach uses small molecules to recruit disease-causing proteins for rapid destruction via the ubiquitin-proteasome pathway and can therefore be applied to the treatment of diseases including cancer, autoimmune disease, infection, and inflammation.

The compounds disclosed herein function as pleiotropic pathway modifiers (PPMs). They are a type of multifunctional compounds, inducing an interaction between a substrate receptor of a protease (e.g. cereblon (CBRN)/E3 ligase) and a target protein leading to proteolysis of the target protein. Unlike other reported targeted protein degraders such as PROTACs, the PPMs can also directly block enzymatic activities of the target protein.

While the following text may reference or exemplify specific embodiments of a compound or a method of treating a disease or condition, it is not intended to limit the scope of the compound or method to such particular reference or examples. Various modifications may be made by those skilled in the art, in view of practical and economic considerations, such as the substitutions of the compound and the amount or administration of the compound for treating or preventing a disease or condition.

The articles "a" and "an" as used herein refers to "one or more" or "at least one," unless otherwise indicated. That is, reference to any element or component of an embodiment by the indefinite article "a" or "an" does not exclude the possibility that more than one element or component is present.

The term "pharmaceutical composition" refers to a mixture of a compound disclosed herein with other chemical components, such as diluents or additional carriers. The pharmaceutical composition facilitates administration of the compound to an organism. Multiple techniques of administering a pharmaceutical composition exist in the art including, but not limited to, oral, injection, aerosol, parenteral, and topical administration. In some embodiments, pharmaceutically acceptable salts of the compounds disclosed herein are provided.

The term "subject" encompasses any animal, but preferably a mammal, e.g., human, non-human primate, a dog, a cat, a horse, a cow, or a rodent. More preferably, the subject is a human.

The term "carrier" refers to a chemical compound that facilitates the incorporation of a compound into cells or tissues.

The term "diluent" refers to chemical compounds diluted in water that will dissolve the composition of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound. As used herein, an "excipient" refers to an inert substance that is added to a composition to provide, without limitation, bulk, consistency, stability, binding ability, lubrication, disintegrating ability, etc., to the composition. A "diluent" is a type of excipient.

The term "physiologically acceptable" or "pharmaceutically acceptable" refers to a carrier or diluent that does not abrogate the biological activity and properties of the compound.

The term "therapeutically effective amount" refers to an amount of a compound effective to prevent, alleviate or ameliorate symptoms of disease or prolong the survival of the subject being treated. Determination of a therapeutically effective amount is well within the capability of those skilled in the art, especially in light of the detailed disclosure provided herein.

The term "alkyl" refers to monovalent saturated alkane radical groups particularly having up to about 18 carbon atoms, more particularly as a lower alkyl, from 1 to 8 carbon atoms and still more particularly, from 1 to 6 carbon atoms. The hydrocarbon chain may be either straight-chained or branched. The term "$C_{1-10}$ alkyl" or "C1-C10 alkyl" refers to alkyl groups having 1, 2, 3, 4, 5, 6, 7, 8, 9 or 10 carbon atoms. Similarly, the term "$C_{1-4}$alkyl" refers to alkyl groups having 1, 2, 3, or 4 carbon atoms. Non-limiting examples of alkyls include groups such as methyl, ethyl, n-propyl, iso-propyl, n-butyl, iso-butyl, tert-butyl, n-hexyl, n-octyl, tert-octyl and the like.

The term "alkylene" refers to a divalent hydrocarbon which may be either straight-chained or branched. Different from alkyl which has only one point of bonding with other groups or atoms, alkylene has two points of bonding. Non-limiting examples include groups such as $CH_2$, $(CH_2)_2$, $CH_2CH(CH_3)$, and the like. A $C_{1-6}$ alkylene has 1, 2, 3, 4, 5 or 6 carbons. A $C_{1-4}$alkylene has 1, 2, 3 or 4 carbons.

The term "alkenlene" refers to a divalent hydrocarbon which may be either straight-chained or branched. Different from alkylene which has a saturated backbone, alkenlene contains a double bond.

The term "$C_{1-4}$ alkoxy" includes an alkyloxy group having 1, 2, 3 or 4 carbons.

The term "carbocycle" or "cycloalkyl" refers to 3 to 10 membered cyclic hydrocarbyl groups having only carbon atoms as ring atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, l-methylcyclopropyl, 2-methylcyclopentyl, 2-methylcyclooctyl, and the like, and multiple ring structures such as adamantanyl, and the like.

The term "haloalkyl" refers to a $C_{1-10}$alkyl, straight chain or branched, in which one or more hydrogen has been replaced by a halogen. Non-limiting examples of haloalkyls include $CHF_2$, $CFH_2$, $CF_3$, $CF_2CH_3$, $CH_2CF_3$, and $CH_2CH_2F$. In some embodiments, the alkyl in haloalkyl has 1, 2, 3 or 4 carbons. Likewise, the term "haloalkylene" refers to an alkylene, straight or branched, in which one or more hydrogen has been replaced by a halogen. Non-limiting examples of haloalkylenes include CHF, $CF_2$, and $CH_2CF_2$.

The term "heterocycle" or "heterocycloalkyl" refers to 3 to 10 membered substituted or non-substituted non-aromatic cyclic groups where one or more carbon ring atoms are replaced with hetero atoms or groups containing heteroatoms (e.g. NH, $NC_{1-4}$ alkyl O, and S). Nonlimiting examples include pyrrolidine, piperidine, piperazine, N-methyl-piperazine, and morpholine. Optional substituents include $C_{1-6}$ alkyl, $C_{1-4}$ alkoxy, halogen, haloalkyl, sulfonamido, and amido.

The term "aryl" is intended to mean any stable monocyclic or bicyclic carbon ring of up to 7 members in each ring, wherein at least one ring is aromatic and all ring atoms of the aromatic ring are carbon atoms. Typical aryl groups include, but are not limited to, groups derived from aceanthrylene, acephenanthrene, anthracene, azulene, benzene, fluoranthene, fluorene, hexalen, hexaphene, hexylene, as-indacene, s-indacene, indane, indene, naphthalene, astacene, octaphene, octylene, ovalene, penta-2,4-diene, pentacene, pentalene, pentaphene, perylene, phenalene, phenanthrene, picene, and the like. Particularly, an aryl group comprises from 6 to 10 or 6 to 14 carbon atoms.

The term "hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloheteroalkyl.

The term "halogen" refers to F, Cl, Br, or I.

The term "carboxamide" refers to a group of —CONRR, wherein each R is independently a hydrogen, $C_{1-6}$ alkyl, 3-7 membered carbocycle, 3-7 membered heterocycle, 5-10 membered heteroaryl or 6-10 membered aryl. The two R groups may link up to form a 3-7 membered carbocycle, 3-7 membered heterocycle, 5-10 membered heteroaryl or 6-10 membered aryl.

The term "amido" refers to a group of —NRCOR', where R is hydrogen or $C_{1-4}$ alkyl and R' is $C_{1-6}$ alkyl, 3-7 membered carbocycle, 3-7 membered heterocycle, 5-10 membered heteroaryl or 6-10 membered aryl.

The term "oxo" refers to =O as a substituent. Nonelimiting examples of include pyrrolidinone (oxo on pyrrolidine) and cyclopentanone.

The term "heteroaryl" refers to groups having 5 to 14 ring atoms, preferably 5, 6, 9, or 10 ring atoms, having 6, 10, or 14 π electrons shared in a cyclic array, wherein at least one ring atom contributing to the shared π electrons in the cyclic array is a heteroatom. Typical heteroaryl groups include, but are not limited to, groups derived from acridine, carbazole, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, phenanthridine, phenanthroline, phenazine, phthalazine, phthalimide, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-15 membered heteroaryl, with 5-10 membered heteroaryl being particularly preferred.

The term "treating" or "treatment" of any disease or condition refers, in some embodiments, to ameliorating the disease or disorder (i.e., arresting or reducing the development of the disease or at least one of the clinical symptoms thereof). In some embodiments "treating" or "treatment" refers to ameliorating at least one physical parameter, which may not be discernible by the subject. In some embodiments, "treating" or "treatment" refers to modulating the disease or disorder, either physically, (e.g., stabilization of a discernible symptom), physiologically, (e.g., stabilization of a physical parameter), or both. In some embodiments, "treating" or "treatment" refers to delaying the onset of the disease or disorder, or even preventing the same. "Prophylactic treatment" is to be construed as any mode of treatment that is used to prevent progression of the disease or is used for precautionary purpose for persons at risk of developing the condition.

The term "pharmaceutically acceptable salts" means salts of compounds of the present invention which are pharmaceutically acceptable, as defined above, and which possess the desired pharmacological activity. Non-limiting examples of such salts include acid addition salts formed with inorganic acids such as hydrochloric acid, hydrobromic acid, sulfuric acid, nitric acid, and phosphoric acid; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphor sulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, and trimethylacetic acid. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Non-limiting examples of acceptable organic bases include ethanolamine, diethanolamine, triethanolamine, tromethamine, and N-methylglucamine. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in Handbook of Pharmaceutical Salts: Properties, and Use (P. H. Stahl & C. G. Wermuth eds., Verlag Helvetica Chimica Acta, 2002).

The term "target protein" is used to describe a protein or polypeptide, which is a target for binding to a compound disclosed herein and degradation via proteolysis. Target proteins that may be bound to the compound disclosed herein and degraded via proteolysis (e.g. by the ligase to which the ubiquitin ligase binding moiety is bound) include structural proteins, receptors, enzymes, cell surface proteins, proteins pertinent to the integrated function of a cell, including proteins involved in catalytic activity, aromatase activity, motor activity, helicase activity, metabolic processes (anabolism and catabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eukaryotes and prokaryotes, including microbes, viruses, fungi and parasites, including humans, microbes, viruses, fungi and parasites, among numerous others, as targets for drug therapy, other animals, including domesticated animals, microbials for the determination of targets for antibiotics and other antimicrobials and plants, and even viruses, among numerous others.

An aspect of this patent document provides a compound or a pharmaceutically acceptable salt thereof, wherein the compound is represented by Formula I,

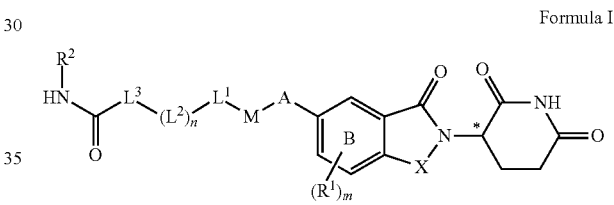

Formula I wherein:
X is $CH_2$ or C=O,
$R^1$ in each instance is independently selected from the group consisting of C1-4alkyl, $OC_{1-4}$alkyl, $NR^aR^b$, halo $C_{1-4}$alkyl, halogen, OH, CN, phenyl and 5- or 6-membered heteroaryl, wherein the phenyl and 5- or 6-membered heteroaryl are optionally substituted with one or more substituents selected from the group consisting of $C_{1-4}$alkyl, $OC_{1-4}$alkyl, $NR^aR^b$, halo $C_{1-4}$alkyl, halogen, OH, and CN;
$R^a$ and $R^b$ in each instance is independently H or $C_{1-4}$alkyl;
$R^2$ is H, OH or $C_{1-4}$alkyl;
A is $C_{1-3}$alkylene or void,
M is O, $OC_{1-3}$alkylene, $NR^a$ ($R^a$ is H or $C_{1-4}$alkyl), NHC(O)NH, O(CO)NH, NHC(O)O, or NHC(O), wherein O of $OC_{1-3}$alkylene is bonded to A or the B ring;
$L^1$ is NH, 3-6 membered heterocyclic, 6-membered aryl or 6-membered heteroaryl, halo$C_{1-2}$alkylene, $C_{1-3}$alkylene or void, wherein the aryl or heteroaryl is optionally substituted with one or more substituents such as $C_{1-4}$alkyl, OH, SH, $NR^aR^b$, COOH, CN, F, Cl, Br, $CF_3$, 3-6 membered cycloalkyl, $OC_{1-4}$alkyl, $NR^aR^b$, and halo$C_{1-4}$alkyl.
$L^2$ in each instance is independently selected from the group consisting of 3-6 membered heterocyclic, 6-membered aryl, 6-membered heteroaryl, $-(CH_2)_aC(O)NR^a-$, $-C(O)NR^a-$, $-(CH_2)_aC(O)NR^a(CH_2)_b-$, $-(CH_2)_a-$, $-(CH_2)_aO(CH_2CH_2O)_c-$, $-(CH_2)_aS$, $-(CH_2)_a$heterocyclyl-, $-(CH_2)_aC(O)-$, $-(CH_2)_a$ NR$^a$—, —CR$^a$=N—NR$^a$—, —CR$^a$=N—O—, —CR$^a$=N—NR$^b$—CO—, —N=N—CO—, —S—S—, and any combination thereof, wherein a, b, and c are each an integer selected from 0 to 25, all subunits (e.g. 0, 1, 2, 3, 4, 5, 6, 7, 8, 9, 10, . . . 23, 24 and 25) included;

L$^1$ is C$_{1-20}$alkylene, C$_{2-20}$alkenlene, C$_{2-20}$alkynlene or void;

m is 0, 1, 2 or 3;

n is an integer selected from 0 to 25, all subunits included;

or a pharmaceutically acceptable salt thereof, provided that when A, L$^1$ and (L$^2$)$_n$ are void and M is NHC(O), M is not in an ortho position to X.

In each of the embodiments disclosed herein, when one or more chiral centers are present, each chiral center is independently R or S in configuration.

In some embodiments of M, the nitrogen of NHC(O)NH, O(CO)NH, NHC(O)O or NHC(O) is bonded to A or the B ring (when A is void). In some embodiments of M, the nitrogen of NHC(O)NH, O(CO)NH, NHC(O)O or NHC(O) is bonded to L$^1$.

In some embodiments, X is CH$_2$ and R$^2$ is OH.

In some embodiments, X is CH$_2$, A is C$_{1-3}$alkylene, M is NHC(O), and (L$^2$)$_n$ is optional and comprises —(CH$_2$)$_a$O(CH$_2$CH$_2$O)$_c$—. In some embodiments, A is methylene.

In some embodiments, the compound of Formula I is represented by Formula I-a, wherein R$^3$ and R$^{3'}$ are independently H, F, Cl or Me. Alternatively, one of R$^3$ and R$^{3'}$ is H, F, or Cl. and the other is CF2, CF3, or Me. In some embodiments, both of R$^3$ and R$^{3'}$ are H. In some embodiments, m is 0. In some embodiments, both of R$^3$ and R$^{3'}$ are H, and m is 0. In some embodiments, L$^1$ is NH, 3-6 membered heterocyclic, 6-membered aryl or 6-membered heteroaryl, or haloC$_{1-2}$alkylene.

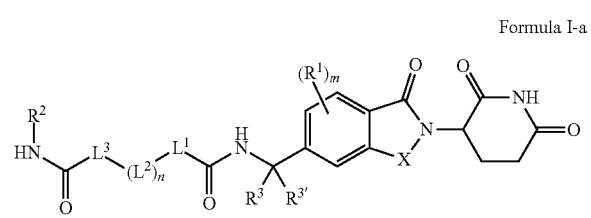

Formula I-a

In some embodiments, A is methylene, L$^1$ is 6-membered aryl, n is 0. In some embodiments, A is methylene, L$^1$ is NH, n is 0. In some embodiments, A is methylene, L$^1$ is 6 membered heterocyclic, n is 0. In some embodiments. A is methylene, L$^1$ is NH, and (L$^2$)n comprises optionally substituted phenyl. In some embodiments, A is methylene, L$^1$ is optionally substituted phenyl, (L$^2$)$_n$ comprises 6 membered heterocyclic. In some embodiments, A is methylene, L$^1$ is halo-methylene, (L$^2$)$^n$ comprises optionally substituted phenyl.

In some embodiments, X is CH$_2$, A is void, M is NHC(O), and (L$^2$)$_n$ optionally comprises —(CH$_2$)$_a$O(CH$_2$CH$_2$O)$_c$—.

In some embodiments, the compound of Formula I is represented by Formula I-b.

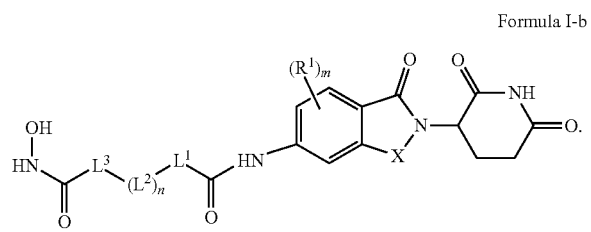

Formula I-b

In some embodiments, L$^1$ is 6-membered aryl, n is 0. L$^1$ is NH$_2$, n is 0. In some embodiments, L$^1$ is 6 membered heterocyclic, n is 0. In some embodiments, L$^1$ is NH, (L$^2$)n comprises optionally substituted phenyl. In some embodiments, L$^1$ is optionally substituted phenyl, (L$^2$)n comprises 6-membered heterocyclic. In some embodiments, L$^1$ is halomethylene, (L$^2$)n comprises optionally substituted phenyl. In some embodiments, L$^1$ is phenyl, L$^3$ is C$_{3-9}$alkylene, and n is 0.

In some embodiments, A is void, M is O or OC$_{1-3}$alkylene, and (L$^2$)$_n$ optionally comprises —(CH$_2$)$_a$O(CH$_2$CH$_2$O)$_c$—.

In some embodiments, the compound of Formula I is represented by Formula I-c.

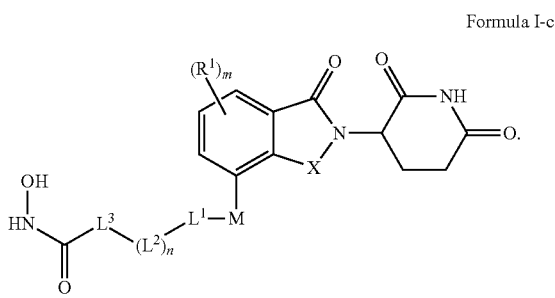

Formula I-c

In some embodiments, M is OC$_{1-3}$alkylene, NH, or NR$^a$, L$^1$ is optionally substituted phenyl, R$^a$ in each instance is independently H or C$_{1-4}$alkyl. In some embodiments, M is OC$_{1-3}$alkylene, NH, or NR$^a$, L$^1$ is optionally substituted phenyl, (L$^2$)n comprises 6-membered heterocyclic, R$^a$ in each instance is independently H or C$_{1-4}$alkyl.

In some embodiments, the compound of Formula I is represented by Formula I-d

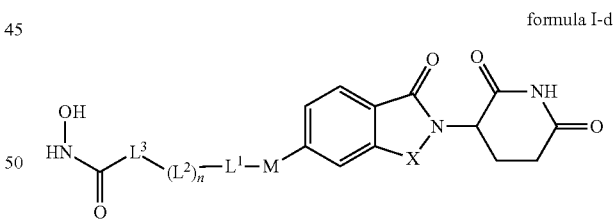

formula I-d

In some embodiments, M is OC$_{1-3}$alkylene, NH, or NR$^a$, L$^1$ is optionally substituted phenyl, R$^a$ in each instance is independently H or C$_{1-4}$alkyl. In some embodiments, M is OC$_{1-3}$alkylene, NH, or NR$^a$, L$^1$ is optionally substituted phenyl, (L$^2$)n comprises 6-membered heterocyclic, R$^a$ in each instance is independently H or C$_{1-4}$alkyl.

In some embodiments, the compound is represented by Formula I-e. The scope of the substituents R$^{1a}$, R$^{1b}$, and R$^{1c}$ is as defined above for R$^1$. Subscript p is an integer of 0 to 15. R$^3$ and R$^{3'}$ are independently H, F, Cl or Me. Alternatively, one of R$^3$ and R$^{3'}$ is H, F, or Cl, and the other is CF2, CF3, or Me. In some embodiments, both of R$^3$ and R$^{3'}$ are H.

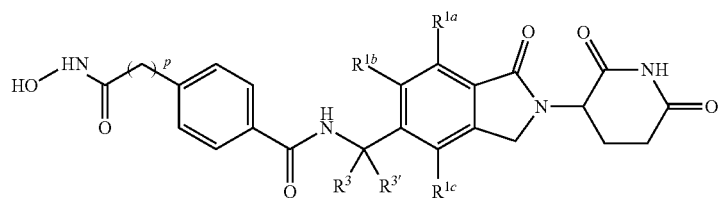

Formula I-e

Nonlimiting examples of compounds of I-e include the following ($R^3$ and $R^{3'}$=H)

TABLE 1

| Compound | p | $R^{1a}$ | $R^{1b}$ | $R^{1c}$ |
|---|---|---|---|---|
| 1 | 1, 2, 3, 4, 5, 6, 7, 8, 9, 10, 11, or 12 | H | H | H |
| 13 | 1, 2, 3, 4, 5, 6, 7, 8, 9, 10, 11, or 12 | CF3 | H | H |
| 25 | 1, 2, 3, 4, 5, 6, 7, 8, 9, 10, 11, or 12 | F | H | H |
| 37 | 1, 2, 3, 4, 5, 6, 7, 8, 9, 10, 11, or 12 | OMe | H | H |
| 49 | 1, 2, 3, 4, 5, 6, 7, 8, 9, 10, 11, or 12 | Cl | H | H |
| 61 | 1, 2, 3, 4, 5, 6, 7, 8, 9, 10, 11, or 12 | Cyclopropyl | H | H |
| 73 | 1, 2, 3, 4, 5, 6, 7, 8, 9, 10, 11, or 12 | CF3 | H | H |
| 85 | 1, 2, 3, 4, 5, 6, 7, 8, 9, 10, 11, or 12 | F | H | H |
| 97 | 1, 2, 3, 4, 5, 6, 7, 8, 9, 10, 11, or 12 | OMe | H | H |
| 119 | 1, 2, 3, 4, 5, 6, 7, 8, 9, 10, 11, or 12 | Cl | H | H |
| 131 | 1, 2, 3, 4, 5, 6, 7, 8, 9, 10, 11, or 12 | Cyclopropyl | H | H |

In some embodiments, the compound is represented by formula I-f, wherein n is 1, 2, 3, 4, 5, 6, 7, 8, 9, 10, 11, or 12. $R^3$ and $R^{3'}$ are independently H, F, Cl or Me. Alternatively, one of $R^3$ and $R^{3'}$ is H, F, or Cl, and the other is CF2, CF3, or Me.

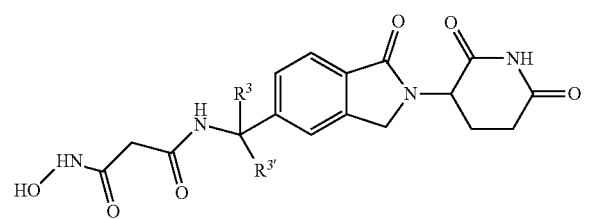

Formula I-f

In some embodiments, the compound is represented by the formula I-g, wherein p is 1, 2, 3, 4, 5, 6, 7, 8, 9, 10, 11, or 12.

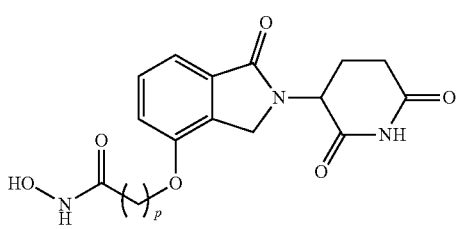

Formula I-g

In some embodiments, the compound is represented by the formula I-h, wherein p is 1, 2, 3, 4, 5, 6, 7, 8, 9, 10, 11, or 12.

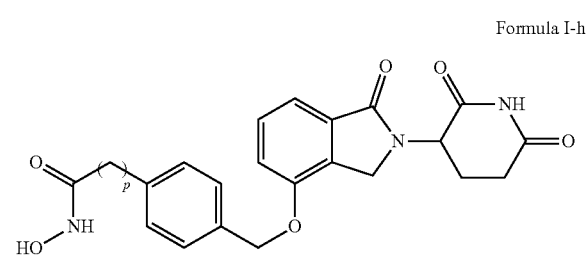

Formula I-h

In some embodiments, the compound is represented by formula I-i, wherein p is 1, 2, 3, 4, 5, 6, 7, 8, 9, 10, 11, or 12.

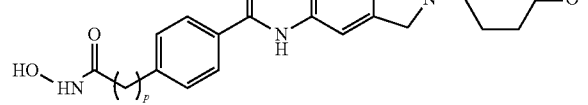

Formula I-i

In some embodiments, the compound is represented by Formula I-j,

Formula I-j

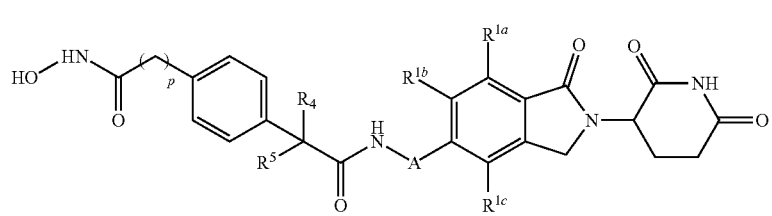

Wherein:
p is an integer from 1 to 20,
A is $C_{1-2}$alkylene or void,
$R^{1a}$, $R^{1b}$, and $R^{1c}$ in each instance are independently selected from the group consisting of 3-6 membered cycloalkyl, 3-6 membered heterocycloalkyl, $C_{1-4}$alkyl, $OC_{1-4}$alkyl, $NR^aR^b$, halo $C_{1-4}$alkyl, halogen, OH, and CN; and
$R^4$ and $R^5$, are each independently H, halogen (e.g. F, Cl) or $C_{1-4}$alkyl.

In some embodiments. $R^4$ and $R^5$ are each independently H or halogen. In some embodiments, $R^{1a}$ is selected from the group consisting of 3-6 membered cycloalkyl, $C_{1-4}$alkyl, $OC_{1-4}$alkyl, halo $C_{1-4}$alkyl, and halogen. In some embodiments, A is $C_{1-2}$alkylene, wherein M is NHC(O) and the nitrogen of M is bonded to A.

In some embodiments, Formula I-j is represented as the following formula I-j', wherein the scope of the substituents $R^{1a}$, $R^{1b}$, and $R^{1c}$ is as defined above, $R^3$ and $R^{3'}$ re independently H, F, Cl or Me. Alternatively, one of $R^3$ and $R^{3'}$ is H, F, or Cl, and the other is CF2, CF3, or Me. In some embodiments, both of $R^3$ and $R^{3'}$ are H.

Formula I-j'

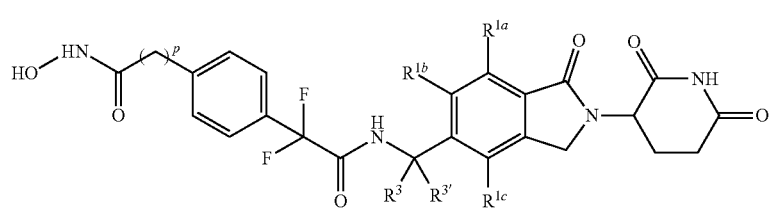

Nonlimiting examples of compounds of Formula I-j' include the following ($R^3$ and $R^{3'}$ are H),

| Compound | p | $R^{1a}$ | $R^{1b}$ | $R^{1c}$ |
|---|---|---|---|---|
| 251 | 1, 2, 3, 4, or 5 | H | H | H |
| 256 | 6 | H | H | H |
| 257 | 7 | H | H | H |
| 258 | 8, 9, 10, 11, or 12 | H | H | H |
| 263 | 1, 2, 3, 4, 5, 6, 7, 8, 9, 10, 11, or 12 | CF3 | H | H |
| 275 | 1, 2, 3, 4, 5, 6, 7, 8, 9, 10, 11, or 12 | F | H | H |
| 287 | 1, 2, 3, 4, 5, 6, 7, 8, 9, 10, 11, or 12 | OMe | H | H |
| 299 | 1, 2, 3, 4, 5, 6, 7, 8, 9, 10, 11, or 12 | Cl | H | H |

-continued

| Compound | p | $R^{1a}$ | $R^{1b}$ | $R^{1c}$ |
|---|---|---|---|---|
| 311 | 1, 2, 3, 4, 5, 6, 7, 8, 9, 10, 11, or 12 | Cyclopropyl | H | H |
| 323 | 1, 2, 3, 4, 5, 6, 7, 8, 9, 10, 11, or 12 | CF3 | H | H |
| 335 | 1, 2, 3, 4, 5, 6, 7, 8, 9, 10, 11, or 12 | F | H | H |
| 347 | 1, 2, 3, 4, 5, 6, 7, 8, 9, 10, 11, or 12 | OMe | H | H |
| 359 | 1, 2, 3, 4, 5, 6, 7, 8, 9, 10, 11, or 12 | Cl | H | H |
| 371 | 1, 2, 3, 4, 5, 6, 7, 8, 9, 10, 11, or 12 | Cyclopropyl | H | H |

-continued

| Compound | p | $R^{1a}$ | $R^{1b}$ | $R^{1c}$ |
|---|---|---|---|---|
| 383 | 1, 2, 3, 4, 5, 6, 7, 8, 9, 10, 11, or 12 | CF3 | H | H |
| 395 | 1, 2, 3, 4, 5, 6, 7, 8, 9, 10, 11, or 12 | F | H | H |
| 407 | 1, 2, 3, 4, 5, 6, 7, 8, 9, 10, 11, or 12 | OMe | H | H |
| 419 | 1, 2, 3, 4, 5, 6, 7, 8, 9, 10, 11, or 12 | Cl | H | H |

In some embodiments, the compound is represented by Formula I-k,

Formula I-k

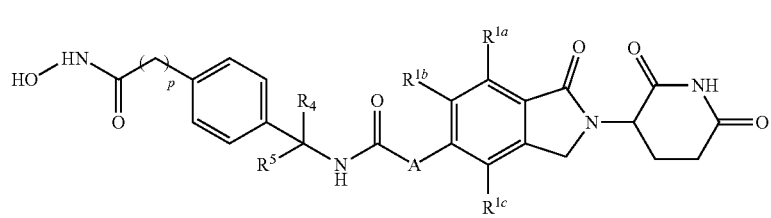

Wherein
p is an integer from 1 to 20,
A is $C_{1-2}$alkylene or void,
$R^{1a}$, $R^{1b}$, and $R^{1c}$ in each instance are independently selected from the group consisting of 3-6 membered cycloalkyl, 3-6 membered heterocycloalkyl, $C_{1-4}$alkyl, $OC_{1-4}$alkyl, $NR^aR^b$, halo $C_{1-4}$alkyl, halogen, OH, and CN;
$R^4$ and $R^5$, are each independently H, halogen (e.g. F, Cl) or $C_{1-4}$alkyl.

In some embodiments, A is void. In some embodiments, the nitrogen of NHC(O)NH, O(CO)NH, NHC(O)O or NHC(O) in M is bonded to $L^1$.

In some embodiments, $R^4$ and $R^5$ are each independently H or halogen. In some embodiments, $R^{1a}$ is selected from the group consisting of 3-6 membered cycloalkyl, $C_{1-4}$alkyl, $OC_{1-4}$alkyl, halo $C_{1-4}$alkyl, and halogen. In some embodiments, one or both of $R^{1b}$ and $R^{1c}$ are H.

Nonlimiting examples of compounds under Formula I-k include the following (p is 1, 2, 3, 4, 5, 6, 7, 8, 9, 10, 11, 12, 13, 14, or 15; A is void):

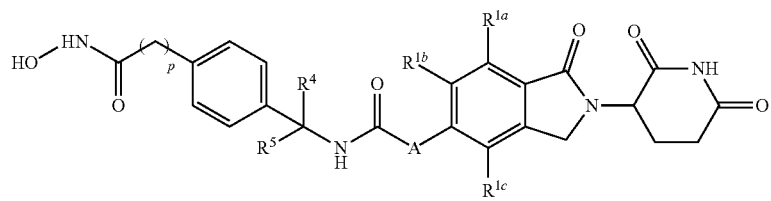

| Compound | $R^{1a}$ | $R^{1b}$ | $R^{1c}$ | $R^4$ | $R^5$ |
|---|---|---|---|---|---|
| 443 | H | H | H | H | H |
| 459 | H | H | H | H | F |
| 475 | H | H | H | F | F |
| 491 | CF3 | H | H | H | H |
| 507 | F | H | H | H | H |
| 523 | OMe | H | H | H | H |
| 539 | Cl | H | H | H | H |
| 555 | Cyclopropyl | H | H | H | H |
| 571 | CF3 | H | H | H | F |
| 587 | F | H | H | H | F |
| 603 | OMe | H | H | H | F |
| 619 | Cl | H | H | H | F |
| 635 | Cyclopropyl | H | H | H | F |
| 651 | CF3 | H | H | F | F |
| 667 | F | H | H | F | F |
| 683 | OMe | H | H | F | F |
| 699 | Cl | H | H | F | F |
| 715 | Cyclopropyl | H | H | F | F |
| 731 | CF3 | H | H | H | H |
| 747 | F | H | H | H | H |
| 763 | OMe | H | H | H | H |
| 779 | Cl | H | H | H | H |
| 795 | Cyclopropyl | H | H | H | H |
| 811 | CF3 | H | H | H | F |
| 827 | F | H | H | H | F |
| 843 | OMe | H | H | H | F |
| 859 | Cl | H | H | H | F |
| 875 | Cyclopropyl | H | H | H | F |
| 891 | CF3 | H | H | F | F |
| 907 | F | H | H | F | F |
| 923 | OMe | H | H | F | F |
| 939 | Cl | H | H | F | F |
| 955 | Cyclopropyl | H | H | F | F |
| 971 | CF3 | H | H | H | H |
| 987 | F | H | H | H | H |
| 1003 | OMe | H | H | H | H |
| 1019 | Cl | H | H | H | H |
| 1035 | Cyclopropyl | H | H | H | H |
| 1051 | CF3 | H | H | H | F |
| 1067 | F | H | H | H | F |
| 1083 | OMe | H | H | H | F |
| 1099 | Cl | H | H | H | F |
| 1115 | Cyclopropyl | H | H | H | F |
| 1131 | CF3 | H | H | F | F |
| 1147 | F | H | H | F | F |
| 1163 | OMe | H | H | F | F |
| 1179 | Cl | H | H | F | F |
| 1195 | Cyclopropyl | H | H | F | F |

In some embodiments, the compound is selected from the following:
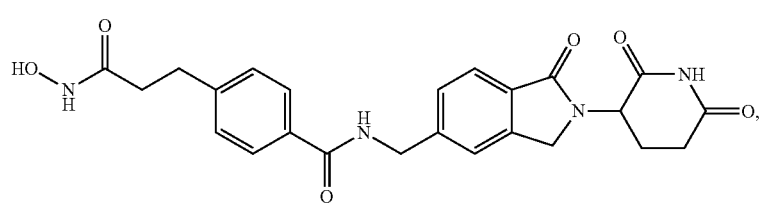
compound 2
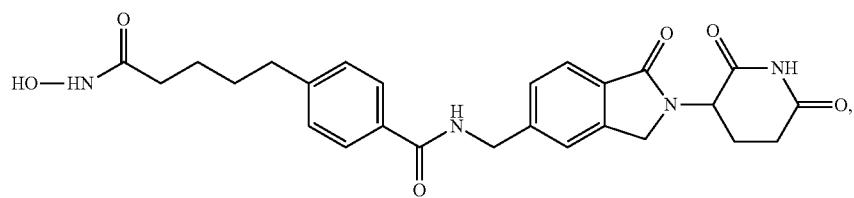
compound 4
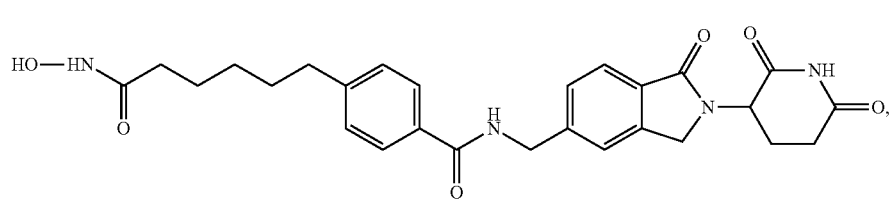
compound 5
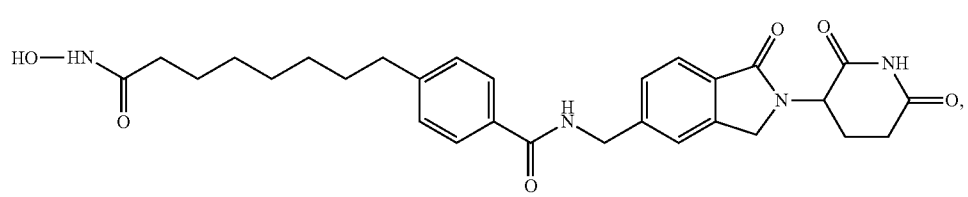
compound 7
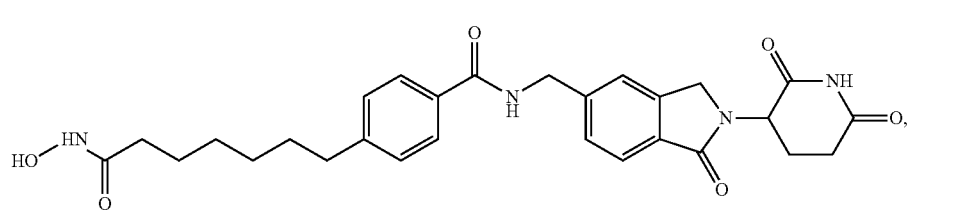
Compound 6
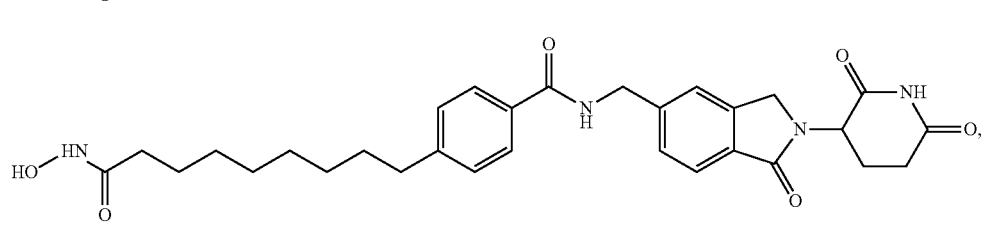
Compound 8
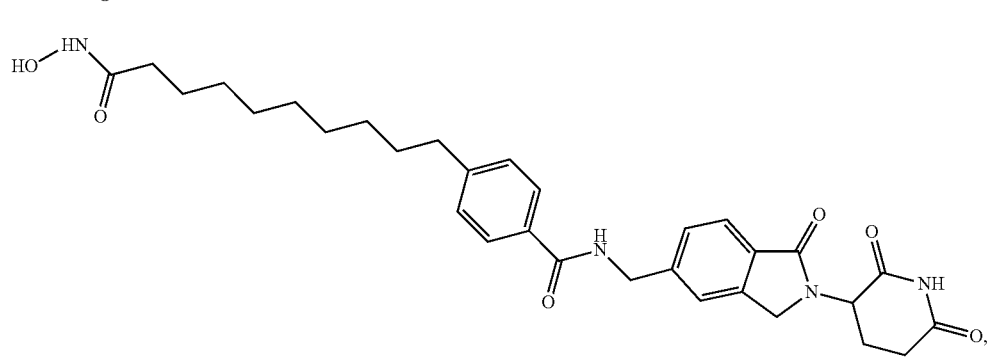
Compound 9

-continued
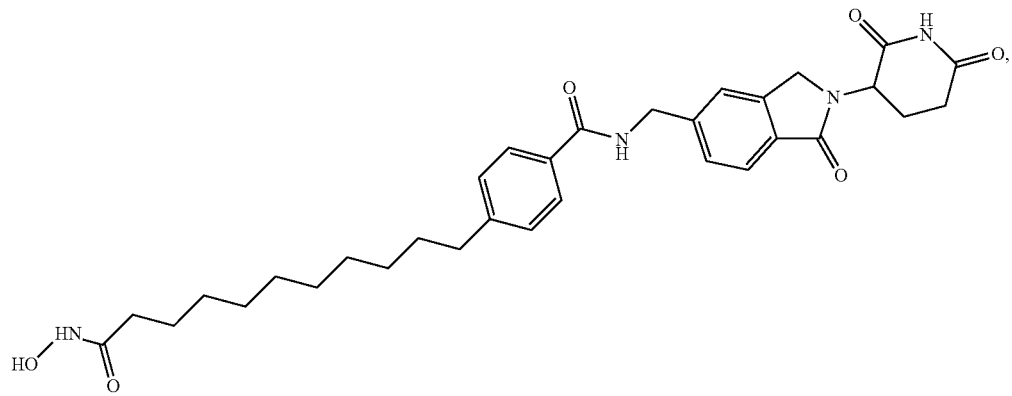
Compound 10
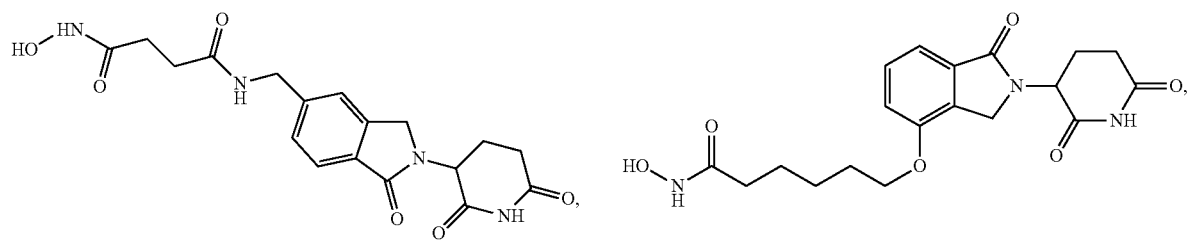
compound 204
compound 219
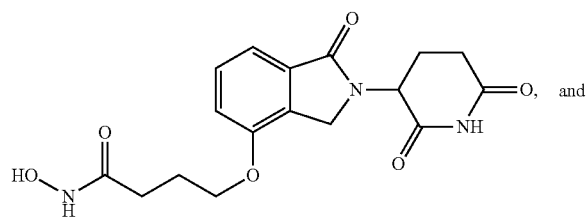
compound 217
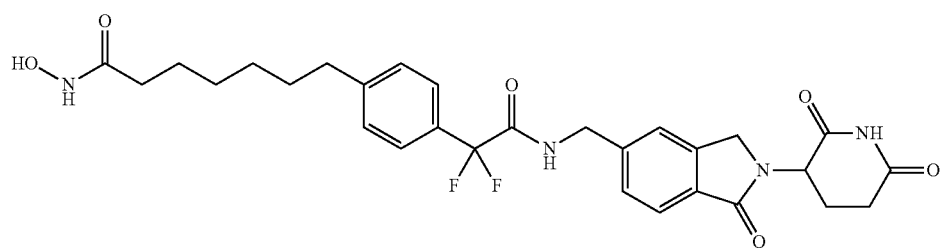
compound 256
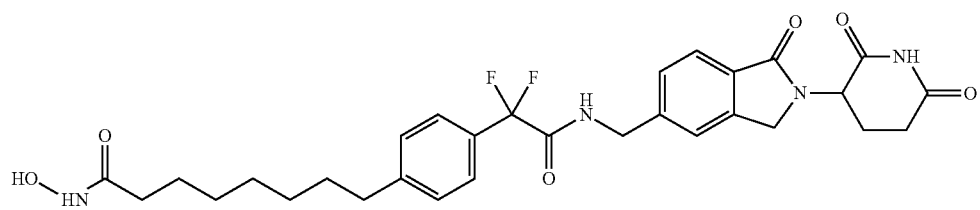
compound 257
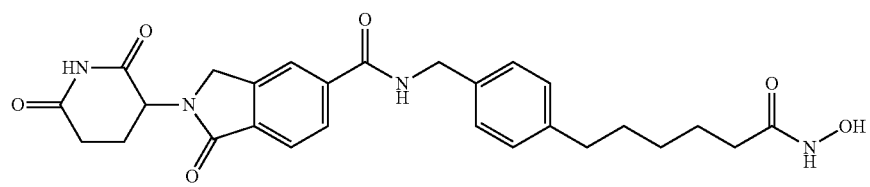
compound 448

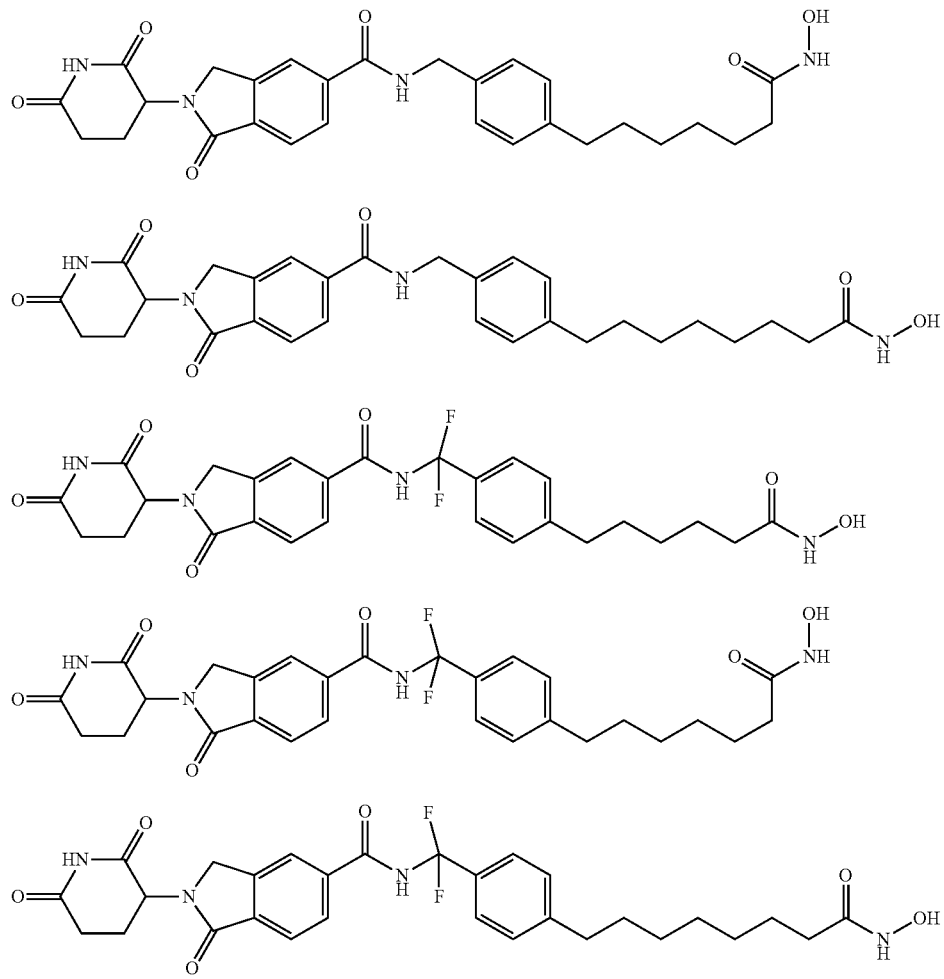

compound 449 compound 450 compound 479 compound 480 compound 481

Another aspect of the present disclosure provides a pharmaceutical composition containing a therapeutically effective amount of the above-described compound and a pharmaceutically acceptable carrier.

The pharmaceutical composition may also contain one or more physiologically acceptable surface-active agents, additional carriers, diluents, excipients, smoothing agents, suspension agents, film forming substances, and coating assistants, or a combination thereof; and a composition disclosed herein. Acceptable additional carriers or diluents for therapeutic use are well known in the pharmaceutical art, and are described, for example, in Remington's Pharmaceutical Sciences, 18th Ed., Mack Publishing Co., Easton, PA (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid, and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, microcrystalline cellulose, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The pharmaceutical compounds described herein can be administered to a human patient per se, or in pharmaceutical compositions where they are mixed with other active ingredient(s), as in combination therapy, or suitable carriers or excipient(s). In some embodiments, a dosage form includes those forms in which the compound is administered per se. In addition, a dosage form may include a pharmaceutical composition. In any case, the dosage form may comprise a sufficient amount of the compound to treat a disease as part of a particular administration protocol, as would be understood by those of skill in the art. Techniques for formulation and administration of the compounds of the instant application may be found in "Remington's Pharmaceutical Sciences," Mack Publishing Co., Easton, PA, 18th edition, 1990.

The pharmaceutical compositions may be manufactured in a manner that is itself known, e.g., by means of conventional mixing, dissolving, granulating, levigating, emulsifying, encapsulating, entrapping or tableting processes.

Pharmaceutical compositions may be formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, diluents, carriers, and excipients may be used as suitable and as understood in the art; e.g., in Remington's Pharmaceutical Sciences, above.

Another aspect of this disclosure provides a method of treating a disease in a subject. The method includes administering to the subject in need a therapeutically effective amount of a compound of Formula I or a pharmaceutically acceptable salt, isomer, or pharmaceutical composition thereof. Specific embodiments of the compound of Formula I are as described above.

The pleiotropic pathway modifier (PPM) discovered herein exhibit therapeutic activities against various diseases. Nonlimiting examples of diseases which may be treated using compounds disclosed herein include, for example, various cancers, and autoimmune diseases and many chronic inflammatory diseases, such as multiple sclerosis, psoriasis, rheumatoid arthritis, sarcoidosis, lupus, asthma, metabolic syndrome, among others.

The term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers that may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuro-epithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present invention include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

In some embodiments, the disease is bladder cancer, breast cancer, colorectal adenocarcinoma, hepatoma, ovarian cancer, pancreatic cancer, prostate cancer, blood cancer, leukemia, lymphoma, or myeloma. In some embodiments, the disease is other types of solid tumor.

The compound of Formula I or a pharmaceutical composition thereof may also be used in combination with or include one or more other therapeutic agents, for example selected from NSAIDS, corticosteroids, COX-2 inhibitors, cytokine inhibitors, anti-TNF agents, inhibitors oncostatin M, antimalarials, immunosuppressive and cytostatics.

The compound of compound of formula (I) or a pharmaceutically acceptable salt thereof may also be employed with other therapeutic methods of cancer treatment. In particular, in antineoplastic therapy, combination therapy with other chemotherapeutic, hormonal, antibody agents as well as surgical and/or radiation treatments other than those mentioned above are envisaged. As indicated, therapeutically effective amounts of the compound of compound of formula (I) or a pharmaceutically acceptable salt thereof are discussed above. The therapeutically effective amount of the further therapeutic agents of the present invention will depend upon several factors including, for example, the age and weight of the mammal, the precise condition requiring treatment, the severity of the condition, the nature of the formulation, and the route of administration. Ultimately, the therapeutically effective amount will be at the discretion of the attendant physician or veterinarian. The relative timings of administration will be selected to achieve the desired combined therapeutic effect. In one embodiment, the further anti-cancer therapy is surgical and/or radiotherapy.

In some embodiments, the methods disclosed herein further including administering to the subject one, two, three or more of the anticancer agents or therapies including surgery, chemotherapy, radiation therapy, hormone therapy, cellular therapy, biologics, immunotherapy, HER2 targeted therapy, or curative-intent radiotherapy for the treatment of the cancer. Examples of anticancer agents or therapies for use in combination with the compound of Formula I or its pharmaceutically acceptable salt thereof are shown below.

Nonlimiting examples of secondary agents include immunomodulating agents (lenalidomide, pomalidomide, and other IMiDs, etc), inhibitors of proteosome (e.g. bortezomib, carfilzomib), microtubule (e.g. paclitaxel), DNA topoisomerase (e.g. cisplatin), mammalian target of rapamycin (mTOR) (e.g. everolimus, sapanisertib) and tyrosine kinases (flavopiridol, ibrutinib, erlotinib); DNA damaging agents (e.g. cisplatin, doxorubicin, topotecan, etoposide), immune checkpoint blockers (e.g. nivolumab, ipilimumab, pembrolizumab), alkylate agents (e.g. bendamustine, melphalan), antibodies (e.g., durvalumab, avelumab, atezolizumab, rituximab, etc).

Non-limiting examples of HER2-targeted agents include trastuzumab, pertuzumab, lapatinib, neratinib, SYD985 and trastuzumab emtansine (T-DM1), and antibody-drug conjugate thereof (e.g. Trasturumab duocannazine).

Non-limiting examples of checkpoint inhibitors include those that target PD-1, PD-L1. CTLA4 and TIGIT (T cell immunoglobulin and ITIM domain). Further examples include Ipilimumab (Yervoy®; blocking a checkpoint protein called CTLA-4); pembrolizunmab (Keytruda®), Cemiplimab (Libtayo) and nivolumab (Opdivo®) (targeting another checkpoint protein called PD-1); atezolizumab (Tecentriq®), Avelumab (Bavencio), and Durvalumab (Imfinzi) (targeting PD-L1); MK-7684, Etigilimab/OMP-313 M32, Tiragolumab/MTIG7192A/RG-6058, BMS-986207, AB-154 and ASP-8374 (targeting TIGIT), and V-domain Ig suppressor of T cell activation (VISTA).

Non-limiting examples of tyrosine kinase inhibitors as chemotherapy include erlotinib, gefitinib, afatinib, dacomitinib and osimertinib.

Further non-limiting examples of the chemthrapy include alkylating agents: Busulfan, dacarbazine, ifosfamide, hexamethylmelamine, thiotepa, dacarbazine, lomustine, chlorambucil, procarbazine, altretamine, estramustine phosphate, mechlorethamine, streptozocin, temozolomide. Semustine cyclophosphamide;

- platinum agents: spiroplatin, tetraplatin, ormaplatin, iproplatin, ZD-0473 (AnorMED), oxaliplatin carboplatin, lobaplatin (Aeterna), satraplatin (Johnson Matthey), BBR-3464 (Hoffmann-La Roche), SM-11355 (Sumitomo), AP-5280 (Access), cisplatin, arboplatin, cisplatin, satraplatin, oxaliplatin, nedaplatin, triplatin tetranitrate, temozolomide, procarbazin; antimetabolites: azacytidine, Floxuridine, 2-chlorodeoxyadenosine, 6-mercaptopurine, 6-thioguanine, cytarabine, 2-fluorodeoxy cylidine, methotrexate, tomudex, fludarabine, raltitrexed, trimetrexate, deoxycoformycin, pentostatin, hydroxyurea, decitabine (SuperGen), clofarabine (Bioenvision), irofulven (MGI Pharma), DMDC (Hoffmann-La Roche), ethynylcytidine (Taiho), gemcitabine, capecitabine;
- topoisomerase inhibitors: amsacrine, epirubicin, etoposide, teniposide or mitoxantrone, 7-ethyl-10-hydroxy-camptothecin, dexrazoxanet (TopoTarget), pixantrone (Novuspharma), rebeccamycin analogue (Exelixis), BBR-3576 (Novuspharma), rubitecan (SuperGen), irinotecan (CPT-11), topotecan;
- antitumor antibiotics: valrubicin, therarubicin, idarubicin, rubidazone, plicamycin, porfiromycin mitoxantrone (novantrone), amonafide, azonafide, anthrapyrazole, oxantrazole, losoxantrone, MEN-10755 (Menarini), GPX-100 (Gem Pharmaceuticals), Epirubicin, mitoxantrone, doxorubicin;
- antimitotic agents: colchicine, vinblastine, vindesine, dolastatin 10 (NCI), rhizoxin (Fujisawa), mivobulin (Warner-Lambert), cemadotin (BASF), RPR 109881A (Aventis), TXD 258 (Aventis), epothilone B (Novartis), T 900607 (Tularik), T 138067 (Tularik), cryptophycin 52 (Eli Lilly), vinflunine (Fabre), auristatin PE (Teikoku Hormone), BMS 247550 (BMS), BMS 184476 (BMS), BMS 188797 (BMS), taxoprexin (Protarga), SB 408075 (GlaxoSmithKline), Vinorelbine, Trichostatin A. E7010 (Abbott), PG-TXL (Cell Therapeutics), IDN 5109 (Bayer), A 105972 (Abbott), A 204197 (Abbott), LU 223651 (BASF), D 24851 (ASTAMedica), ER-86526 (Eisai), combretastatin A4 (BMS), isohomohalichondrin-B (PharmaMar), ZD 6126 (AstraZeneca), AZ10992 (Asahi), IDN-5109 (Indena), AVLB (Prescient NeuroPharma), azaepothilone B (BMS), BNP-7787 (BioNwnerik), CA-4 prodrug (OXiGENE), dolastatin-10 (NIH), CA-4 (OXiGENE), docetaxel, vincristine, paclitaxel;
- aromatase inhibitors: aminoglutethimide, atamestane (BioMedicines), letrozole, anastrazole, YM-511 (Yamanouchi), formestane, exemestane;
- thymidylate synthase inhibitors: pemetrexed (Eli Lilly), ZD-9331 (BTG), nolatrexed (Eximias), Cofactor™ (BioKeys);
- DNA antagonists: trabectedin (PharmaMar); glufosfamide (Baxter International), albumin+32P (isotope Solutions), thymectacin (NewBiotics), edotreotide (Novartis), mafosfamide (Baxter International), apaziquone (Spectrum Pharmaceuticals), 06 benzyl guanine (Paligent); farnesyltransferase inhibitors: arglabin (NuOncology Labs), lonafarnib (Schering-Plough), BAY-43-9006 (Bayer), tipifamib (Johnson & Johnson), perillyl alcohol (DOR BioPharna); pump inhibitors: CBT-1 (CBA Pharma), tariquidar (Xenova), MS-209 (Schering AG), zosuquidar trihydrochloride (Eli Lilly), biricodar dicitrate (Vertex);
- histone acetyltransferase inhibitors: tacedinaline (Pfizer), SAHA (Aton Pharma), MS-275 (Schering AG), pivaloyloxymethyl butyrate (Titan), depsipeptide (Fujisawa);
- metalloproteinase inhibitors: Neovastat (Aeterna Laboratories), marimastat (British Biotech), CMT-3 (CollaGenex), BMS-275291 (Celitech);
- ribonucleoside reductase inhibitors: gallium maltolate (Titan), triapine (Vion), tezacitabine (Aventis), didox (Molecules for Health);
- TNF-alpha agonists/antagonists: virulizin (Lorns Therapeutics), CDC-394 (Celgene), revlimid (Celgene);
- endothelin a receptor antagonist: atrasentan (Abbott), ZD-4054 (AstraZeneca), YM-598 (Yamanouchi);
- retinoic acid receptor agonists: fenretinide (Johnson & Johnson), LGD-1550 (Ligand), alitretinoin (Ligand);
- immunomodulators: Pembrolizumab (formerly lambrolizumab, brand name Keytruda): interferon, oncophage (Antigenics), GMK (Progenics), adenocarcinoma, vaccine (Biomira), CTP-37 (AVI BioPharma), IRX-2 (Immuno-Rx), PEP-005 (Peplin Biotech), synchrovax vaccines (CTL Immuno), melanoma vaccine (CTL Immuno), p21 RAS vaccine (GemVax), MAGE-A3 (GSK), nivolumab (BMS), abatacept (BMS), dexosome therapy (Anosys), pentrix (Australian Cancer Technology), ISF-154 (Tragen), cancer vaccine (Intercell), norelin (Biostar), BLP-25 (Biomira), MGV (Progenics), B-alethine (Dovetail), CLL therapy (Vasogen), Ipilimumab (BMS), CM-10 (cCam Biotherapeutics), MPDL3280A (Genentech);
- hormonal and antihormonal agents: estrogens, conjugated estrogens, ethinyl estradiol, chlortrianisen, idenestrol, hydroxyprogesterone caproate, medroxyprogesterone, testosterone, testosterone propionate, fluoxymesterone, methyltestosterone, diethylstilbestrol, megestrol, bicalutamide, flutamide, nilutamide, dexamethasone, prednisone, methylprednisolone, prednisolone, aminoglutethimide, leuprolide, octreotide, mitotane, P-04 (Novogen), 2-methoxyestradiol (EntreMed), arzoxifene (Eli Lilly), tamoxifen, toremofine, goserelin, Leuporelin, bicalutamide;
- photodynamic agents: talaporfin (Light Sciences), Theralux (Theratechnologies), motexafin gadolinium (Pharmacyclics), Pd-bacteriopheophorbide (Yeda), lutetium texaphyrin (Pharmacyclics), hypericin; and
- kinase inhibitors: afatinib, osimertinib, poziotinib (Spectrum), imatinib (Novartis), leflunomide (Sugen/Pharmacia), ZD1839 (AstraZeneca), erlotinib (Oncogene Science), canertinib (Pfizer), squalamine (Genaera), SU5416 (Pharmacia), SU6668 (Pharmacia), ZD4190 (AstraZeneca), ZD6474 (AstraZeneca), vatalanib (Novartis), PKI166 (Novartis), GW2016 (GlaxoSmithKline), EKB-509 (Wyeth), trastuzumab (Genentech), OSI-774 (Tarceva™), CI-1033 (Pfizer), SU 11248 (Pharmacia), RH3 (York Medical), Genistein, Radicinol, Met-MAb (Roche), EKB-569 (Wyeth), kahalide F (PharmaMar), CEP-701 (Cephalon), CEP-751 (Cephalon), MLN518 (Millenium), PKC412 (Novartis), Phenoxodiol (Novogen), C225 (lmClone), rhuMab (Genentech), MDX-H210 (Medarex), 2C4 (Genentech), MDX-447 (Medarex), ABX-EGF (Abgenix), IMC-IC11 (imClone), Tyrphostins, Gefitinib (Iressa), PTK787 (Novartis), EMD 7200) (Merck), Emodin, Radicinol, Vemurafenib (B-Raf enzyme inhibitor, Daiichi Sankyo), SR-27897 (CCK A inhibitor, Sanofi-Synthelabo), tocladesine (cyclic AMP agonist, Ribapharm), alvocidib (CDK inhibitor, Aventis), CV-247 (COX-2 inhibitor, Ivy Medical), P54 (COX-2 inhibitor, Phytopharm), CapCell™ (CYP450 stimulant, Bavarian Nordic), GCS-100 (gal3 antagonist, GlycoGenesys), G17DT immunogen (gastrin inhibitor, Aphton), efaproxiral (oxygenator, Allos Therapeutics), PI-88 (heparanase inhibitor, Progen), tesmilifene (histamine antagonist, YM BioSciences), histamine (histamine H2 receptor agonist, Maxim), tiazofurin (IMPDH inhibitor, Ribapharm), cilengitide (integrin antagonist, Merck KGaA), SR-31747 (IL-1 antagonist, Sanofi-Synthelabo), CCI-779 (mTOR kinase inhibitor, Wyeth), exisulind (PDE V inhibitor, Cell Pathways). CP-461 (PDE V inhibitor, Cell Pathways), AG-2037 (GART inhibitor, Pfizer), WX-UK) (plasminogen activator inhibitor, Wilex), PBI-1402 (PMN stimulant, ProMetic LifeSciences), bortezomib (proteasome inhibitor, Millennium), SRL-172 (T cell stimulant, SR Pharma), TLK-286 (glutathione S transferase inhibitor, Telik), PT-100 (growth factor agonist, Point Therapeutics), midostaurin (PKC inhibitor, Novartis), bryostatin-1 (PKC stimulant, GPC Biotech), CDA-11 (apoptosis promotor, Everlife), SDX-101 (apoptosis promotor. Salmedix), rituximab (CD20 antibody, Genentech, carmustine, Mitoxantrone, Bleomycin, Absinthin, Chrysophanic acid, Cesium oxides, BRAF inhibitors, PDL1 inhibitors, MEK inhibitors, bevacizumab, angiogenesis inhibitors, dabrafenib, ceflatonin (apoptosis promotor, ChemGenex); BCX-1777 (PNP inhibitor, BioCryst), ranpirnase (ribonuclease stimulant, Alfacell), galarubicin (RNA synthesis inhibitor, Dong-A), tirapazamine (reducing agent, SRI International), N, acetylcysteine (reducing agent, Zambon), R-flurbiprofen (NFκB inhibitor, Encore), 3CPA (NF-kappaB inhibitor, Active Biotech), seocalcitol (vitamin D receptor agonist, Leo), 131-I-TM-601 (DNA antagonist. TransMolecular), eflonithine (ODC inhibitor, ILEX Oncology), minodronic acid (osteoclast inhibitor, Yamanouchi), indisulam (p53 stimulant, Eisai), aplidine (PPT inhibitor, PharmaMar), gemtuzumnab (CD33 antibody, Wyeth Ayerst), PG2 (hematopoiesis enhancer, Pharmagenesis), Immunoli (triclosan oral rinse, Endo), triacetyluridine (uridine prodrug, Wellstat), SN-4071 (sarcoma agent, Signature BioScience), TransMID-107™ (immunotoxin, KS Biomedix), PCK-3145 (apoptosis promotor, Procyon), doranidazole (apoptosis promotor, Pola), CHS-828 (cytotoxic agent, Leo), trans-retinoic acid (differentiator, NIH), MX6 (apoptosis promotor, MAXIA), apomine (apoptosis promotor, ILEX Oncology), urocidin (apoptosis promotor, Bioniche), Ro-31-7453 (apoptosis promotor, La Roche), brostallicin (apoptosis promotor, Pharmacia), β-lapachone, gelonin, cafestol, kahweol, caffeic acid, Tyrphostin AG, PD-1 inhibitors, CTLA-4 inhibitors, sorafenib, BRAF inhibitors, mTOR inhibitors (e.g. Vistusertib, everolimus/Afinitor, rapamycin, dactolisib, BGT226, SF1126, PKI-587, NVPBE235) and Pan-HER inhibitor (e.g. afatinib, neratinb, AC480).

In some embodiments, the agent for chemotherapy is selected from bevacizurnab, bortezomib, capecitabine, cetuximab, fluorouracil, imatinib, irinotecan, leucovorin, oxaliplatin, panitumumab, pemetrexed, temozolomide, cisplatin, paclitaxel, erlotinib, sunitinib, lapatinib, sorafenib, carboplatin, doxorubicin, docetaxel, gemcitabine, etoposide, gefitinib, PD153035, cetuximab, bevacizumab, panitumumab, trastuzumab, anti-c-Met antibodies, gefitinib, ZD6474, EMD-72000, pariitumab, ICR-62, CI-1033, lapatinib, AEE788, EKB-569. EXEL 7647/EXEL 0999, erlotinib, imatinib, sorafinib, sunitinib, dasatinib, vandetinib, temsirolimus, PTK787, pazopanib, AZD2171, everolimus, seliciclib, AMG 706, axitinib, PD0325901, PKC-412, CEP701, XL880, bosutinib, BIBF1120, BTBF1120, nilotinib, AZD6244, HKIT-272, MS-275, B12536, GX15-070, AZD0530, enzastaurin, MLN-518, ARQ197, CM101, IFN-.alpha., IL-12, platelet factor-4, suramin, SU5416, thrombospondin, VEGFR antagonists, angiostatic steroids plus heparin, Cartilage-Derived Angiogenesis Inhibitory Factor, matrix metalloproteinase inhibitors, batimastat, marimastat, angiostatin, endostatin, 2-medhoxyestradiol, tecogalan, thrombospondin, .alpha.V.beta.3 inhibitors, linomide, and ADH-1, chlorambucil, cyclophosphamide, ifosfamide, mechlorethamine, melphalan, uracil mustard, thiotepa, busulfan, carmustine, lomustine, streptozocin, carboplatin, cisplatin, satraplatin, oxaliplatin, altretamine, ET-743, XL119, dacarbazine, chlormethine, bendamustine, trofosfamide, uramustine, fotemustine, nimustine, prednimustine, ranimustine, semustine, nedaplatin, triplatin tetranitrate, mannosulfan, treosulfan, temozolomide, carboquone, triaziquone, triethylenemelamine, procarbazin, doxorubicin, daunorubicin, epirubicin, idarubicin, anthracenedione, mitoxantrone, mitomycin C, bleomycin, dactinomycin, plicatomycin, irinotecan, camptothecin, rubitecan, belotecan, etoposide, teniposide, topotecan, paclitaxel, taxol, docetaxel, BMS-275183, xyotax, tocosal, vinorlebine, vincristine, vinblastine, vindesine, vinzolidine, etoposide, teniposide, ixabepilone, larotaxel, ortataxel, tesetaxel, ispinesib, fluorouracil, floxuridine, methotrexate, xeloda, arranon, leucovorin, hydroxyurea, thioguanine, mercaptopurine, cytarabine, pentostatin, fludambine phosphate, cladribine, asparaginase, gemcitabine, pemetrexed, bortezomib, aminopterin, raltitrexed, clofarabine, enocitabine, sapacitabine, azacitidine.

Further examples of agent for chemotherapy include SHP2 inhibitors (e.g. RMC-4550 and RMC-4630), phosphatase inhibitors (e.g. Tautomycin), CDK 4/6 inhibitors (abemaciclib (Lilly), palbociclib (Pfizer)), protein-protein interaction disruptors (BI 1701963), HSP90 inhibitor, tubulin inhibitor, apoptosis inhibitor, chemopreventative agent, and therapies targeting PBK/AKT/mTOR pathway.

Antibody-drug conjugates have emerged as a breakthrough approach to the development of cancer therapeutics. Cancer is one of the leading causes of deaths in the world. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs. ADCE-TRIS® (brentuximab vedotin) in 2011 and KADCYLA4® (trastuzumab emtansine or T-DM1) in 2013 by FDA validated the approach. Another example is Trastuzumab duocarmazine. There are currently more than 30 ADC drug candidates in various stages of clinical trials for cancer treatment. As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

Examples of immunotherapies include immune adjuvants, e.g., *Mycobacterium bovis, Plasmodium falciparum*, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

Further examples of agents for use in combination with the compound of Formula i or its salt include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy. In some embodiments, the agents for use in combination with the compound of Formula I or its salt include one or more of bortezomib, taxol, aromatase inhibitor, and tazemetostat (ezh2 inhibitor).

In some embodiments, the TNF-α, HDAC, IRF4, NFκB or c-MYC overexpression-mediated disease or condition comprises cancer, inflammatory diseases, acute and chronic pain, pruritus, bone-related diseases, neurodegenerative diseases, infectious diseases, and other diseases, including but not limited to neuroblastoma, prostate cancer, pancreatic cancer, melanoma, head and neck cancer, gastric carcinoma, lung carcinoma, liver cancer, uterine cancer, adrenal cancer, biliary tree cancer, intestinal cancer, colorectal cancer, ovarian cancer, lung carcinoma, small cell lung cancer, non-small cell lung cancer, gastric carcinoma, breast cancer, esophageal cancer, urinary bladder cancer, endometrial cancer, brain cancer, low-grade glioma, glioblastoma, medulloblastoma, secretory breast cancer, secretory breast carcinoma, salivary gland cancer, papillary thyroid carcinoma, ductal carcinoma, adult myeloid leukemia, acute myeloid leukemia, large cell neuroendocrine tumors, pulmonary neuroendocrine tumors, sarcomas, pheochromocytoma, librosarcoma, congenital fibrosarcoma, congenital mesoblastic nephroma, secretory breast carcinoma, malignant fibrous histiocytoma, embryonal rhabdomyosarcoma, leiomyoma sarcoma, neuro-fibrosarcoma, neoplasms of the central nervous systems, osteosarcoma, synovial sarcoma, liposarcoma, alveolar soft part sarcoma cancer, Wilms' tumor, lymphomas (e.g. including Hodgkin's lymphoma, lymphoplasmacytic lymphoma, follicular lymphoma, mucosa-associated lymphoid tissue lymphoma, mantle cell lymphoma, B-linage large cell lymphoma, Burkitt's lymphoma, and T-cell anaplastic large cell lymphoma), inflammatory lung diseases (e.g. asthma), inflammatory bowel diseases, (e.g. ulcerative colitis, Crohn's disease), inflammatory skin diseases (e.g. atopic dermatitis, eczema and psoriasis), interstitial cystitis, rhinitis, acute pain, chronic pain, cancer pain, surgical pain, inflammatory pain, neuropathic pain, nociceptive pain, pain of osteoarthritis, chronic low back pain, low back pain of osteoporosis, pain of bone fracture, pain of rheumatoid arthritis, postherpetic pain, pain of diabetic neuropathy, fibromyalgia, pain of pancreatitis, pain of interstitial cystitis, pain of endometriosis, pain of imitable bowel syndrome, migraine, pain of pulpitis, interstitial cystitis pain, painful bladder syndrome, central pain syndromes, postsurgical pain syndromes, bone and joint pain, repetitive motion pain, dental pain, myofascial pain, perioperative pain, dysmenorrhea, myofascial pain, angina pain, headache, primary hyperalgesia, secondary hyperalgesia, primary allodynia, secondary allodynia, other pain caused by central sensitization, systemic cutaneous pruritus, localized cutaneous pruritus, senile cutaneous pruritus, gestational pruritus, pruritus ani, vulvar pruritus us, metastatic bone disease, treatment-induce bone loss, osteoporosis, rheumatoid arthritis, bone metastasis, ankylosing spondylitis, Paget's disease, periodontal disease, osteolytic disease, multiple sclerosis, Parkinson's disease. Alzheimer's disease, Chagas disease, cachexia, anorexia, demyelination and demyelination, malaria, HIV, COVID-19 and other virus infections.

In some embodiments, the TNF-α, HDAC, IRF4, NFκB or c-MYC overexpression-mediated disease is selected from the group of non-small cell lung cancer, colorectal cancer, gastric cancer, liver cancer, invasive breast cancer, lung adenocarcinoma, uterine cancer, adrenal cancer, pancreatic cancer, ovarian cancer, esophageal cancer, urinary bladder cancer, endometrial cancer, prostate cancer, low-grade glioma, glioblastoma, soft tissue sarcoma, papillary thyroid carcinoma, head and neck squamous cell carcinoma, congenital fibrosarcoma, congenital mesoblastic nephroma, secretory breast carcinoma, mammary analogue secretory carcinoma, acute myeloid leukemia, ductal carcinoma, pulmonary neuroendocrine tumors, pheochromocytoma, and Wilms' tumor.

In some embodiments, the TNF-α, HDAC, IRF4, NFκB or c-MYC overexpression-mediated disease is a relapsed cancer or chronic inflammatory disease. In some embodiments, the TNF-α, HDAC, LRF4, NFκB or c-MYC overexpression-mediated disease is refractory to one or more previous treatments.

In some embodiments, the disease or condition is autoimmune. Autoimmune diseases associated with type 1 interferon include, but are not limited to Systemic lupus erythematosus, Psoriasis, insulin-dependent diabetes mellitus (IDDM), dermatomyositis and Sjogren's syndrome (SS).

In some embodiments, the disease or condition is inflammation, which may be inflammation of any tissue and organs of the body, including for example musculoskeletal inflammation, vascular inflammation, neural inflammation, digestive system inflammation, ocular inflammation, inflammation of the reproductive system, and other inflammation, as exemplified below.

The compositions or pharmaceutical compositions described herein may be administered to the subject by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intrasuricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; as well as (d) administration topically; as deemed appropriate by those of skill in the art for bringing the active compound into contact with living tissue.

Pharmaceutical compositions suitable for administration include compositions where the active ingredients are contained in an amount effective to achieve its intended purpose. In some embodiments, a therapeutically effective amount of a compound is an amount effective to treat a viral infection, for example, in a mammalian subject (e.g., a human). The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication, and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved adverse side effects disappear. The dosage may range broadly, depending upon the desired effects and the therapeutic indication. Typically, dosages may be about 10 microgram/kg to about 100 mg/kg body weight, preferably about 100 microgram/kg to about 10 mg/kg body weight. Alternatively, dosages may be based and calculated upon the surface area of the patient, as understood by those of skill in the art.

The exact formulation, route of administration and dosage for the pharmaceutical compositions can be chosen by the individual physician in view of the patient's condition. (see e.g., Fingl et al. 1975, in "The Pharmacological Basis of Therapeutics", which is hereby incorporated herein by reference in its entirety, with particular reference to Ch. 1, p. 1). In some embodiments, the dose range of the composition administered to the patient can be from about 0.5 to about 100M mg/kg of the patient's body weight. The dosage may be a single one or a series of two or more given in the course of one or more days, as is needed by the patient. In instances where human dosages for compounds have been established for at least some conditions, those same dosages, or dosages that are about 0.1% to about 500%, more preferably about 25% to about 250% of the established human dosage may be used. Where no human dosage is established, as will be the case for newly discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of about 0.1 mg to 20(0) mg of the active ingredient, preferably about 1 mg to about 500 mg, e.g. S to 200 mg. In other embodiments, an intravenous, subcutaneous, or intramuscular dose of the active ingredient of about 0.01 mg to about 100 mg, preferably about 0.1 mg to about 60 mg, e.g. about 1 to about 40 mg is used. In cases of administration of a pharmaceutically acceptable salt, dosages may be calculated as the free acid. In some embodiments, the composition is administered 1 to 4 times per day. Alternatively, the compositions may be administered by continuous intravenous infusion, preferably at a dose of up to about 1000 mg per day. As will be understood by those of skill in the art, in certain situations it may be necessary to administer the compounds disclosed herein in amounts that exceed, or even far exceed, the above-stated, preferred dosage range to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety, which are sufficient to maintain the antibiotic effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen, which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered may be dependent on the subject being treated, on the subject's weight, the severity of the infection, the manner of administration and the judgment of the prescribing physician.

Compositions disclosed herein can be evaluated for efficacy and toxicity using known methods. For example, the toxicology of the compound may be established by determining in vow toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound formulated in a compatible pharmaceutical carrier may also be prepared, placed in an appropriate container, and labeled for treatment of an indicated condition.

In some embodiments, in the pharmaceutical industry, it is standard practice to provide substantially pure material when formulating pharmaceutical compositions. Therefore, in some embodiments, "substantially pure" refers to the amount of purity required for formulating pharmaceuticals, which may include, for example, a small amount of other material that will not affect the suitability for pharmaceutical use. In some embodiments, the substantially pure compound contains at least about %% of the compound by weight, such as at least about 97%, 98%, 99%, or 100% of the compound.

Another aspect of the patent document provides a method of degrading a target protein in a cell. The method includes contacting the cell with an effective amount of a compound of Formula I disclosed herein, wherein the compound effectuates the degradation of the target protein in the cell. Nonlimiting examples of the target proteins include c-MYC (cellular Myelocytomatosis), n-MYC (also known as basic helix-loop-helix protein 37), CRBN (cereblon), HDAC (histone deacetylases), IKZF1 (Ikaros Zinc Finger Transcription Factor, Ikaros) IKZF2 (Helios), IKZF3 (aiolos), IKZF4 (Eos), IRF4 (interferon regulatory factor 4), NFκB (Nuclear factor kappa-light-chain-enhancer of activated B cells), p21 (CDK-interacting protein 1), p53 (tumor protein PS3), TNF-α (tumor necrosis factor alpha), IL-2 (interleukin-2) and others. In a related aspect, the compound inhibited the activities of the histone deacetylases (HDACs). In another related aspect, the compound modulates cytokine production from human immune cells.

EXAMPLES

Example 1. Compound Synthesis

The pleiotropic pathway modifier (PPM) compounds can be prepared in various approaches. An example approach is illustrated in Scheme 1.

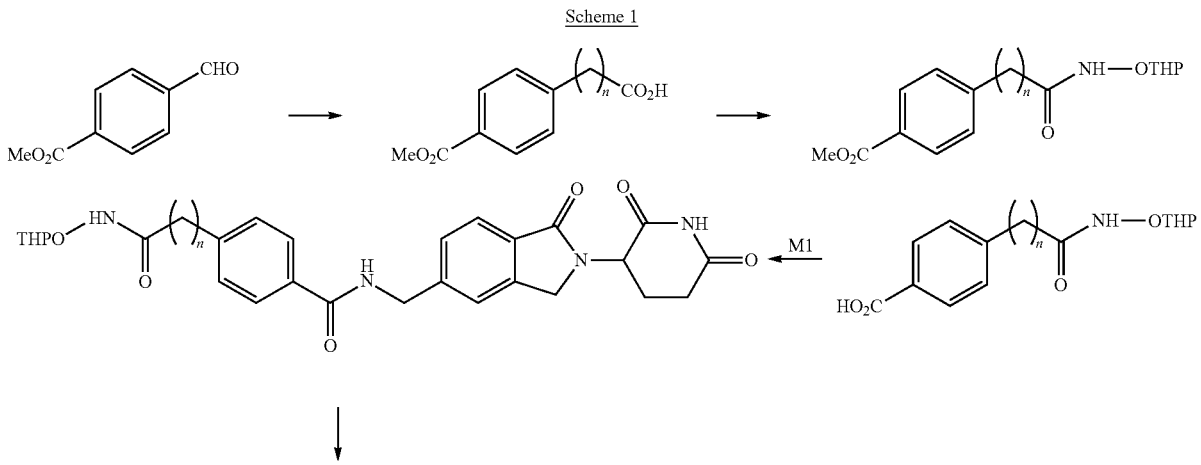

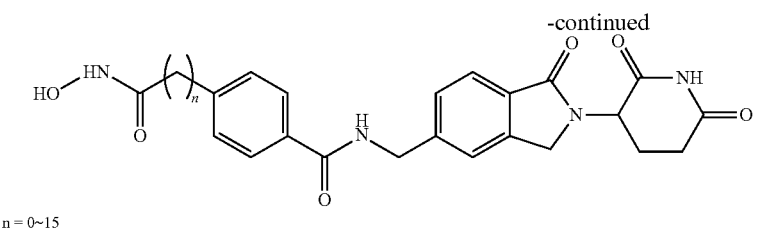

n = 0~15

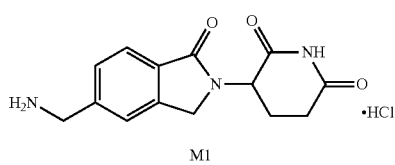

M1 [CAS umber 1158264-69-7]

Example 2. Synthesis of N-((2-(2,6-dioxopiperidin-3-yl)-1-oxoisoindolin-5-yl)methyl)-4-(3-(hydroxyamino)-3-oxopropyl)benzamide (compound 2)

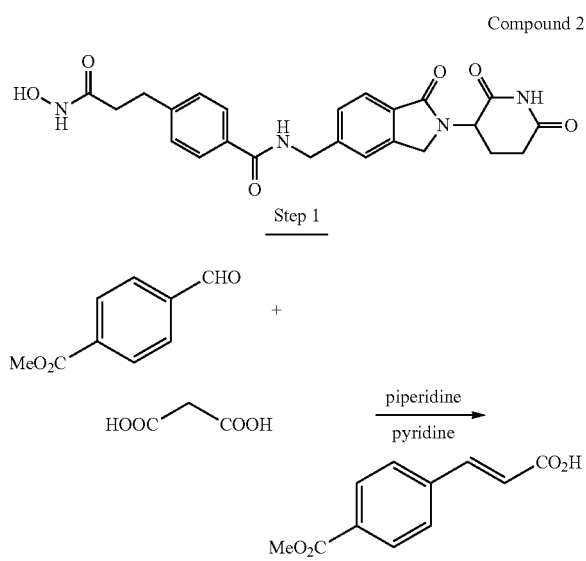

Compound 2

At room temperature, to the solution of methyl 4-formylbenzoate (10 g) and malonic acid (9.5 g) in pyridine (60 ml) was added piperidine (0.42 g). The above reaction solution was heated to 85° C. and stirred for 6 hours. The reaction solution was cooled to room temperature and poured into 100 ml of aqueous 2N HCl. The solid was collected via filtration and washed with water (30 ml) and acetonitrile (3×60 ml). The solid was dried to give 1.4 g of 3-(4-(methoxycarbonyl)phenyl)acrylic acid as white solid with 97% purity.

Step 2

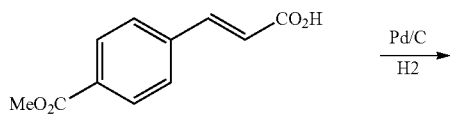

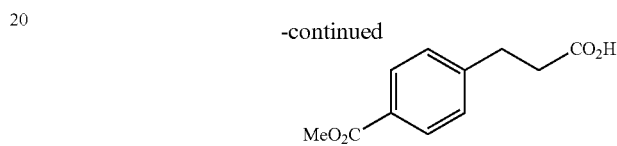

At room temperature, 1.4 g of 3-(4-(methoxycarbonyl)phenyl)acrylic acid (5 g) in MeOH (30 ml) was exchanged with nitrogen three times. 10% of Pd/C (0.5 g) was added. The reaction mixture was charged with $H_2$ (balloon) and stirred overnight. The Pd/C was filtered off via celite and washed with MeOH (20 ml). After MeOH was removed under reduced pressure, 4.7 g of 3-(4-(methoxycarbonyl)phenyl) propanoic acid was made with 97% purity as white solid.

Step 3

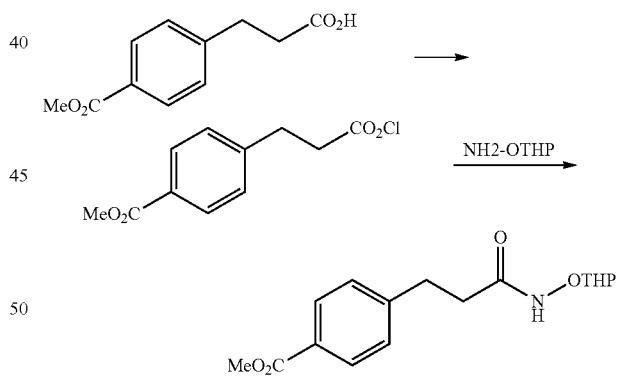

To the solution of 3-(4-(methoxycarbonyl)phenyl) propanoic acid (1.1 g) in anhydrous Dichloromethane (5 ml) was added dropwise Oxalyl Chloride (0.54 ml) at room temperature. The reaction solution was stirred for 3 hours at room temperature and concentrated, and the reside was dissolved in anhydrous Dichloromethane (2 ml) to give 3-(4-(methoxycarbonyl)phenyl)propanoic acid chloride solution in Dichloromethane O-(tetrahydro-2H-pyran-2-yl)hydroxylamine (0.56 g) was azeotropically dried in toluene (3 ml) and then dissolved in anhydrous Dichloromethane (3 ml). Triethylamine (0.86 ml) was added. To this solution was added dropwise 3-(4-(methoxycarbonyl)phenyl) propanoic acid chloride solution in Dichloromethane under ice bath. After addition, the ice batch was removed and the reaction was stirred at room temperature for 3 hours. The reaction mixture as quenched with aq. NaHCO$_3$, and extracted with Ethyl Acetate, dried over anhydrous Na$_2$SO4. After concentration, the product was purified via Biotage Flash Chromatography to give 0.82 g of pure product methyl 4-(3-oxo-3-(((tetrahydro-2H-pyran-2-yl)oxy)amino)propyl)benzoate as white solid with 97% purity.

Step 4

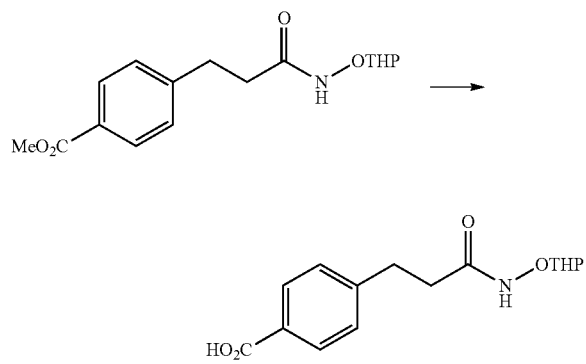

To the solution of methyl 4-(3-oxo-3-(((tetrahydro-2H-pyran-2-yl)oxy)amino)propyl)benzoate (307 mg) in THF/H$_2$O/MeOH (3 ml/1 ml/1 ml) was added LiOH·H$_2$O (200 mg) at room temperature. After stirred overnight at room temperature, the reaction mixture was added 10 ml of water and adjusted PH=6 using aq. Citric acid, followed by extraction with Ethyl Acetate. The Ethyl Acetate layer was dried over anhydrous Na$_2$SO$_4$, and concentrated to give 220 mg of 4-(3-oxo-3-(((tetrahydro-2H-pyran-2-yl)oxy)amino)propyl)benzoic acid as white solid with 97% purity.

Step 5

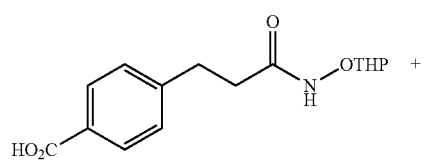

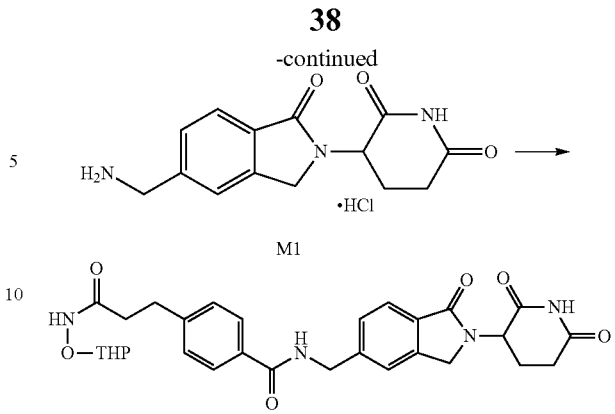

To the mixture of 4-(3-oxo-3-(((tetrahydro-2H-pyran-2-yl)oxy)amino)propyl)benzoic acid (87.4 mg), M1 (100 mg) in anhydrous DMF (1 ml) was added 1-Propylphosphonic anhydride (310 mg, 50 wt % solution in DMF), and followed by N-methylmorpholine (82 mg) at room temperature. The reaction mixture was heated to 40° C. and stirred for 15 hours. After cooled to room temperature, to the reaction mixture was added 3 ml of saturated aq. NaHCO$_3$ and vigorously stirred for 15 minutes. Solid was collected via filtration and washed with water (3×5 ml) and Ethyl acetate (3×5 ml). Ater dried under vacuum overnight, 85 mg of N-((2-(2,6-dioxopiperidin-3-yl)-1-oxoisoindolin-5-yl)methyl)-4-(3-oxo-3-(((tetrahydro-2H-pyran-2-yl)oxy)amino)propyl)benzamide was made with 97% purity as white solid.

Step 6

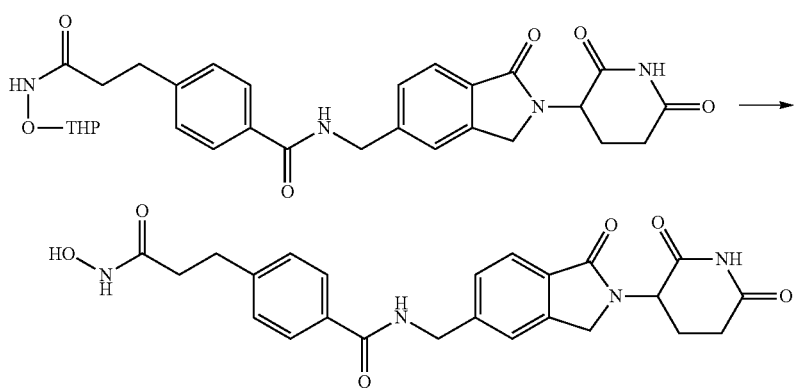

compound 2

To N-((2-(2,6-dioxopiperidin-3-yl)-1-oxoisoindolin-5-yl)methyl)-4-(3-oxo-3-(((tetrahydro-2H-pyran-2-yl)oxy)amino)propyl)benzamide (41 mg) in Ethyl acetate/MeOH (1.5 ml/0.3 ml) was added HCl in Ethyl acetate (0.5 ml, 1M) at room temperature. The reaction mixture was stirred for 3 hours. 10 ml of water was added and stirred for 10 minutes. Solid was collected via filtration and followed by washing with water and Athyl acetate. After dried under vacuum, 35 mg of the final compound N-((2-(2,6-dioxopiperidin-3-yl)-1-oxoisoindolin-5-yl)methyl)-4-(3-(hydroxyamino)-3-oxo-propyl)benzamide (compound 2) was made as white solid with Purity 98% (by HPLC). MS(ESI) found m/z 465,19 [M+1], $^1$HNMR (DMSO-d6) 10.95 (s, 1H), 10.35 (s, 1H), 9.04 (s, 1H), 8.68 (s, 1H), 7.81 (d, 2H), 7.68 (d, 1H), 7.53 (s, 1H), 7.45 (d, 1H), 7.29 (d, 2H), 5.08 (m, 1H), 4.58 (d, 2H), 4.294.45 (dd, 2H), 2.85-2.93 (m, 3H), 2.58-2.61 (m, 1H), 2.36-2.41 (m, 1H), 2.27-2.30 (m, 2H), 1.69-2.01 (m, 1H).

Example 3. Synthesis of N-((2-(2,6-dioxopiperidin-3-yl)-1-oxoisoindolin-5-yl)methyl)-4-(5-(hydroxyamino)-5-oxopentyl)benzamide (Compound 4)

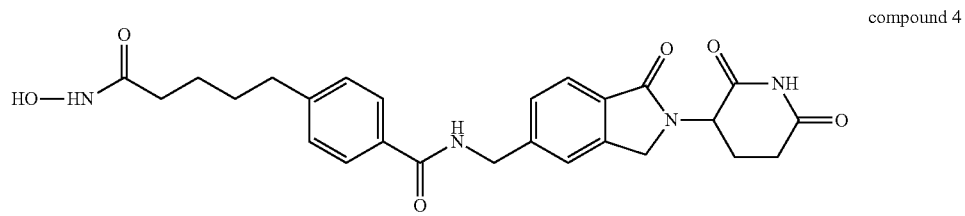 [SMILES: O=C(CCCCc1ccc(C(=O)NCc2ccc3c(c2)CN(C2CCC(=O)NC2=O)C3=O)cc1)NO]

compound 4

Step 1

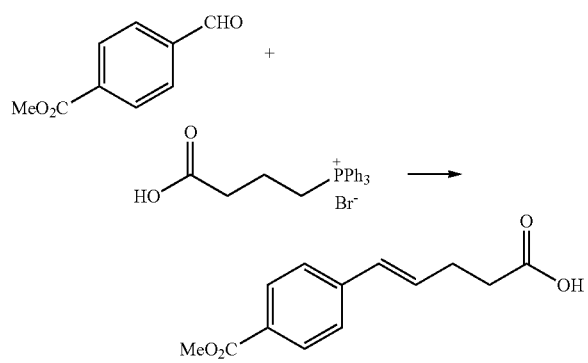

A mixture of methyl 4-formylbenzoate (3.28 g) and (3-carboxypropyl)triphenylphosphonium bromide (8.58 g) in DMSO/THF (40 m/40 ml) was cooled under ice bath. NaH (1.6 g, 60% in mineral oil) was added in portions. After stirred for 0.5 hours, cold bath was removed and stirred at room temperature for additional 2 hours until methyl 4-formylbenzoate disappeared monitored by LCMS. Iced water (100 ml) was added and followed by aq. HCl (00 ml, 12N). Extracted with Ethyl acetate (3×80 ml) and combined organic solvent was washed with brine (50 ml) and dried over anhydrous Na2SO4. After concentration, the crude product was purified via Biotage Flash Chromatography to give 4.4 g of product 5-(4-(methoxycarbonyl)phenyl)pent-4-enoic acid as white solid with 97% purity.

Using 5-(4-(methoxycarbonyl)phenyl)pent-4-enoic acid, followed Step 2-6 as described in synthesis of compound 2, the final compound N-((2-(2,6-dioxopiperidin-3-yl)-1-oxoisoindolin-5-yl)methyl)-4-(5-(hydroxyamino)-5-oxopentyl)benzamide (compound 4) was made with Purity 98% (by HPLC). MS(ESI) found m/z 493.30[M+1], $^1$HNMR (DMSO-d6) $^1$HNMR (DMSO-d6) 10.95 (s, 1H), 10.32 (s, 1H), 9.03 (s, 1H), 8.63 (s, 1H), 7.82 (d, 2H), 7.68 (d, 1H), 7.53 (s, 1H), 7.45 (d, 1H), 7.29 (d, 2H), 5.08 (m, 1H), 4.57 (d, 2H), 4.29-4.45 (dd, 2H), 2.87-2.93 (m, 1H), 2.61-2.64 (m, 3H), 2.34-2.41 (m, 1H), 1.67-2.01 (m, 3H), 1.53-1.57 (m, 4H).

Example 4. Synthesis of N-((2-(2,6-dioxopiperidin-3-yl)-1-oxoisoindolin-5-yl)methyl)-4(64-(hydroxyamino)-6-oxohexyl)benzamide (Compound 5)

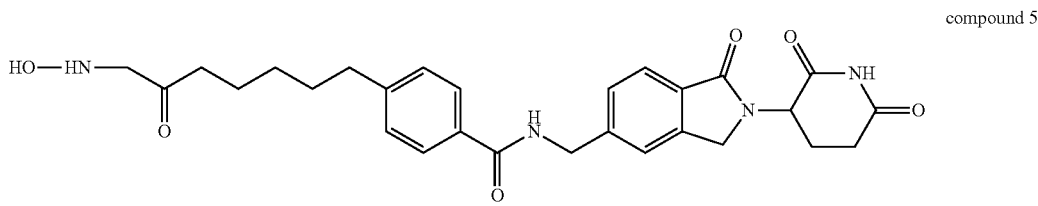 [SMILES: O=C(CCCCCc1ccc(C(=O)NCc2ccc3c(c2)CN(C2CCC(=O)NC2=O)C3=O)cc1)CNO]

compound 5

Starting with methyl 4-formylbenzoate and (4-carboxybutyl)triphenylphosphonium bromide, followed the steps 1-6 described in synthesis of product compound 4, the final product N-((2-(2,6-dioxopiperidin-3-yl)-1-oxoisoindolin-5-yl)methyl)-4-(6-(hydroxyamino)-6-oxohexyl)benzamide (compound 5) was made with Purity 98% (by HPLC). MS(ESI) found m/z 507.3[M+1], $^1$HNMR (DMSO-d6) 10.95 (s, 1H), 10.29 (s, 1H), 9.03 (s, 1H), 8.62 (s, 1H). 7.81 (d, 2H), 7.68 (d, 1H), 7.53 (s, 1H), 7.45 (d, 1H), 7.28 (d, 2H), 5.08 (m, 1H), 4.57 (d, 2H), 4.294.45 (m, 2H), 2.87-2.93 (m, 1H), 2.61-2.64 (m, 3H), 2.27-2.40 (m, 1H), 1.98-2.00 (m, 3H), 1.51-1.60 (m, 4H), 1.24-1.28 (m, 2H).

Example 5. Synthesis of N-((2-(2,6-dioxopiperidin-3-yl)-1-oxoisoindolin-5-yl)methyl)-4-(8-(hydroxyamino)-8-oxooctyl)benzamide (compound 7)

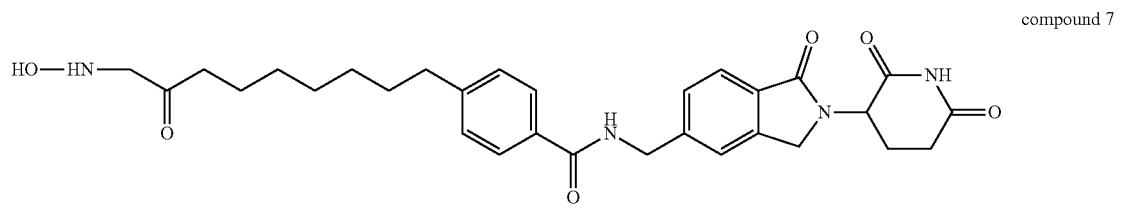 [SMILES: O=C(CCCCCCCc1ccc(C(=O)NCc2ccc3c(c2)CN(C2CCC(=O)NC2=O)C3=O)cc1)CNO]

compound 7

Wittig reagent (6-carboxyhexyl)triphenylphosphonium bromide was made smoothly based on the general procedure by reacting with PPh3 and 7-bromoheptanoic acid in CH3CN at refluxing for 12 h hours. Then followed the step 1-6 described in synthesis of product compound 5, the final product N-((2-(2,6-dioxopiperidin-3-yl)-1-oxoisoindolin-5-yl)methyl)-4-(8-(hydroxyamino)-8-oxooctyl)benzamide (compound 7) was made with Purity 98% (by HPLC). MS(ESI) found m/z 535.3[M+1], 1HNMR (DMSO-d6) 10.95 (s, 1H), 10.29 (s, 1H), 9.03 (s, 1H), 8.61 (s, 1H), 7.83 (d, 2H), 7.68 (d, 1H), 7.53 (s, 1H), 7.45 (d, 1H), 7.26 (d, 2H), 5.08 (m, 1H), 4.57 (d, 2H), 4.29-4.45 (m, 2H), 2.87-2.93 (m, 1H), 2.58-2.63 (m, 3H), 2.20-2.39 (m, 2H), 1.98-2.00 (m, 1H), 1.90-1.92 (m, 1H), 1.45-1.58 (m, 4H), 1.20-1.22 (m, 6H).

The pleiotropic pathway modifier (PPM) compounds were made based on the following Scheme

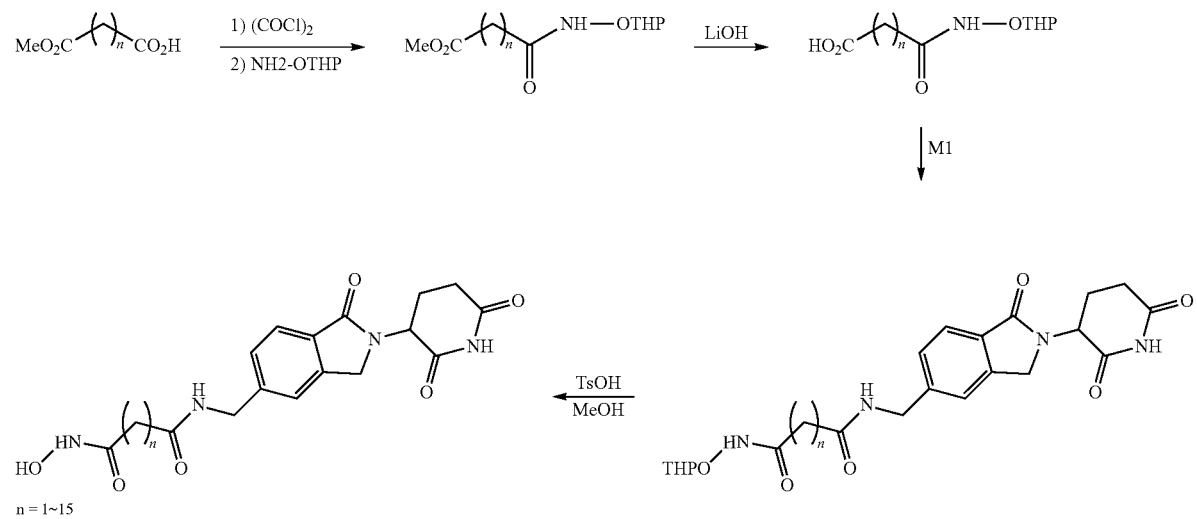

n = 1~15

Example 6. Synthesis of N1-((2-(2,6-dioxopiperidin-3-y)-1-oxoisoindolin-5-yl)methyl)-N4-hydroxysuccinamide (compound 204)

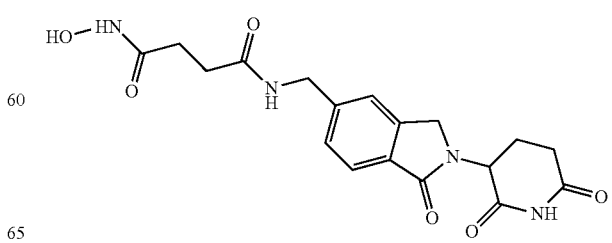

compound 204

Step 1

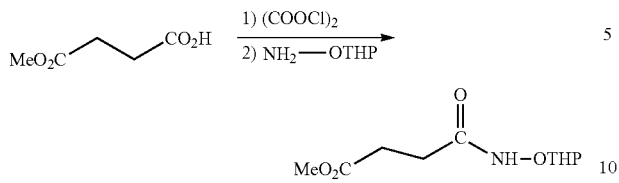

To the solution of 4-methoxy-4-oxobutanoic acid (3.0 g) in anhydrous Dichloromethane (15 ml) was added dropwise Oxalyl Chloride (2.6 ml) at 0° C. The reaction solution was stirred for 3 hours at room temperature and concentrated, and the reside was dissolved in anhydrous Dichloromethane (5 ml) to give methyl 4-chloro-4-oxobutanoate solution in Dichloromethane O-(tetrahydro-2H-pyran-2-yl)hydroxylamine (2.66 g) was azeotropically dried in toluene (5 ml) and then dissolved in anhydrous Dichloromethane (10 ml). Triethylamine (6.3 ml) was added. To this solution was added dropwise methyl 4-chloro-4-oxobutanoate solution in Dichloromethane under ice bath. After addition, the ice batch was removed and the reaction was stirred at room temperature for 5 hours. The reaction mixture was quenched with aq. NaHCO$_3$, and extracted with Ethyl Acetate, dried over anhydrous Na$_2$SO4. After concentration, the product was purified via Biotage Flash Chromatography to give 2.0 g of pure product methyl 4-oxo-4-(((tetrahydro-2H-pyran-2-yl)oxy)amino)butanoate as yellow oil with 97% purity.

Step 2

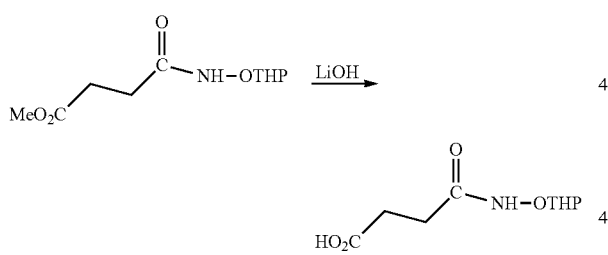

To the solution of methyl 4-oxo-4-(((tetrahydro-2H-pyran-2-yl)oxy)amino)butanoate (0.55 g) in THF/H$_2$O/MeOH (15 ml/15 ml/3 ml) was added LiOH·H$_2$O (1.33 g) at room temperature. After stirred overnight at room temperature, the reaction mixture was added 10 ml of water and adjusted PH=6 using aq. Citric acid, followed by extraction with Ethyl Acetate. The Ethyl Acetate layer was dried over anhydrous Na$_2$SO$_4$, and concentrated to give 600 mg of 4-oxo-4-(((tetrahydro-2H-pyran-2-yl)oxy)amino)butanoic acid as white solid with 97% purity.

Step 3

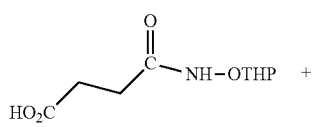

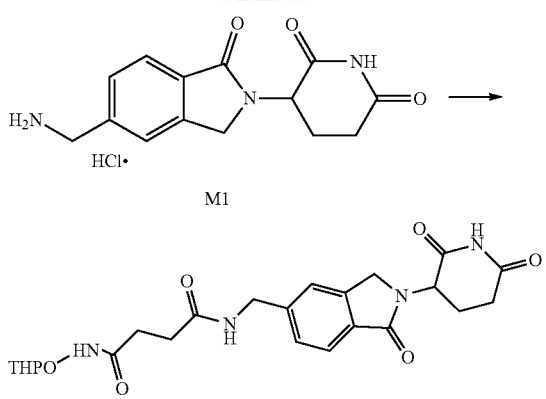

To the mixture of 4-oxo-4-(((tetrahydro-2H-pyran-2-yl)oxy)amino)butanoic acid (69 mg) and MI (100 mg) in anhydrous DMF (1 ml) was added 1-Propylphosphonic anhydride (310 mg, 50 wt % solution in DMF), and followed by N-methylmorpholine (82 mg) at room temperature. The reaction mixture was heated to 40° C. and stirred for 15 hours. After cooled to room temperature, to the reaction mixture was added 3 ml of saturated aq. NaHCO$_3$ and extracted with Ethyl acetate (3×5 ml). After concentration, the crude product was purified via Biotage Flash Chromatagraphy to give 40.5 mg N1-((2-(2,6-dioxopiperidin-3-yl)-1-oxoisoindolin-5-yl)methyl)-N4-((tetrahydro-2H-pyran-2-yl)oxy)succinamide with 97% purity as off white solid.

Step 4

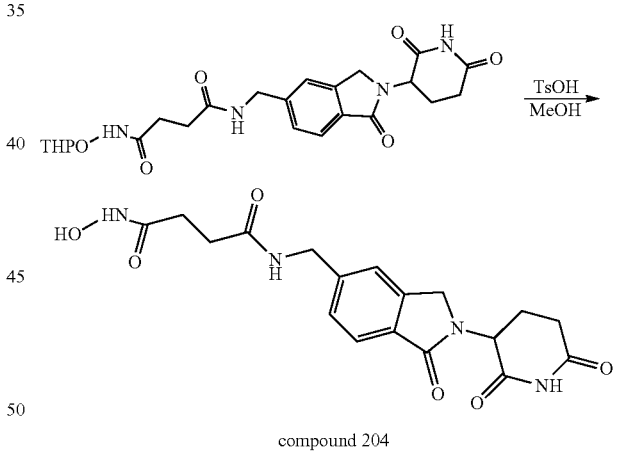

compound 204

To a solution of N1-((2-(2,6-dioxopiperidin-3-yl)-1-oxoisoindolin-5-yl)methyl)-N4-((tetrahydro-2H-pyran-2-yl)oxy)succinamide (38 mg) in MeOH (1 ml) was added p-Toluenesulfonic acid monohydrate (TsOH·H$_2$O) (16 mg). After reaction completed monitored by HPLC, the reaction mixture was diluted with ethyl acetate (5 ml) and washed with saturated aq NaHCO$_3$ and brine. After concentration, the crude product was purified via Biotage Flash Chromatagraphy to give 3.2 mg of N1-((2-(2,6-dioxopiperidin-3-yl)-1-oxoisoindolin-5-yl)methyl)-N4-hydroxysuccinamide (compound 204) as white solid with 98% purity.

The pleiotropic pathway modifier (PPM) compounds below were made based on the following Scheme

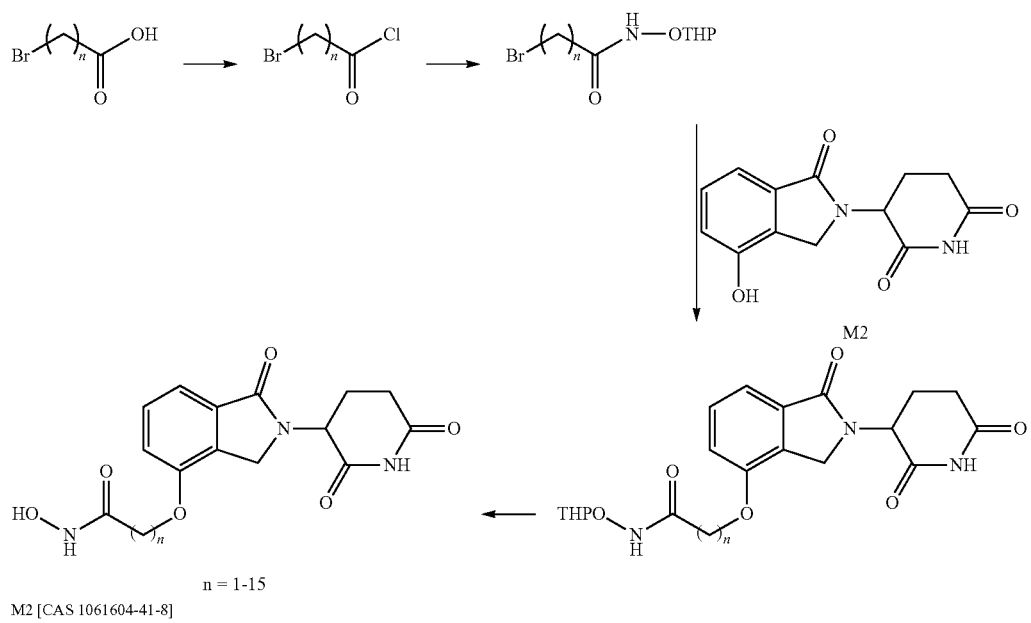

n = 1-15
M2 [CAS 1061604-41-8]

Example 7. Synthesis of 4-((2-(2,6-dioxopiperidin-3-yl)-1-oxoisoindolin-4-yl)oxy)-N-hydroxybutanamide (Compound 217)

compound 217

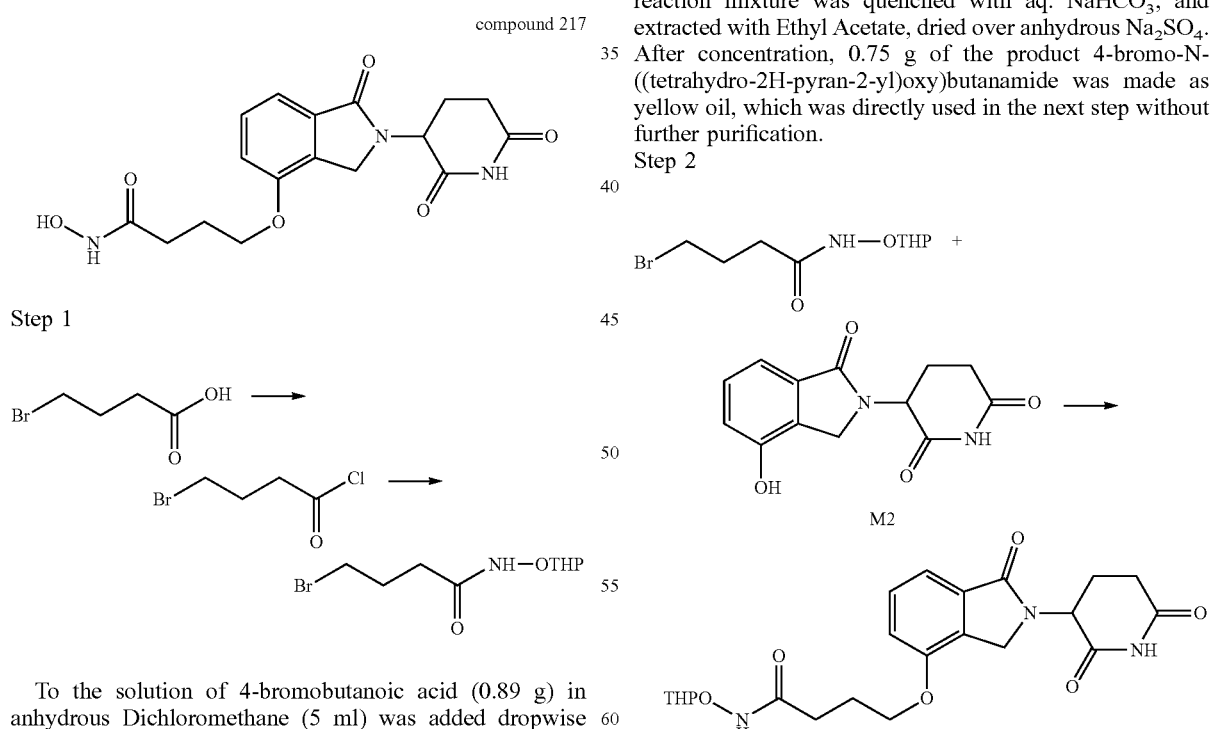

Step 1

To the solution of 4-bromobutanoic acid (0.89 g) in anhydrous Dichloromethane (5 ml) was added dropwise Oxalyl Chloride (0.54 ml) at 0° C. The reaction solution was stirred for 3 hours at room temperature and concentrated, and the reside was dissolved in anhydrous Dichloromethane (1 ml) to give 4-bromobutanoyl chloride solution in Dichloromethane O-(tetrahydro-2H-pyran-2-yl)hydroxylamine (0.56 g) was azeotropically dried in toluene (5 ml) and then dissolved in anhydrous Dichloromethane (4 ml). Triethylamine (1.5 ml) was added. To this solution was added dropwise 4-bromobutanoyl chloride solution in Dichloromethane under ice bath. After addition, the ice batch was removed and the reaction was stirred at room temperature for 5 hours. The reaction mixture was quenched with aq. $NaHCO_3$, and extracted with Ethyl Acetate, dried over anhydrous $Na_2SO_4$. After concentration, 0.75 g of the product 4-bromo-N-((tetrahydro-2H-pyran-2-yl)oxy)butanamide was made as yellow oil, which was directly used in the next step without further purification.

Step 2

To a solution of 4-bromo-N-((tetrahydro-2H-pyran-2-yl)oxy)butanamide (112 mg) from the previous step and M2 (100 mg) in anhydrous DMF (1 ml) was added anhydrous $K_2CO_3$ (105 mg) under iced water bath. The reaction was allowed to warm to room temperature and stirred for 4 hours. 3 ml of water was added and extracted with ethyl acetate (5 ml×3). The combined organic solvent was concentrated. The residue was purified via Biotage Flash Chromatography to give 90 mg of 4-((2-(2,6-dioxopiperidin-3-yl)-1-oxoisoindolin-4-yl)oxy)-N-((tetrahydro-2H-pyran-2-yl)oxy)butanamide as off white solid with 97% purity.
Step 3

Chromatography to give 30 mg of product 4-((2-(2,6-dioxopiperidin-3-yl)-1-oxoisoindolin-4-yl)oxy)-N-hydroxybutanamide (compound 217) as white solid with 98% purity.

Example 8. Synthesis of 6-((2-(2,6-dioxopiperidin-3-yl)-1-oxoisoindolin-4-yl)oxy)-N-hydroxyhexanamide (Compound 219)

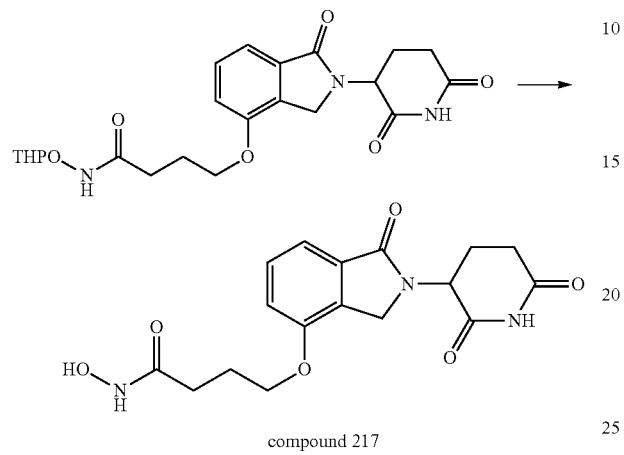

compound 217

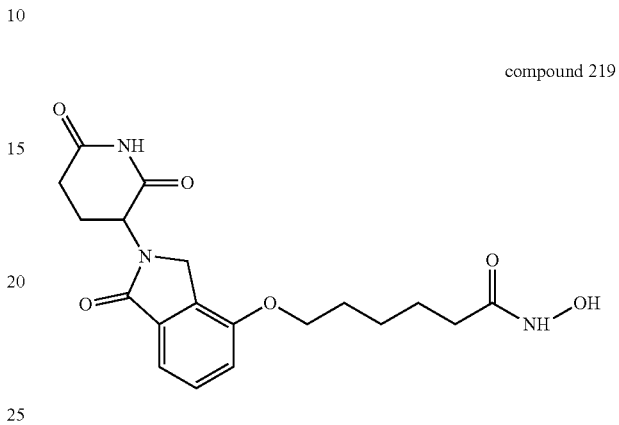

compound 219

To the suspension of 4-((2-(2,6-dioxopiperidin-3-yl)-1-oxoisoindolin-4-yl)oxy)-N-((tetrahydro-21-pyran-2-yl)oxy)butanamide (90 mg) in Ethyl acetate (2 ml) was added HCl in ethyl acetate (3 ml, 0.1M) at room temperature. After 2 hours, HPLC showed no starting material remained. The reaction was quenched with saturated aq NaHCO₃. Ethyl acetate was used to extract the product and concentrated to give crude product, which as purified via Biotage Flash Starting with 6-bromohexanoic acid, followed the step 1-3 described in the procedure of synthesis of compound 217. The product 6-((2-(2,6-dioxopiperidin-3-yl)-1-oxoisoindolin-4-yl)oxy)-N-hydroxyhexanamide (compound 219) was made with 98% purity.

Example 9. Synthesis of 7-(4-(2-(((2-(2,6-dioxopiperidin-3-yl)-1-oxoisoindolin-5-yl)methyl)amino)-1,1-difluoro-2-oxoethyl)phenyl)-N-hydroxyheptanamide (Compound 256)

compound 256

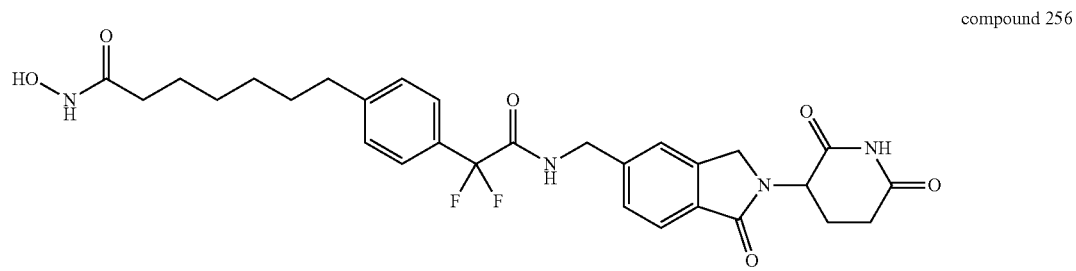 [SMILES: O=C(CCCCCCc1ccc(C(F)(F)C(=O)NCc2ccc3c(c2)CN(C2CCC(=O)NC2=O)C3=O)cc1)NO]

Step 1

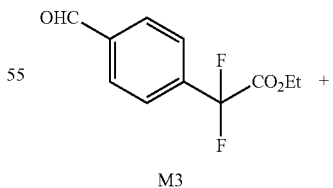

M3

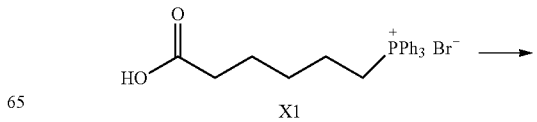

X1

-continued

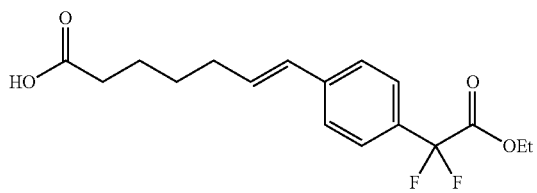

To a solution of (5-carboxypentyl)triphenylphosphonium bromide (X1)(6.13 g, [CAS 50889-29-7]) in DMSO-THF (40 ml-20 ml) was cooled to 0° C., 1 g of NaH (60% in mineral oil) was added in portions. After 1 hour, ethyl 2,2-difluoro-2-(4-formylphenyl)acetate(M3)(2.78 g, [CAS 936352-93-1]) in THF (20 ml) was added drop wisely into the reaction mixture and allowed temperature automatically reached to room temperature overnight. Aq; HCl (5 ml, 12N) and water (150 ml) was added to the reaction mixture. The product was extracted with Ethyl acetate and purified via Biotage Flash Chromatography Column to give product (7-(4-(2-ethoxy-1,1-difluoro-2-oxoethyl)phenyl)hept-6-enoic acid (5.1 g), which is used in the next step.

Step 2

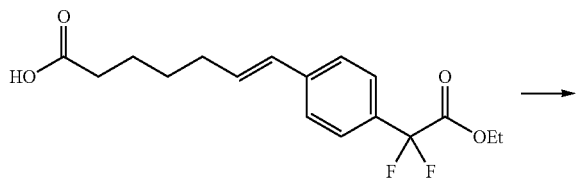

To a solution of (7-(4-(2-ethoxy-1,1-difluoro-2-oxoethyl)phenyl)hept-6-enoic acid (5.1 g) in Ethyl Acetate (50 ml) was added Pd/C (10%) (600 mg). The reaction mixture was stirred under 1 atm of Hydrogen after purged with Argon at room temperature. After 3 hours, the solid Pd/C was filtered off and washed with ethyl acetate. The combined ethyl acetate solution was concentrated to give the product 7-(4-(2-ethoxy-1,1-difluoro-2-oxoethyl)phenyl)heptanoic acid (2.1 g), which is directly used in the next step without further purification.

Step 3

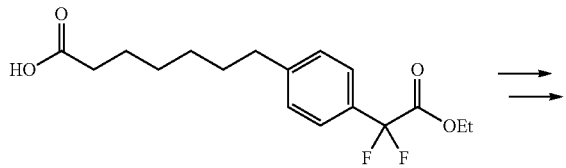

-continued

To the solution of 7-(4-(2-ethoxy-1,1-difluoro-2-oxo-ethyl)phenyl)heptanoic acid (1.02 g) in anhydrous Toluene (5 ml) and DMF (0.1 ml) was added dropwise Oxalyl Chloride (0.4 ml) at room temperature. The reaction solution was stirred for 3 hours at room temperature and concentrated, and the reside was dissolved in anhydrous Dichloromethane (3 ml) to give ethyl 2-(4-(7-chloro-7-oxoheptyl)phenyl)-2,2-difluoroacetate solution in Dichloromethane. O-(tetrahydro-2H-pyran-2-yl)hydroxylamine (0.54 g) was azeotropically dried in toluene (3 ml) and then dissolved in anhydrous Dichloromethane (5 ml). Triethylamine (1.4 g) was added and followed by slow adding ethyl 2-(4-(7-chloro-7-oxoheptyl)phenyl)-2,2-difluoroacetate under ice bath. After addition, the ice batch was removed and the reaction was stirred at room temperature for 3 hours. The reaction mixture as quenched with aq. NaHCO₃, and extracted with Ethyl Acetate, dried over anhydrous Na₂SO4. After concentration, the product was purified via Biotage Flash Chromatography to give 1.1 g of pure product ethyl 2,2-difluoro-2-(4-(7-oxo-7-(((tetrahydro-2H-pyran-2-yl)oxy)amino)heptyl)phenyl)acetate as white solid with 97% purity.

Step 4

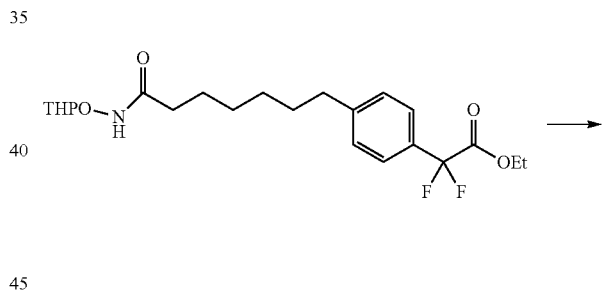

To the solution of ethyl 2,2-difluoro-2-(4-(7-oxo-7-(((tetrahydro-2H-pyran-2-yl)oxy)amino)heptyl)phenyl)acetate (1.1 g) in THF/H₂O/MeOH (6 ml/2 ml/2 ml) was added LiOH·H₂O (324 mg) at room temperature. After stirred overnight at room temperature, the reaction mixture was added 10 ml of water and adjusted PH=6 using aq. Citric acid, followed by extraction with Ethyl Acetate. The Ethyl Acetate layer was dried over anhydrous Na₂SO₄, concentrated and purified by Biotag Chromatography to give 300 mg of 2,2-difluoro-2-(4-(7-oxo-7-(((tetrahydro-2H-pyran-2-yl)oxy)amino)heptyl)phenyl)acetic acid with 97% purity.

Step 5

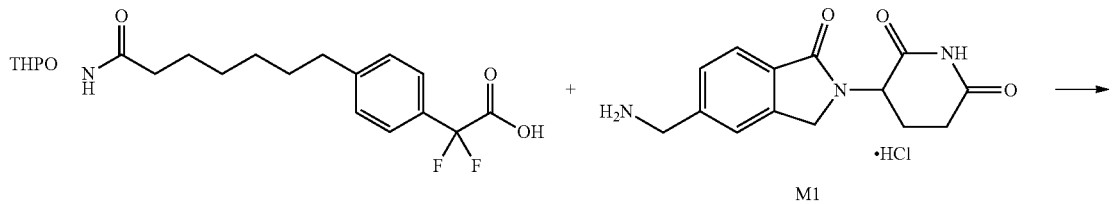

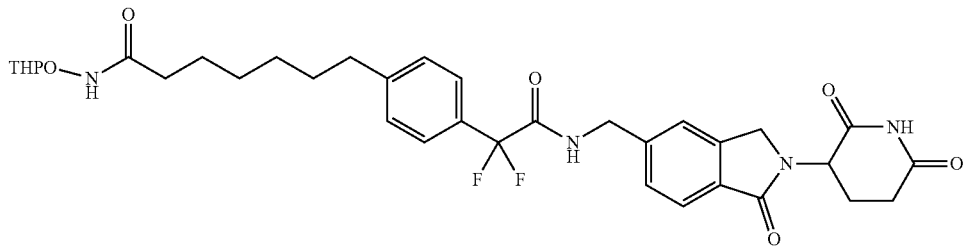

To the mixture of 2,2-difluoro-2-(4-(7-oxo-7-(((tetrahydro-2H-pyran-2-yl)oxy)amino)heptyl)phenyl)acetic acid (124 mg), MI (100 mg) in anhydrous DMF (1.5 ml) was added 1-Propylphosphonic anhydride (344 mg, 50 wt % solution in DMF), and followed by N-methylmorpholine (208 mg) at room temperature. The reaction mixture was heated to 40° C. and stirred for 20 hours. After coiled to room temperature, to the reaction mixture was added 10 ml of saturated aq. NaHCO₃ and extracted with Ethyl acetate. The combined organic phases were washed with brine and concentrated. The residue was purified with Biotag Chromatography to give 108 mg 7-(4-(2-(((2-(2,6-dioxopiperidin-3-yl)-1-oxoisoindolin-5-yl)methyl)amino)-1,1-difluoro-2-oxoethyl)phenyl)-N-((tetrahydro-2H-pyran-2-yl)oxy)heptanamide as white solid with 97% purity (by HPLC).

Step 6

To 7-(4-(2-(((242,6-dioxopiperidin-3-yl)-1-oxoisoindolin-5-yl)methyl)amino)-1,1-difluoro-2-oxoethyl)phenyl)-N-((tetrahydro-2H-pyran-2-yl)oxy)heptanamide (108 mg) in Ethyl acetate/MeOH (0.5 ml/1.0 ml) was added HCl in Ethyl acetate (0.4 ml, 1.9M) at room temperature. The reaction mixture was stirred for 3 hours at room temperature until LCMS showed no more starting materials remained. The reaction mixture was concentrated and purified with Biotag Chromatography to give 41 mg of the final compound 7-(4-(2-(((2-(2,6-dioxopiperidin-3-yl)-1-oxoisoindolin-5-yl)methyl)amino)-1,1-difluoro-2-oxoethyl)phenyl)-N-hydroxyheptanamide (compound 256) as white solid with Purity 98% (by HPLC). MS(ESI) found m/z 571.23 [M+1] and m/z 593.21 [M+Na]. ¹HNMR (DMSO-d6) 1HNMR (DMSO-d6) 10.96 (s, 1H), 10.30 (s, 1H), 9.57 (s, 1H), 8.61 (s, 1H), 7.83 (d, 2H), 7.68 (d, 1H), 7.53 (s, 1H), 7.45 (d, 1H),

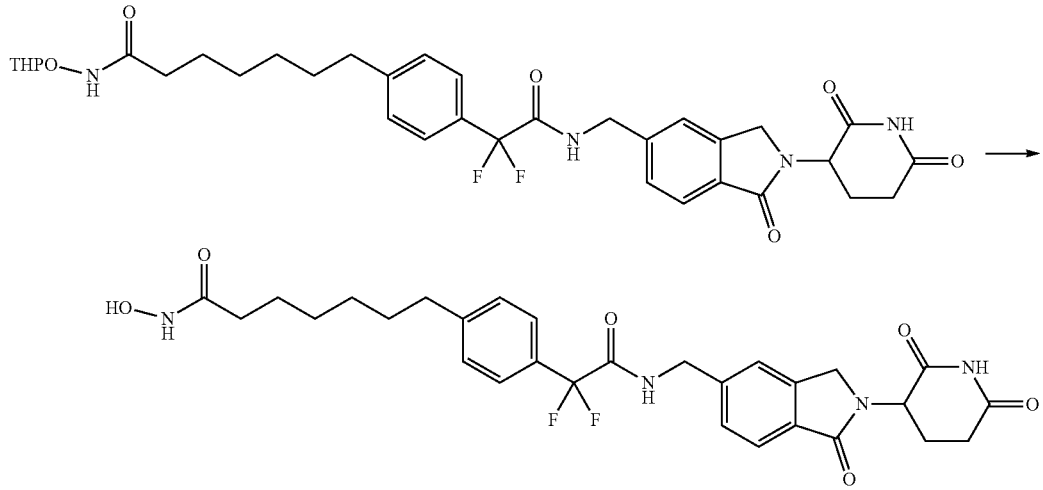

compound 256

7.26 (d, 2H), 5.08 (m, 1H), 4.44 (d, 2H), 4.21-4.43 (m, 2H), 2.88 (m, 1H), 2.59 (m, 3H), 2.35 (m, 1H), 2.0 (m, 1H), 1.92 (m, 2H), 1.54 (m, 2H), 1.46 (m, 2H), 1.26 (m, 4H).

Example 10, Synthesis of 8-(4-(2-(((242,6-dioxopiperidin-3-yl)-1-oxoisoindolin-5-yl)methyl)amino)-1,1-difluoro-2-oxoethyl)phenyl)-N-hydroxyoctanamide (Compound 257)

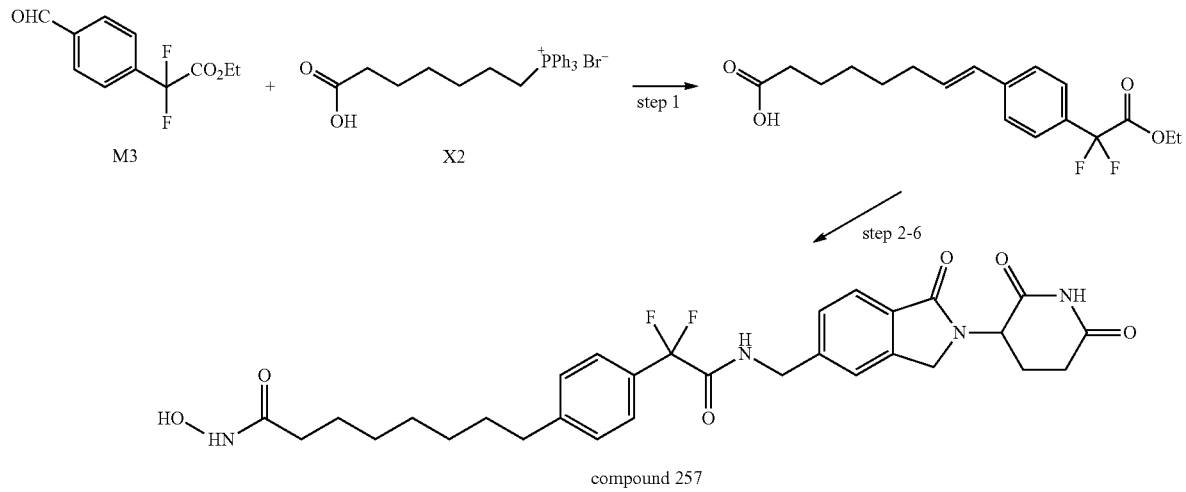

compound 257

In the first step, starting with starting materials M3 [CAS 936352-93-1].

In the first step, starting with starting materials M3 and X2 (CAS [50889-30-01, following the same procedure of Step1 in making Compound 256, (8-(4-(2-ethoxy-1,1-difluoro-2-oxoethyl)phenyl)oct-7-enoic acid was made. Then following the procedure of step 2-6 in making compound 256, 80 mg of 8-(4-(2-(((2-(2,6-dioxopiperidin-3-y)-1-oxoisoindolin-5-yl)methyl)amino)-1,1-difluoro-2-oxoethyl)phenyl)-N-hydroxyoctanamide (compound 257) was made as a white solid with Purity 98% (by HPLC). MS(ESI) found m/z 585.21 [M+1] and m/z 607.201M+Na]; $^1$HNMR (DMSO-d6) 1HNMR (DMSO-d6) 1 1.00 (s, 1H), 10.32 (s, 1H), 10.15 (s, 1H), 9.60 (s, 1H), 7.67 (d, 1H), 7.47-7.49 (m, 2H), 7.41 (s, 1H), 7.33-7.36 (m, 3H), 5.09 (m, 1H), 4.40-4.45 (m, 3H), 4.27-4.29 (m, 1H), 2.88 (m, 1H), 2.59 (m, 3H), 2.35 (m, 1H), 1.98 (m, 1H), 1.92 (m, 2H), 1.56 (m, 2H), 1.44 (m, 2H), 1.21-1.27 (m, 6H).

The selected PPM Compound 4 caused target protein degradation in H929 human multiple myeloma cells and Jurkat human leukemia cells in a concentration dependent manner (FIGS. 3 and 4).

Materials and Methods
Cell Culture

All cancer cells and PBMCs were cultured in RPMI 1640 Medium supplemented with 10% fetal bovine serum and incubated at 37° C. with 5% $CO_2$. Cells were authenticated using the short tandem repeat (STR) assays. *Mycoplasma* test results were negative.

Cancer Cell Proliferation Assay

The cell proliferation of cancer cells was assessed using the CellTiter-Glo Luminescent Cell Viability Assay (Promega), per the manufacturer's protocol.

Briefly, in 96-well flat-bottom white-walled multiwell cell culture plates the control wells containing 100 μL/well medium without cells were used to obtain a value for background luminescence. For treatment wells, cells were seeded at 5,000 in 50 μL/well of complete RPMI-1640 medium and then mixed with 50 μL/well of the vehicle control (0.1% DMSO) or test compounds at indicated concentrations. Following cell incubation for 3 days at 37° C. in a humidified 5% $CO_2$ incubator, the plates were equilibrated at room temperature for approximately 30 minutes. 100 μL of CellTiter-Glo® Reagent were added into each well and then contents were mixed for 2 minutes on an orbital plate shaker to induce cell lysis. After the plates were incubated at room temperature for 10 minutes, luminescent signals of each well were recorded with a Tecan M200 Plate Reader (Tecan Trading AG, Switzerland).

Antibodies and Reagents

Media and other cell culture reagents were purchased from Thermo Fisher. The CellTiter-Glo Assay kit was purchased from Promega. The following antibodies were used in this study: c-Myc and GAPDH (Cell Signaling Technologies); Ikaros, HDAC2 (R&D Systems); CRBN (Novus); Eos (Invitrogen); anti-goat HRP (Santa Cruz Biotechnologies). The anti-rabbit and anti-mouse HRP and the consumable for Simple Western assay were from Protein Simple.

Automatic Western Blot

Targeted protein degradation in test samples were determined using the automated capillary-based nanoproteomic immunoassay Simple Western System (Protein Simple). Cultured cells were washed with cold PBS once and lysed in cold RIPA buffer supplemented with protease and phosphatase inhibitors. The solutions were then incubated at 4° C. for 30 minutes with gentle agitation to fully lyse cells. Each test sample was diluted at 0.4 mg/ml and mixed with 5× reducing buffer with fluorescent molecular weight (MW) standards. Afterwards the samples were heated to 95° C. for 5 minutes, and 5 μL samples were loaded into each capillary tube. Proteins were passed and separated through stacking and separation matrices for 30 minutes at 250 V. Proteins were then immobilized to capillary walls using optimal photoactivated capture chemistry. Following proteins immobilization, capillaries were flushed with a wash buffer and incubated with a blocking reagent for 6 min. Each target protein was probed with a specific primary antibody (diluted in blocking buffer and incubated for 38 min) and a horseradish peroxidase (HRP)-conjugated secondary antibody (ready to use solutions, incubated for 23 min). A mixture of luminol and peroxide was added following manufacturer's protocol. The resulting chemiluminescent signal was captured by a CCD camera, and signal intensities were analyzed using Compass Software (Protein Simple).

Experiments using Luminex-based multiplex assay for cytokine production are shown in FIGS. 5, 6 and 7), which illustrate the immunomodulatory and antiinflammatory activities of the selected compound.

Purified normal human PBMCs were cultured in RPMI-1640 medium supplemented with 10% FBS and antibiotics and maintained in a humidified incubator at 37° C. with 5% $CO_2$. PBMCs (200 μl/well) were cultured in 96 well plates in the serial diluted test compounds for 30 min, and then stimulated with or without various stimuli for 24-72 hr. After treatment, 100 μL of cell culture supernatants in each well were harvested for Luminex-based cytokine assay. A Bio-Plex 200 System was used for this Luminex-based cytokine assay.

HDAC Activity Assay (FIG. 8) showing the HDAC-inhibitory activities of the selected compound.

In Situ HDAC Activity Fluorometric Kit was purchased from Abcam and performed according to the manufacturer instructions. The cells (20,000) were seeded in a black walled 96-well plate and let to adhere overnight, then treated with DMSO or PPM compounds at indicated concentrations for 24 hrs. The media was then replaced with an HDAC substrate (acetylated peptide) dissolved in media and cells incubated for 3 hrs under cell culture conditions, followed by addition of the developer for 30 min to stop the reaction. The fluorescence was measured at Ex/Em=368/442 nm.

1H929 or Jurkat cells were treated with DMSO, the positive control pomalidomide (an FDA-approved immunomodulatory agent) or the selected test compound (compound 4) at indicated concentrations (0.001-10 μM) for 24 hours. Cell lysates were prepared for analysis of intracellular target protein expression levels. The automatic Western blot results showed that compound 4 clearly reduced the levels of c-MYC, HDAC2. Ikaros and other proteins (Table 1),

TABLE 6 compound 4 caused targeted protein degradation
PPM compounds cause targeted protein degradation

| Targets & Cancer Cells | compound 4 |
|---|---|
| c-MYC in H929 cells | degraded |
| Ikaros in H929 cells | degraded |
| CRBN in H929 cells | degraded |
| HDAC2 in H929 cells | degraded |
| GAPDH in H929 cells | No effect |
| c-MYC in Jurkat cells | degraded |
| Ikaros in Jurkat cells | degraded |
| Aiolos in Jurkat cells | degraded |
| CRBN in Jurkat cells | degraded |
| HDAC2 in Jurkat cells | degraded |
| Eos in Jurkat cells | degraded |
| GAPDH in Jurkat cells | No effect |

Figure 1:
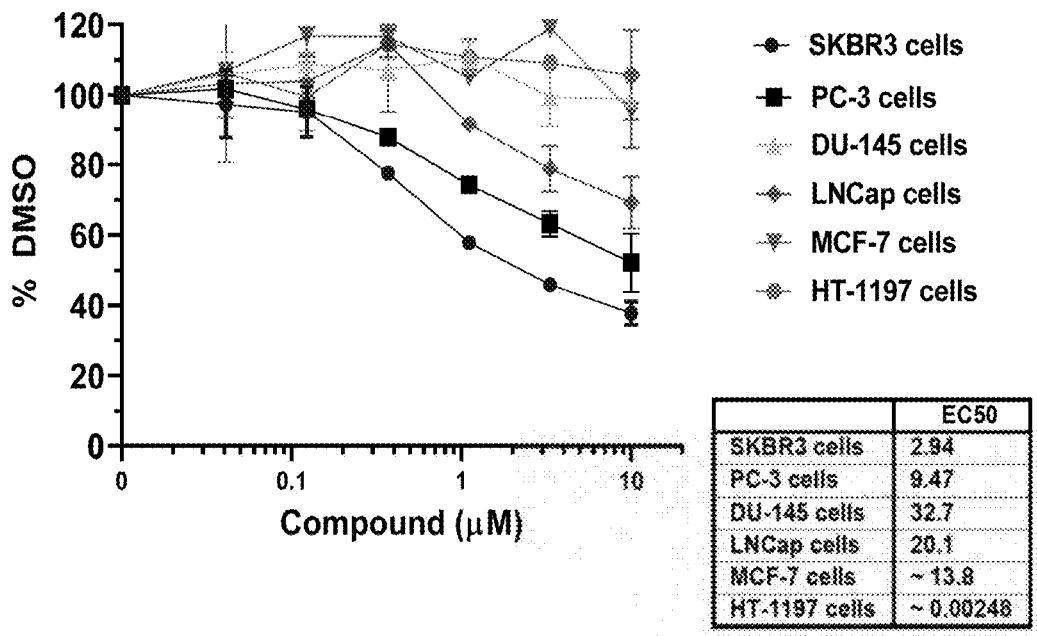
FIG. 1 shows that Compound 4 selectively suppressed the proliferation of human solid tissue cancer cells in a concentration-dependent manner.
Figure 2:
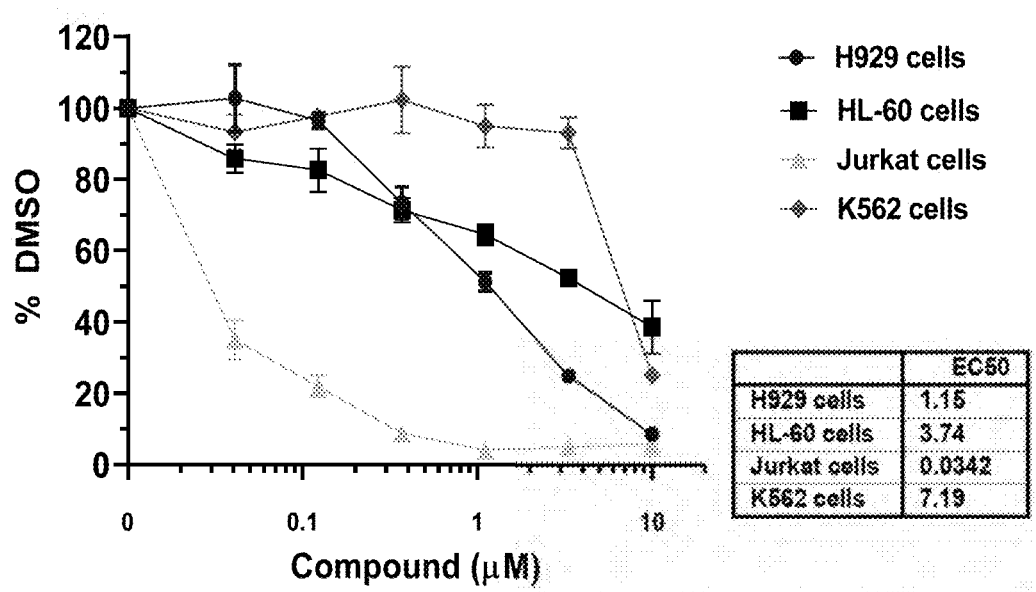
FIG. 2 shows that Compound 4 selectively suppressed the proliferation of human hematopoietic cancer cells in a concentration-dependent manner.

Example 11. PPM Compounds Suppressed the Proliferation of Human Cancer Cells in a Concentration Dependent Manner (FIGS. 1 and 2)

The following human cancer cells originated from various tissues were used to test the antiproliferative activity of PPM compounds (Table 2). Cancer cells were seeded in 96-well plates and treated with a serial dilutions of PPM compounds for 3 days; and the cell proliferation was examined with ATP-based CellTiter assay. The EC50 values for each test compounds were calculated using GraphPad Prizm. Example curves for the concentration-dependent effects of test compounds are shown in FIG. 1 (for solid tumors) and FIG. 2 (for blood cancer cells).

TABLE 7 human cancer cell lines tested in the study

| | |
|---|---|
| 1 | A172: human glioblastoma |
| 2 | A549: human lung cancer |
| 3 | CaKi: human clear cell renal cell carcinoma |
| 4 | DU145: human prostate cancer cell |
| 5 | Farage: human diffuse large B cell lymphoma |
| 6 | Granta-519: human mantle cell lymphoma |
| 7 | H929: human myeloma cell |
| 8 | HCT116: human colon adenocarcinoma |
| 9 | HepG2: human hepatoma |
| 10 | HL-60: human acute promyelocytic leukemia. |
| 11 | HT1197: Human bladder carcinoma |
| 12 | Jurkat: human acute T cell leukemia |
| 13 | K562: human myelogenous leukemia |
| 14 | LNCaP: human prostate cancer cell |
| 15 | LS-180: human colon adenocarcinoma |
| 16 | MCF-7: human breast cancer cell |
| 17 | MDA-MB-231: human breast cancer cell |
| 18 | MiaPaCa-2: human pancreatic cancer |
| 19 | PANC1: human pancreatic cancer |
| 20 | PC-3: human prostate cancer cell |
| 21 | RIVA: human mantle cell lymphoma |
| 22 | RL: human diffuse large B cell lymphoma |
| 23 | RPMI-8226: human mantle cell lymphoma |
| 24 | SKBR-3: human breast cancer cell |
| 25 | SKOV-3: human ovarian cancer cell |
| 26 | SW480: human colon adenocarcinoma |
| 27 | T98G: human glioblastoma |
| 28 | U87 MG: human glioblastoma |

Example 12. PPMs Modulated Cytokine Production from Human Immune Cells (FIGS. 5, 6 and 7)

To investigate the immunological activities of the test compounds, human PBMCs were activated using various stimuli to activate immune cells. The stimuli used in this study were:

Polyinosinic-polycytidylic acid (Poly (I:C)): this in vitro study investigated the potential of Poly (I:C) stimulated human PBMCs as an efficient assay to test compound activity on infection and inflammation. Poly (I:C) induced activation of toll-like receptor 3 (TLR3) in human PBMCs can mimic RNA virus infection to some degree.

Staphylococcal enterotoxin B (SEB): is one of the super-antigens because of its ability to stimulate a large fraction of T cells via interaction with T cell receptors (TCR) and class II MHC molecules. SEB can pronouncedly stimulate expression and secretion of many cytokines or chemokines involved in immune response, inflammation, cell differentiation and growth.

Lipopolysaccharides (LPS), also known as endotoxins, are large molecules consisting of a lipid and a polysaccharide; they are found in the outer membrane of Gram-negative bacteria. LPS acts as the prototypical endotoxin because it binds the CD14/TLR4/MD2 receptor complex in many immune cell types, especially in monocytes, dendritic cells (DC), macrophages and B cells, which promotes the secretion of pro-inflammatory cytokines, nitric oxide, and eicosanoids.

In this study, human PBMCs were activated with these above-mentioned stimuli, including polyinosinic-polycytidylic acid (Poly (I:C)), SEB, CD3/CD28 and LPS, and then treated with test compounds or DMSO at indicated concentrations for 24-72 hours. Cell culture supernatants were collected and examined for the pro- and anti-inflammatory cytokine or chemokine secretion from PBMCs using Luminex-based multiplex cytokine assays. Data showed that the selected compound significantly module cytokine production from various immune cells in a concentration-dependent manner. Representative dose-responsive curves for modulating cytokine production were obtained based on the experiments.

Example 13. PPMs Suppressed Intracellular HDAC Activity in Cancer Cells Originated from Various Tissues in a Concentration Dependent Manner (FIG. 8)

The selected compound Compound 4, using the FDA-approved HDAC inhibitor cancer drug panobinostat at 50 nM as a positive control, was found to inhibit intracellular HDAC activity in a concentration dependent manner, when cancer cells were treated with the compounds for 24 h.

All references cited herein are incorporated herein by reference in their entireties. It will be appreciated by persons skilled in the art that the present invention is not limited to what has been particularly shown and described. Rather, the scope of the present invention is defined by the claims which follow. It should further be understood that the above description is only representative of illustrative examples of embodiments. The description has not attempted to exhaustively enumerate all possible variations. The alternate embodiments may not have been presented for a specific portion of the invention, and may result from a different combination of described portions, or that other un-described alternate embodiments may be available for a portion, is not to be considered a disclaimer of those alternate embodiments. It will be appreciated that many of those un-described embodiments are within the literal scope of the following claims, and others are equivalent.

We claim:
1. A compound represented by Formula I,

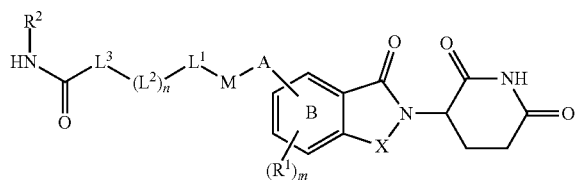

wherein
X is $CH_2$ or C=O,
$R^1$ in each instance is independently selected from the group consisting of 3-6 membered cycloalkyl, 3-6 membered heterocycloalkyl, $C_{1-4}$alkyl, $OC_{1-4}$alkyl, $NR^aR^b$, halo $C_{1-4}$alkyl, halogen, OH, CN, phenyl and 5- or 6-membered heteroaryl, wherein the phenyl and 5- or 6-membered heteroaryl are optionally substituted with one or more substituents selected from the group consisting of $C_{1-4}$alkyl, $OC_{1-4}$alkyl, $NR^aR^b$, halo $C_{1-4}$alkyl, halogen, OH, and CN;
$R^2$ is OH;
$R^a$ and $R^b$ in each instance is independently H or $C_{1-4}$alkyl;
A is $C_{1-3}$alkylene or void,
M is O, $OC_{1-3}$alkylene, $NR^a$, NHC(O)NH, O(CO)NH, NHC(O)O, or NHC(O), wherein O of $OC_{1-3}$alkylene is bonded to A or the B ring when A is void;
$L^1$ is NH, 3-6 membered heterocyclic, 6-membered aryl or 6-membered heteroaryl, halo$C_{1-2}$alkylene, $C_{1-3}$alkylene or void, wherein the aryl or heteroaryl is optionally substituted with one or more substituents selected from the group consisting of $C_{1-4}$alkyl, $OR^a$, SH, $NR^aR^b$, 3-6 membered cycloalkyl, $COOR^a$, CN, halogen, 3-6 membered cycloalkyl, $OC_{1-4}$alkyl, and halo$C_{1-4}$alkyl,
$L^2$ in each instance is independently selected from the group consisting of 3-6 membered heterocyclic, 6-membered aryl, 6-membered heteroaryl, —$(CH_2)_aC(O)NR^a$—, —$C(O)NR^a$—, —$(CH_2)_aC(O)NR^a(CH_2)_b$—, —$(CH_2)_a$—, —$(CH_2)_aO(CH_2CH_2O)_c$—, —$(CH_2)_aS$, —$(CH_2)_a$heterocyclyl-, —$(CH_2)_aC(O)$—, —$(CH_2)_aNR^a$—, —$CR^a$=N—$NR^a$—, —$CR^a$=N—O—, —$CR^a$=N—$NR^b$—CO—, —N=N—CO—, —S—S—, and any combination thereof, wherein a, b, and c are each an integer selected from 0 to 25, all subunits included;
$L^3$ is $C_{1-20}$alkylene, halo-$C_{1-20}$alkylene, $C_{2-20}$alkenlene, $C_{2-20}$alkynlene or void;
m is 0, 1, 2 or 3;
n is an integer selected from 0 to 25, all subunits included; or a pharmaceutically acceptable salt thereof,
provided that when A, $L^1$ and $(L^2)$n are void and M is NHC(O)NH, or NHC(O), M is not in an ortho position to X.
2. The compound or the pharmaceutically acceptable salt thereof of claim 1, wherein X is $CH_2$.
3. The compound or the pharmaceutically acceptable salt thereof of claim 1, wherein
X is $CH_2$;
A is $C_{1-3}$alkylene;
M is NHC(O);
$(L^2)$n optionally comprises —$(CH_2)_aO(CH_2CH_2O)_c$—.
4. The compound or the pharmaceutically acceptable salt thereof of claim 3, wherein $L^1$ is NH, 3-6 membered heterocyclic, 6-membered aryl, 6-membered heteroaryl, or halo$C_{1-2}$alkylene,

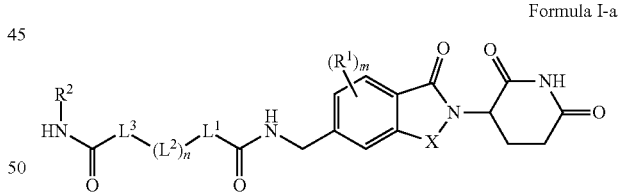

wherein the compound is represented by Formula I-a.
5. The compound or the pharmaceutically acceptable salt thereof of claim 1, wherein A is methylene or void,
X is $CH_2$
M is NHC(O),
$L^1$ is NH, halo$C_{1-2}$alkylene, $C_{1-3}$alkylene or void,
$(L^2)$n comprises optionally substituted phenyl,
n is an integer selected from 1 to 25, all subunits included.
6. The compound or the pharmaceutically acceptable salt thereof of claim 1, wherein A is methylene or void,
X is $CH_2$
M is NHC(O),
$L^1$ is halo-methylene, $C_{1-3}$alkylene or void,
$(L^2)$n comprises optionally substituted phenyl,
n is an integer selected from 1 to 25, all subunits included.

7. The compound or the pharmaceutically acceptable salt thereof of claim 6, wherein
$L^1$ is $CF_2$, $CH_2$, or void.

8. The compound or the pharmaceutically acceptable salt thereof of claim 6, wherein $L^1$ is $CH_2$, or void, A is $CH_2$.

9. The compound or the pharmaceutically acceptable salt thereof of claim 8,

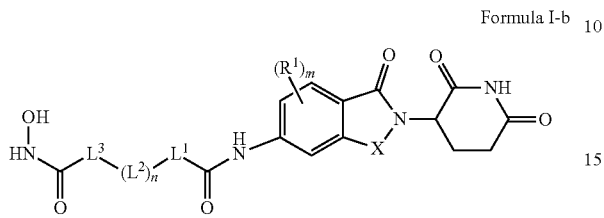

Formula I-b wherein the compound is represented by Formula I-b.

10. The compound or the pharmaceutically acceptable salt thereof of claim 8, wherein $L^1$ is NH, halo-methylene or $C_{1-3}$alkylene, $(L^2)n$ comprises optionally substituted phenyl.

11. The compound or the pharmaceutically acceptable salt thereof of claim 1,

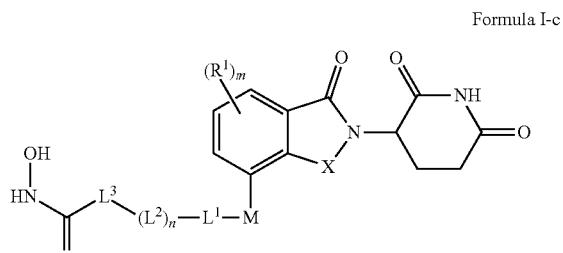

Formula I-c wherein the compound is represented by Formula I-c.

12. The compound or the pharmaceutically acceptable salt thereof of claim 1, wherein the compound is represented by Formula I-j,

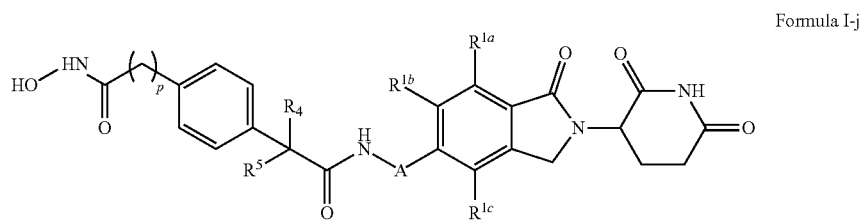

Formula I-j

Wherein
p is an integer from 1 to 20,
A is $C_{1-2}$alkylene or void,
$R^{1a}$, $R^{1b}$, and $R^{1c}$ in each instance are independently selected from the group consisting of 3-6 membered cycloalkyl, 3-6 membered heterocycloalkyl, $C_{1-4}$alkyl, $OC_{1-4}$alkyl, $NR^aR^b$, halo $C_{1-4}$alkyl, halogen, OH, and CN;
$R^4$ and $R^5$, are each independently H, halogen or $C_{1-4}$alkyl.

13. The compound or the pharmaceutically acceptable salt thereof of claim 12, wherein $R^4$ and $R^5$ are each independently H or halogen.

14. The compound or the pharmaceutically acceptable salt thereof of claim 1, wherein the compound is represented by Formula I-k,

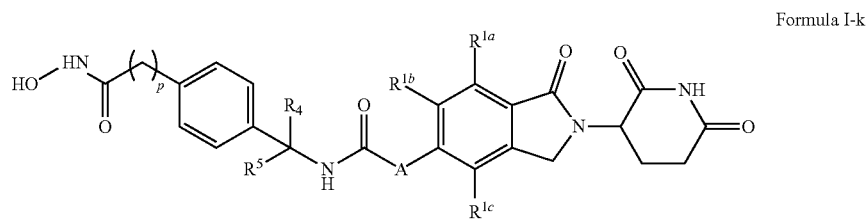

Formula I-k

Wherein
p is an integer from 1 to 20,
A is $C_{1-2}$alkylene or void,
$R^{1a}$, $R^{1b}$, and $R^{1c}$ in each instance are independently selected from the group consisting of 3-6 membered cycloalkyl, 3-6 membered heterocycloalkyl, $C_{1-4}$alkyl, $OC_{1-4}$alkyl, $NR^aR^b$, halo $C_{1-4}$alkyl, halogen, OH, and CN; and $R^4$ and $R^5$, are each independently H, halogen or $C_{1-4}$alkyl.

15. The compound or the pharmaceutically acceptable salt thereof of claim 14, wherein the nitrogen of NHC(O)NH, O(CO)NH, NHC(O)O or NHC(O) in M is bonded to $L^1$.

16. The compound or the pharmaceutically acceptable salt thereof of claim 1, wherein the compound is selected from the group consisting of compound 2

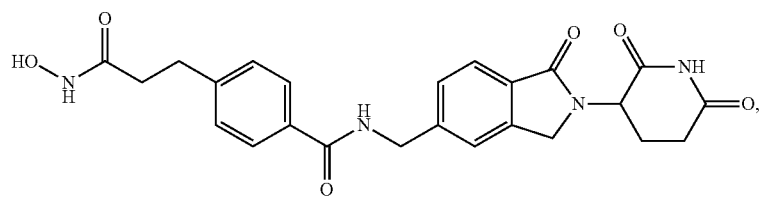

compound 4

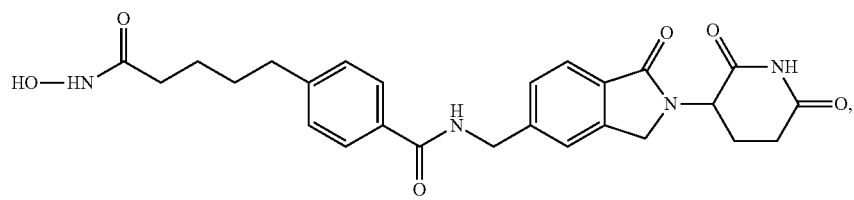

compound 5

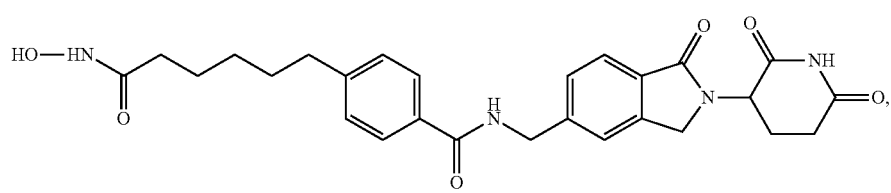

compound 7

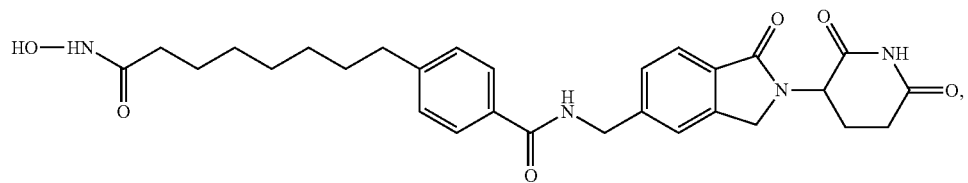

Compound 6

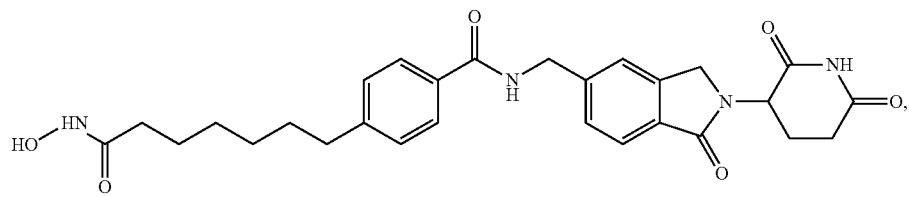

Compound 8

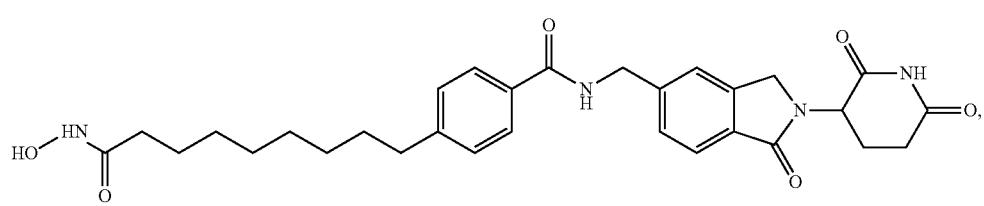

-continued
Compound 9
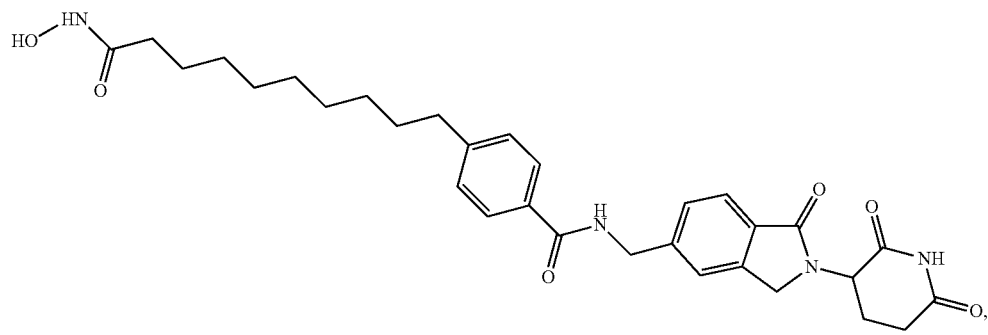
Compound 10
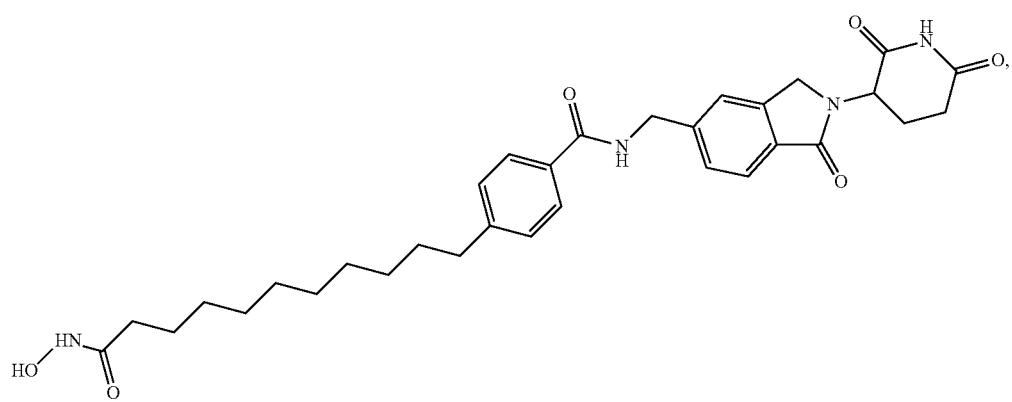
compound 204
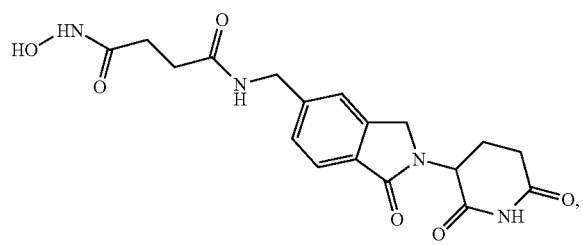
compound 219
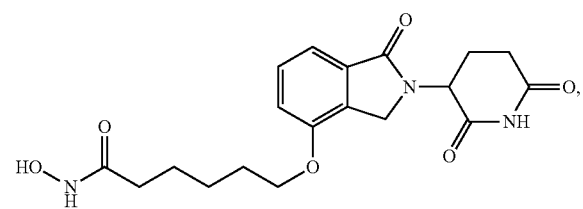
compound 217
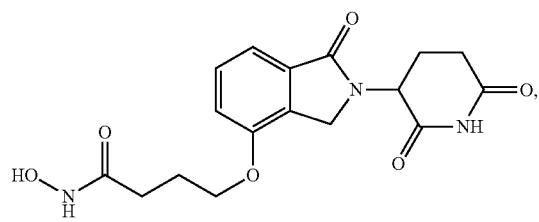
compound 216
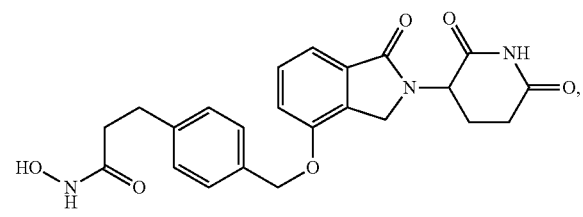
compound 256
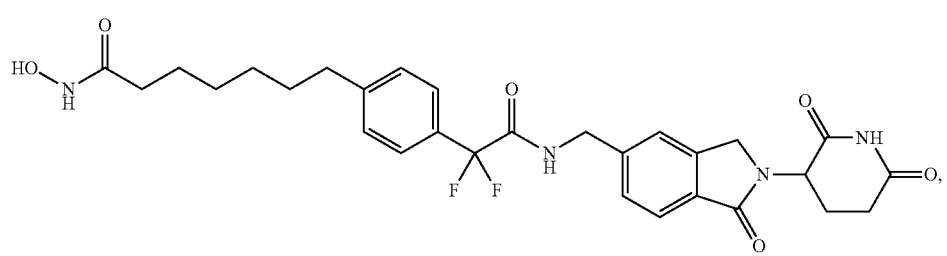

-continued compound 257
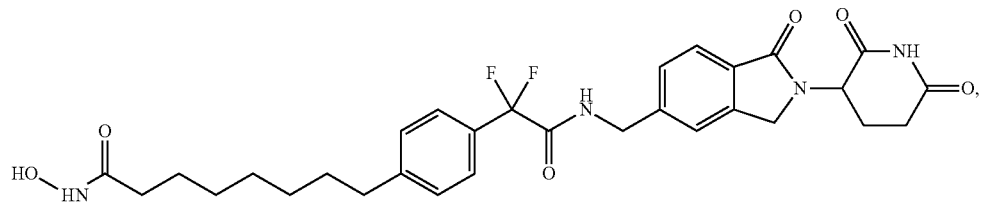

compound 448
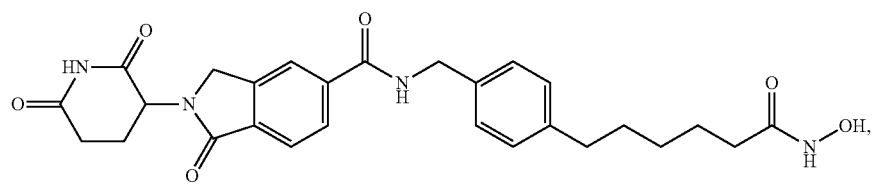

compound 449
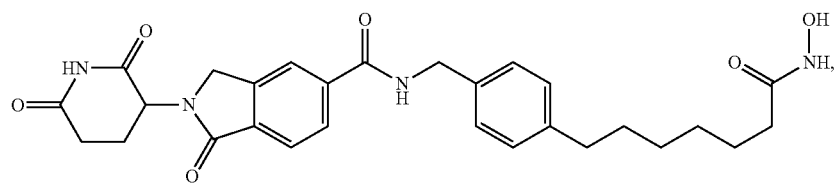

compound 479
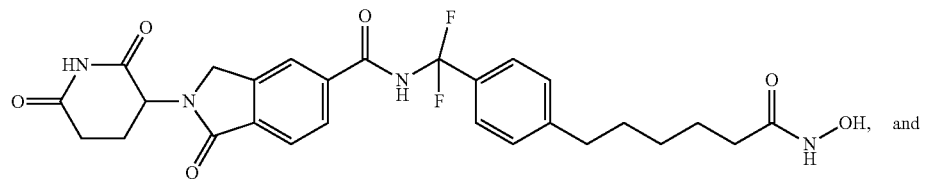

compound 481
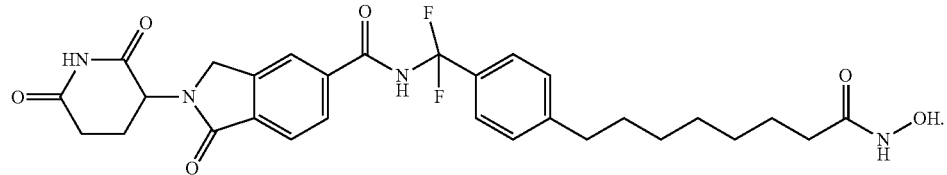

17. A pharmaceutical composition comprising a therapeutically effective amount of the compound or pharmaceutically acceptable salt thereof of claim 1.

18. The compound or the pharmaceutically acceptable salt thereof of claim 4, wherein A is bonded to M via nitrogen of the NHC(O).

19. The compound or the pharmaceutically acceptable salt thereof of claim 4, wherein A is CH$_2$.

20. The compound or the pharmaceutically acceptable salt thereof of claim 19, wherein L$^1$ is optionally substituted phenyl.

21. The compound or the pharmaceutically acceptable salt thereof of claim 19, wherein L$^1$ is phenyl, L$^3$ is C$_{3-9}$alkylene, and n is 0.

22. The compound or the pharmaceutically acceptable salt thereof of claim 1, wherein the compound is selected from the group consisting of compound 7
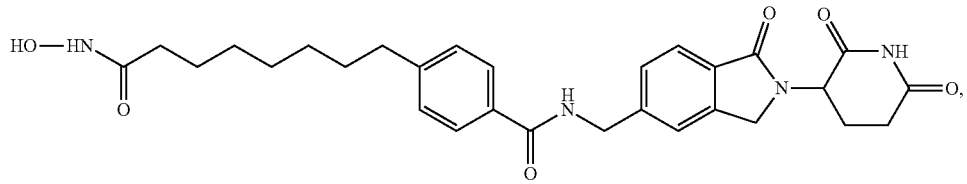

-continued
Compound 6
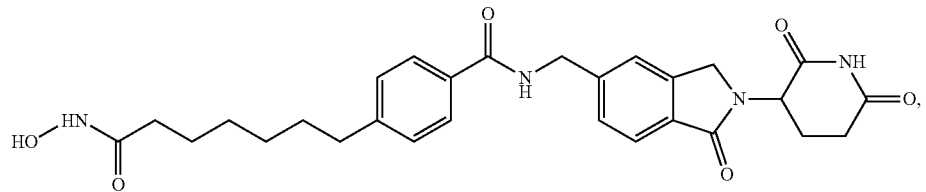
Compound 8
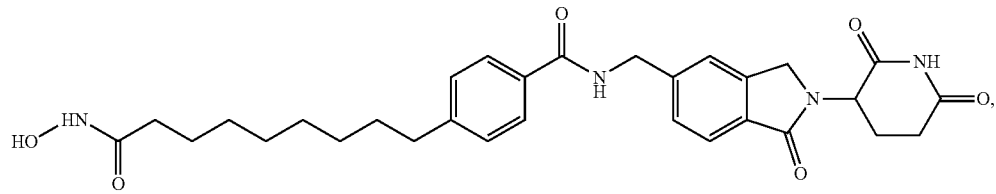
Compound 9
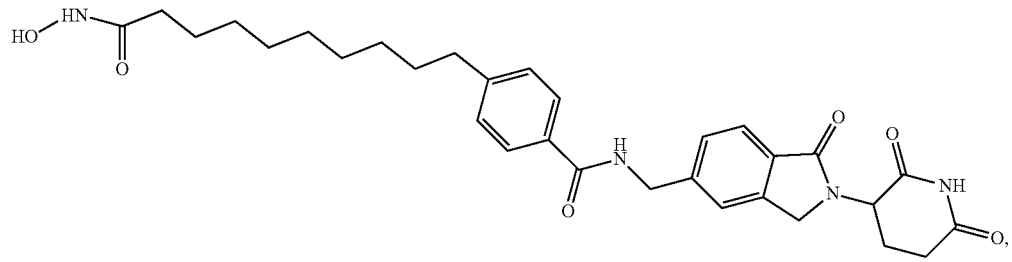
Compound 10
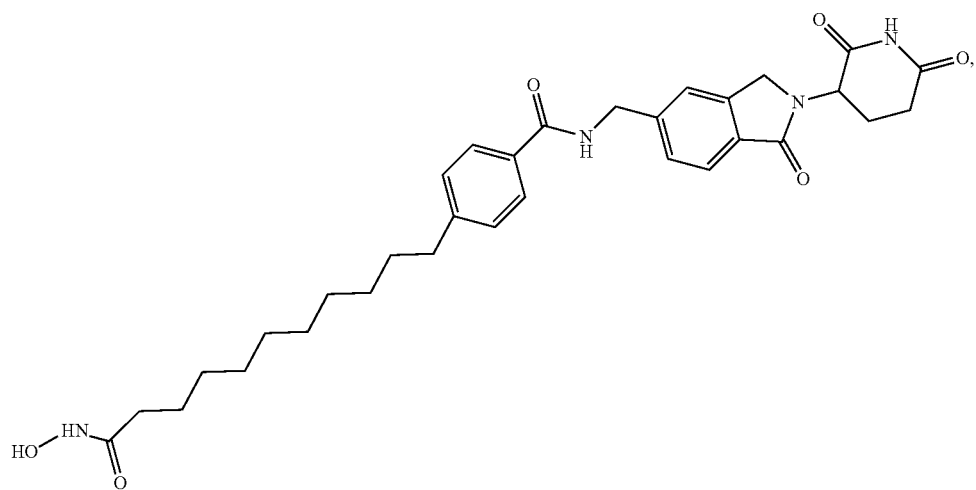
compound 256
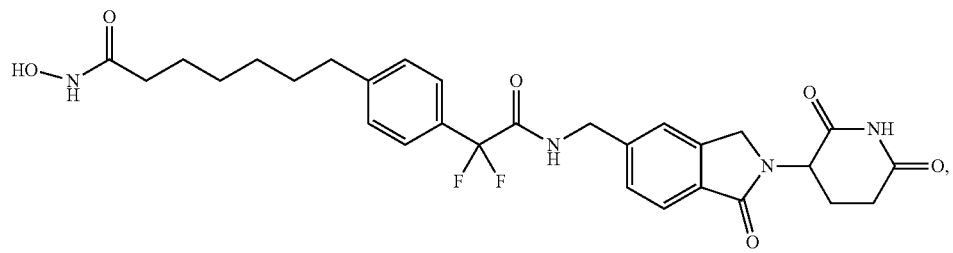
compound 257
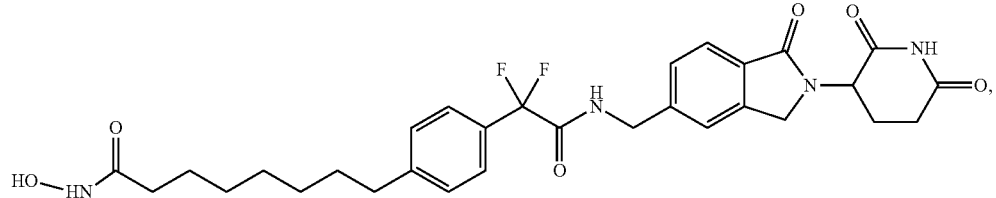

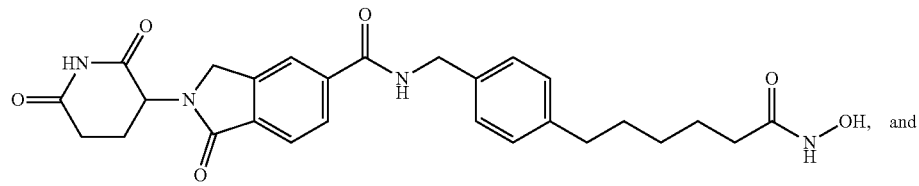

compound 448

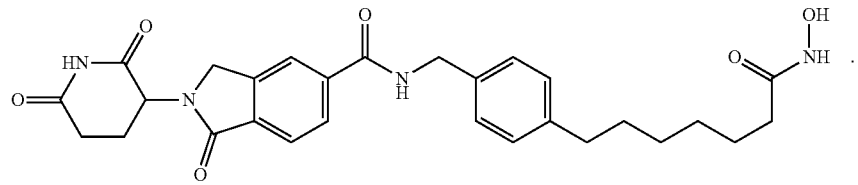

compound 449

23. The compound or the pharmaceutically acceptable salt thereof of claim 1, wherein L¹ is halo-methylene.

24. A method of treating a disease in a subject comprising administering to the subject a therapeutically effective amount of the compound or pharmaceutically acceptable salt thereof of claim 1, wherein the disease is selected from blood cancers, solid tissue cancers, autoimmune diseases, and other diseases involved in carcinogenesis, angiogenesis, immune dysregulation and infection.

25. The method of claim 24, wherein the disease is cancer selected from the group consisting of bladder cancer, breast cancer, colorectal adenocarcinoma, hepatoma, ovarian cancer, pancreatic cancer, prostate cancer, lung cancer and other solid tissue cancers, as well as blood cancer such as leukemia, lymphoma, and myeloma.

26. A method of degrading a target protein, comprising the target protein with a therapeutically effective amount of the compound or pharmaceutically acceptable salt thereof of claim 1, wherein the target protein is selected from the group consisting of c-MYC (cellular myelocytomatosis), n-MYC (also known as basic helix-loop-helix protein 37), CRBN (cereblon), HDAC (histone deacetylases), IKZF1 (Ikaros Zinc Finger Transcription Factor, Ikaros) IKZF2 (helios), IKZF3 (aiolos), IKZF4 (Eos), IRF4 (Interferon regulatory factor 4), NFκB (Nuclear factor kappa-light-chain-enhancer of activated B cells), p21 (CDK-interacting protein 1), p53 (tumor protein P53), and TNF-α (tumor necrosis factor alpha).

* * * * *